(12) United States Patent
Chen

(10) Patent No.: US 8,952,028 B2
(45) Date of Patent: Feb. 10, 2015

(54) METHODS OF TREATING CHEMORESISTANCE AND RELAPSE IN CANCER CELLS

(75) Inventor: Wenyong Chen, Temple City, CA (US)

(73) Assignee: City of Hope, Duarte, CA (US)

(*) Notice: Subject to any disclaimer, the term of this patent is extended or adjusted under 35 U.S.C. 154(b) by 1491 days.

(21) Appl. No.: 12/026,554

(22) Filed: Feb. 5, 2008

(65) Prior Publication Data

US 2011/0178153 A1    Jul. 21, 2011

Related U.S. Application Data

(60) Provisional application No. 60/888,307, filed on Feb. 5, 2007.

(51) Int. Cl.

| | | |
|---|---|---|
| *A01N 43/54* | (2006.01) | |
| *A61K 31/505* | (2006.01) | |
| *C07D 239/02* | (2006.01) | |
| *A61K 31/366* | (2006.01) | |
| *A61K 31/05* | (2006.01) | |
| *A61K 31/404* | (2006.01) | |
| *A61K 31/7105* | (2006.01) | |
| *A61K 31/713* | (2006.01) | |
| *A61K 45/06* | (2006.01) | |
| *G01N 33/50* | (2006.01) | |

(52) U.S. Cl.
CPC .............. *A61K 31/366* (2013.01); *A61K 31/05* (2013.01); *A61K 31/404* (2013.01); *A61K 31/7105* (2013.01); *A61K 31/713* (2013.01); *A61K 45/06* (2013.01); *G01N 33/5011* (2013.01)
USPC ............ 514/274; 514/275; 544/297; 544/317

(58) Field of Classification Search
USPC ........................... 514/274, 275; 544/297, 317
See application file for complete search history.

(56) References Cited

FOREIGN PATENT DOCUMENTS

| WO | WO 2006006171 A2 * | 1/2006 |
| WO | WO 2006081329 A2 * | 8/2006 |
| WO | 2008/029096 A2 | 3/2008 |

OTHER PUBLICATIONS

O'Hare et. al., Current Opinion in Genetics and Development, 2006, Elsevier, vol. 16, pp. 92-99.*
Xiong et. al., Bioorganic and Medicinal Chemistry, 2001, Pergamon, vol. 9, pp. 1773-1780.*
Chabner et. al., Nature Rev. Cancer, 2005, Nature Publishing Group, vol. 5, pp. 65-72.*
Rich et. al., Nature Rev. Drug Disc., 2004, Nature Publishing Group, vol. 3, pp. 430-446.*
Beger et. al., World J. Surg., 2003, Societe Internationale de Chirurgie, vol. 27, pp. 1075-1083.*
Posakony et. al., Journal of Medicinal Chemistry, 2004, American Chemical Society, vol. 47, pp. 2635-2644.*
Martinelli et. al., Leukemia, 2005, Nature Publishing Group, vol. 19, pp. 1872-1879.*
Leaf, Fortune, Mar. 2004, ProQuest, vol. 149, issue 6, pp. 1-29 (pp. 76-97 online).*
Anand, S., et al., "Aurora-A Amplification Overrides the Mitotic Spindle Assembly Checkpoint, Inducing Resistance to Taxol," Cancer Cell 3:51-62 (2003).
Andrews, P. D., "Aurora Kinases: Shining Lights on the Therapeutic Horizon?," Oncogene 24:5005-5015 (2005).
Avalos, J. L., et al., "Mechanism of Sirtuin Inhibition by Nicotinamide: Altering the NAD$^+$ Cosubstrate Specificity of a Sir2 Enzyme," Mol Cell 17:855-868 (2005).
Balaban, R. S., et al., "Mitochondria, Oxidants, and Aging," Cell 120:483-495 (2005).
Baselga, J., et al., "Phase I Safety, Pharmacokinetic, and Pharmacodynamic Trial of ZD1839, a Selective Oral Epidermal Growth Factor Receptor Tyrosine Kinase Inhibitor, in Patients with Five Selected Solid Tumor Types," J Clin Oncol 20:4292-4302 (2002).
Baselga, J., "Targeting Tyrosine Kinases in Cancer: The Second Wave," Science 312:1175-1178 (2006).
Bassan, R., et al., "Adult Acute Lymphoblastic Leukaemia," Crit Rev Oncol Hematol 50:223-261 (2004).
Baur, J. A., et al., "Resveratrol Improves Health and Survival of Mice on a High-Calorie Diet," Nature 444:337-342 (2006).
Bedalov, A., et al., "Identification of a Small Molecule Inhibitor of Sir2p," Proc Natl Acad Sci 98:15113-15118 (2001).
Bi, S., et al., "p53 in Chronic Myeloid Leukemia Cell Lines," Leukemia 6:839-842 (1992).
Bitterman, K. J., et al., "Inhibition of Silencing and Accelerated Aging by Nicotinamide, a Putative Negative Regulator of Yeast Sir2 and Human SIRT1," J Biol Chem 277:45099-45107 (2002).

(Continued)

*Primary Examiner* — Sarah Pihonak
(74) *Attorney, Agent, or Firm* — Perkins Coie LLP; Courtney Prochnow

(57) ABSTRACT

Methods of treating or preventing chemoresistance or relapse growth of cancer cells are provided. Methods of treating or preventing resistance to tyrosine kinase based chemotherapeutic treatment in hematologic and solid tumors are provided. BCR-ABL drug resistance in chronic myelogenous leukemia (CML) and models for conducting further study on the same are presented. The methods comprise administering a therapeutically effective amount of one or more SIRT1 modulators to the cells or subject in need thereof. The methods may be administered in combination with, prior to or subsequent to chemotherapy or may be administered to counteract the effect of a spontaneous genetic mutation. Methods of using SIRT1 inhibitors to treat or prevent insulin and transferrin-induced resistance are also presented. A novel cell model to study mechanisms of acquired chemoresistance is also provided.

7 Claims, 20 Drawing Sheets

(56) References Cited

OTHER PUBLICATIONS

Blume-Jensen, P., et al., "Oncogenic Kinase Signalling," Nature 411:355-365 (2001).
Bordone, L., et al., "Sirt1 Regulates Insulin Secretion by Repressing UCP2 in Pancreatic β Cells," PLoS 4:210-220 (2006).
Branford, S., et al., "High Frequency of Point Mutations Clustered Within the Adenosine Triphosphate-Binding Region of BCR/ABL in Patients with Chronic Myeloid Leukemia of Ph-Positive Acute Lymphoblastic Leukemia Who Develop Imatinib (STI571) Resistance," Blood 99:3472-3475 (2002).
Brunet, A., et al., "Stress-Dependent Regulation of FOXO Transcription Factors by the SIRT1 Deacetylase," Science 303:20112015 (2004).
Burchert, A., et al., "Compensatory PI3-Kinase/Akt/mTor Activation Regulates Imatinib Resistance Development," Leukemia 19:1774-1782 (2005).
Burkhart-Schultz, K. J., et al., "Spectrum of Somatic Mutation at the Hypoxanthine Phosphoribosyltransferase (hprt) gene of healthy people," Carcinogenesis 17:1871-1883 (1996).
Canitrot, Y., et al., "Mutator Phenotype of BCR-ABL Transfected Ba/F3 Cell Lines and Its Association with Enhanced Expression of DNA Polymerase β," Oncogene 18:2676-2680 (1999).
Carter, M. G., et al., "Mice Deficient in the Candidate Tumor Supresor Gene Hic1 Exhibit Developmental Defects of Structures Affected in the Miller-Dieker Syndrome," Hum Mol Genet 9:413-419 (2000).
Carter, T. A., et al., "Inhibition of Drug-Resistant Mutants of ABL, KIT, and EGF Receptor Kinases," Proc Natl Acad Sci USA 102:11011-11016 (2005).
Chen, P. M., et al., "Insulin Receptors on Leukemia and Lymphoma Cells," Blood 62:251-255 (1983).
Chen, W. Y., et al., "Epigenetic and Genetic Loss of Hic1 Function Accentuates the Role of p53 in Tumorigenesis," Cancer Cell 6:387-398 (2004).
Chen, W. Y., et al., "Heterozygous Disruption of Hic1 Predisposes Mice to a Gender-Dependent Spectrum of Malignant Tumors," Nat Genet 33:197-202 (2003).
Chen, W. Y., et al., "Inactivation of Tumor Suppressor Genes," Cell Cycle 4:10-12 (2005).
Chen, W. Y., et al., "Tumor Suppressor HIC1 Directly Regulates SIRT1 to Modulate p53-Dependent DNA-Damage Responses," Cell 123:437-448 (2005).
Chu, F., et al., "Control of Multidrug Resistance Gene mdr1 and Cancer Resistance to Chemotherapy by the Longevity Gene sirt1," Cancer Res 65:10183-10187 (2005).
Cohen, H. Y., et al., "Calorie Restriction Promotes Mammalian Cell Survival by Inducing the SIRT1 Deacetylase," Science 305:390-392 (2004).
Cohen, M. H., et al., "United States Food and Drug Administration Drug Approval Summary: Gefitinib (ZD1839; Iressa) Tablets," Clin Cancer Res 10:1212-1218 (2004).
Cragg, M. S., et al., "Gefitinib-Induced Killing of NSCLC Cell Lines Expressing Mutant EGFR Requires BIM and Can Be Enhancesd by BH3 Mimetics," PLoS Med 4:1681-1690 (2007).
Crane, R., et al., "Requirements for the Destruction of Human Aurora-A," J Cell Sci 117:5975-5983 (2004).
Czechowska, A., et al., "Imatinib (STI571) Induces DNA Damage in BCR/ABL-Expressing Leukemic Cells But Not in Normal Lymphocytes," Chem Biol Interact 152:139-150 (2005).
Daitoku, H., et al., "Silent Information Regulator 2 Potentiates Foxo 1-Mediated Transcription Through its Deacetylase Activity," Proc Natl Acad Sci USA 101:10042-10047 (2004).
De Ruijter, A. J. M., et al., "Histone Deacetylases (HDACs): Characterization of the Classical HDAC Family," Biochem J 370:737-749 (2003).
Deininger, M. W. N., et al., "Specific Targeted Therapy of Chronic Myelogenous Leukemia with Imatinib," Pharmacol Rev 55:401-423 (2003).
Deininger, M. W., et al., "The Tyrosine Kinase Inhibitor CGP57148B Selectively Inhibits the Growth of BCR-ABL-Positive Cells," Blood 90:3691-3698 (1997).
Engelman, J. A., et al., "Allelic Dilution Obscures Detection of a Biologically Significant Resistance Mutation in EGFR-Amplified Lung Cancer," J Clin Invest 116:2695-2706 (2006).
Engelman, J. A., et al., "MET Amplification Leads to Gefitinib Resistance in Lung Cancer by Activating ERBB3 Signaling," Science 316:1039-1043 (2007).
Ford, J., et al., "Cancer-Specific Functions of SIRT1 Enable Human Epithelial Cancer Cell Growth and Survival," Cancer Res 65:10457-10463 (2005).
Frye, R. A., "Characterization of Five Human cDNAs with Homology to the Yeast SIR2 Gene: Sir2-like Proteins (Sirtuins) Metabolize NAD and May Have Protein ADP-Ribosyltransferase Activity," Biochem Biophys Res Commun 260:273-279 (1999).
Frye, R. A., "Phylogenetic Classification of Prokaryotic and Eukaryotic Sir2-like Proteins," Biochem Biophys Res Commun 273:793-798 (2000).
Gambacorti-Passerini, C. B., et al., "Molecular Mechanisms of Resistance to Imatinib in Piladelphia-Chromosome-Positive Leukaemias," Lancet Oncol 4:75-85 (2003).
Giles, F. J., et al., "MK-0457, a Novel Kinase Inhibitor, is Active in Patients with Chronic Myeloid Leucemia or Acute Lymphocytic leucemia with the T315I BCR-ABL Mutation," Blood 109:500-502 (2007).
Gorre, M. E., et al., "Clinical Resistance to STI-571 Cancer Therapy Caused by BCR-ABL Gene Mutation or Amplification," Science 293:876-880 (2001).
Grozinger, C. M., et al., "Identification of a Class of Small Molecule Inhibitors of the Sirtuin Family of NAD-Dependent Deacetylases by Phenotypic Screening," J Biol Chem 276:38837-38843 (2001).
Guarente, L., "Sir2 Links Chromatin Silencing, Metabolism, and Aging," Genes Devel 14:1021-1026 (2000).
Guerardel, C., et al., "Identification in the Human Candidate Tumor Suppressor Gene HIC-1 of a New Major Alternative TATA-Less Promoter Positively Regulated by p53," J Biol Chem 276:3078-3089 (2001).
Harrington, E. A., et al., "VX-680, A Potent and Selective Small-Molecule Inhibitor of the Aurora Kinases, Suppresses Tumor Growth In Vivo," Nat. Med. 10:262-267 (2004).
Hirao, M., et al., "Identification of Selective Inhibitors of $NAD^+$-Dependent Deacetylases Using Phenotypic Screens in Yeast," J Biol Chem 278:52773-52782 (2003).
Howitz, K. T., et al., "Small Molecule Activators of Sirtuins Extend *Saccharomyces cerevisiae* Lifespan," Nature 425:191-196(2003).
Huffman, D. M., et al., "SIRT1 is Significantly Elevated in Mouse and Human Prostate Cancer," Cancer Res 67:6612-6618 (2007).
Imai, S., et al., "Transcriptional Silencing and Longevity Protein Sir2 Is an NAD-Dependent Histone Deacetylase," Nature 403:795-800 (2000).
Inukai, M., et al., "Presence of Epidermal Growth Factor Receptor Gene T790M Mutation as a Minor Clone in Non-Small Cell Lung Cancer," Cancer Res 66:7854-7858 (2006).
Issa, J. P. J., et al., "HIC1 Hypermethylation Is a Late Event in Hematopoietic Neoplasms," Cancer Res 57:1678-1681 (1997).
Jones, P. A., et al., "The Fundamental Role of Epigenetic Events in Cancer," Nat Rev Genet 3:415-428 (2002).
Kaeberlein, M., et al., "The SIR 2/3/4 Complex and SIR2 Alone Promote Longevity in *Saccharomyces cerevisiae* by Two Different Mechanisms," Genes Devel 13:2570-2580 (1999).
Kantarjian, H., et al., "Nilotinib in Imatinib-Resistant CML and Philadelphia Chromosome-Positive ALL," N Engl J Med 354:2542-2551 (2006).
Kawano, T., et al., "Depsipeptide Enhances Imatinib Mesylate-Induced Apoptosis of Bcr-Abl-Positive Cells and Ectopic Expression of Cyclin D1, c-Myc or Active MEK Abrogates This Effect," AntiCancer Res 24:2705-2712 (2004).
Keen, N., et al., "Aurora-Kinase Inhibitors as Anticancer Agents," Nat Rev Cancer 4:927-936 (2004).
Kelly, D. P., et al., "Transcriptional Regulatory Circuits Controlling Mitochondrial Biogenesis and Function," Genes Devel 18:357-368 (2004).

(56) References Cited

OTHER PUBLICATIONS

Kharbanda, S., et al., "Functional Interaction Between DNA-PK and c-Abl in Response to DNA Damage," Nature 386:732-735 (1997).
Klejman, A., et al., "Phosphatidylinositol-3 Kinase Inhibitors Enhance the Anti-Leukemia Effect of STI571," Oncogene 21:5868-5876 (2002).
Kobayashi, S., et al., "EGFR Mutation and Resistance of Non-Small-Cell Lung Cancer to Gefitinib," N Engl J Med 352:786-792 (2005).
Koptyra, M., et al., "BCR/ABL Kinase Induces Self-Mutagenesis via Reactive Oxygen Species to Encode Imatinib Resistance," Blood 108:319-327 (2006).
Kosaka, T., et al., "Analysis of Epidermal Growth Factor Receptor Gene Mutation in Patients with Non-Small Cell Lung Cancer and Acquired Resistance to Gefitinib," Clin Cancer Res 12:5764-5769 (2006).
Kowolik, C. M., et al., "HIV Vector Production Mediated by Rev Protein Transduction," Mol Ther 8:324-331 (2003).
Kuzmichev, A., et al., "Composition and Histone Substrates of Polycomb Repressive Group Complexes Change During Cellular Differentiation," Proc Natl Acad Sci USA 102:1859-1864 (2005).
Kwak, E. L., et al., "Irreversible Inhibitors of the EGF Receptor May Circumvent Acquired Resistance to Gefitinib," Proc Natl Acad Sci USA 102:7665-7670 (2005).
Lagouge, M., et al., "Resveratrol Improves Mitochondrial Function and Protects Against Metabolic Disease by Activating SIRT1 and PGC-1α," Cell 127:1109-1122 (2006).
La Rosee, P., et al., "Activity of the Bcr-Abl Kinase Inhibitor PD180970 Against Clinically Relevant Bcr-Abl Isoforms That Cause Resistance to Imatinib Mesylate (Gleevec, STI571)," Cancer Res 62:7149-7153 (2002).
La Rosee, P., et al., "In Vitro Efficacy of Combined Treatment Depends on the Underlying Mechanism of Resistance in Imatinib-Resistant Bcr-Abl-Positive Cell Lines," Blood 103:208-215 (2004).
Landry, J., et al., "The Silencing Protein SIR2 and Its Homologs are NAD-Dependent Protein Deacetylases," Proc Natl Acad Sci USA 97:5807-5811 (2000).
Le Coutre, P., et al., "In Vivo Eradication of Human BCR/ABL-Positive Leukemia Cells with an ABL Kinase Inhibitor," J Natl Cancer Inst 91:163-168 (1999).
Li, M. J., et al., "Inhibition of HIV-1 Infection by Lentiviral Vectors Expressing Pol III-Promoted Anti-HIV RNAs," Mol Ther 8:196-206 (2003).
Lin, S. J., et al., "Requirement of NAD and SIR2 for Life-Span Extensión by Calorie Restriction in *Saccharomyces cerevisiae*," Science 289:2126-2128 (2000).
Littlepage, L. E., et al., "Identification of a New APC/C Recognition Domain, the A Box, Which is Required for the Cdh1-Dependent Destruction of the Kinase Aurora-A During Mitotic Exit," Genes Devel 16:2274-2285 (2002).
Littlepage, L. E., et al., "Identification of Phosphorylated Residues That Affect the Activity of the Mitotic Kinase Aurora-A," Proc Natl Acad Sci USA 99:15440-15445 (2002).
Luo, J., et al., "Negative Control of p53 by Sir2α Promotes Cell Survival ander Stress," Cell 107:137-148 (2001).
Ly, C., et al., "Bcr-Abl Kinase Modulates the Translation Regulators Ribosomal Protein S6 and 4E-BP1 in Chronic Myelogenous Leucemia Cells via the Mammalian Target of Rapamycin," Cancer Res 63:5716-5722 (2003).
Lynch, T. J., et al., "Activating Mutations in the Epidermal Growth Factor Receptor Underlying Responsiveness of Non-Small-Cell Lung Cancer to Gefitinib," N Engl J Med 350:2129-2139 (2004).
Maguer-Satta, V., et al., "BCR-ABL Accelerates C2-Ceramide-Induced Apoptosis," Oncogene 16:237-248 (1998).
Mahon, F. X., et al., "Selection and Characterization of BCR-ABL Positive Cell Lines with Differential Sensitivity to the Tyrosine Kinase Inhibitor STI571: Diverse Mechanisms of Resistance," Blood 96:1070-1079 (2000).
Mai, A., et al., "Design, Sintesis, and Biological Evaluation of Sirtinol Analogues as Class III Histone/Protein Deacetylase (Sirtuin) Inhibitors," J Med Chem 48:7789-7795 (2005).

Marumoto, T., et al., "Aurora-A—A Guardian of Poles," Nat Rev Cancer 5:42-50 (2005).
Michor, F., et al., "Dynamics of Chronic Myeloid leukaemia," Nature 435:1267-1270 (2005).
Motta, M. C., et al., "Mammalian SIRT-1 Represses Forkhead Transcription Factors," Cell 116:551-563 (2004).
Moynihan, K. A., et al., "Increased Dosage of Mammalian Sir2 in Pancreatic β Cells Enhances Glucose-Stimulated Insulin Secretion in Mice," Cell Metab 2:105-117 (2005).
Narayan, G., et al., "Frequent Promoter Methylation of CDHI, DAPK, RARB, and HICI Genes in Carcinoma of Cerviz Uteri: Its Relationship to Clinical Outcome," Mol Cancer 2:24 (2003).
Nemoto, S., et al., "Nutrient Availibility Regulates SIRT1 Through a Forkhead-Dependent Pathway," Science 306:2105-2108 (2004).
Neubauer, A., et al., "Genetic Alterations in the p53 Gene in the Blast Crisis of Chronic Myelogeneous Leucemia: Analysis by Polymerase Chain Reaction Based Techniques," Leukemia 7:593-600 (1993).
North, B. J., et al., "Sirtuins: Sir2-Related NAD-Dependent Protein Deacetylases," Genome Biol 5:224 (2004).
Ogino, A., et al., "Emergence of Epidermal Growth Factor Receptor T790M Mutation During Chronic Exposure to Gefitinib in a Non-Small Cell Lung Cancer Cell Line," Cancer Res 67:7807-7814(2007).
Osterholm, A. M., et al., "Classification of Mutations at the Human Hprt-Locus in T-Lymphocytes of Bus Maintenance Workers by Multiplex-PCR and Reverse Transcriptase-PCR Analysis," Carcinogenesis 16:1909-1912 (1995).
Paez, J. G., et al., "EGFR Mutations in Lung Cancer: Correlation with Clinical Response to Gefitinib Therapy," Science 304:1497-1500 (2004).
Pan, J., et al., "An Aurora Kinase Is Essential for Flagellar Disassembly in *Chlamydomonas*," Devel Cell 6:445-451 (2004).
Pao, W., et al., "Acquired Resistance of Lung Adenocarcinomas to Gefitinib or Erlotinib Is Associated with a Second Mutation in the EGFR Kinase Domain," PLoS Med 2:225-235 (2005).
Pao, W., et al., "EGF Receptor Gene Mutations are Common in Lung Cancers from "Never Smokers" and are Associated with Sensitivity of Tumors to Gefitinib and Erlotinib," Proc Natl Acad Sci USA 101:13306-13311 (2004).
Pear, W. S., et al., "Efficient and Rapid Induction of a Chronic Myelogenous Leukemia-Like Myeloproliferative Disease in Mice Receiving P210 bcr/abl-Transduced Bone Marrow," Blood 92:3780-3792 (1998).
Peng, B., et al., "Clinical Pharmacokinetics of Imatinib," Clin Pharmacokinet 44:879-894 (2005).
Podlutsky, A., et al., "Spectrum of Point Mutations in the Coding Region of the Hypoxanthine-Guanine Phosphoribosyltransferase (hprt) Gene in Human T-Lymphocytes In Vivo," Carcinogenesis 19:557-566 (1998).
Rapozzi, V., et al., "Efficient Silencing of bcrlabl Oncogene by Single- and Double-Stranded siRNAs Targeted Against b2a2 Transcripts," Biochem 43:16134-16141 (2004).
Rathi, A., et al., "Aberrant Methylation of the HIC1 Promoter Is a Frequent Event in Specific Pediatric Neoplasms," Clin Cancer Res 9:3674-3678 (2003).
Reynolds, A., et al., "Racional siRNA Designm for RNA Interference," Nat Biotechnol 22:326-330 (2004).
Rodgers, J. T., et al., "Nutrient Control of Glucosa Homeostasis Through a Complex of PGC-1α and SIRT1," Nature 434:113-118 (2005).
Santini, V., et al., "Changes in DNA Methylation in Neoplasia: Pathophysiology and Therapeutic Implications," Ann Intern Med 134:583-586 (2001).
Sattler, M., et al., "The BCR/ABL Tyrosine Kinase Induces Production of Reactive Oxygen Species in Hematopoietic Cells," J Biol Chem 275:24273-24278 (2000).
Saunders, L. R., et al., "Sirtuins: Critical Regulators at the Crossroads Between Cancer and Aging," Oncogene 26:5489-5504 (2007).
Schindler, T., et al., "Structural Mechanism for STI-571 Inhibition of Abelson Tyrosine Kinase," Science 289:1938-1942 (2000).
Shafman, T., et al., "Interaction Between ATM Protein and c-Abl in Response to DNA Damage," Nature 387:520-523 (1997).

(56) References Cited

OTHER PUBLICATIONS

Shah, N. P., et al., "Mechanisms of Resistance of STI571 in Philadelphia Chromosome-Associated Leucemias," Oncogene 22:7389-7395 (2003).
Shah, N. P., et al., "Multiple BCR-ABL Kinase Domain Mutations CONFER Polyclonal Resistance to the Tyrosine Kinase Inhibitor Imatinib (STI571) in Chronic Phase and Blast Crisis Chronic Myeloid Leucemia," Cancer Cell 2:117-125 (2002).
Shah, N. P., et al., "Overriding Imatinib Resistance With a Novel ABL Kinase Inhibitor," Science 305:399-401 (2004).
Skorski, T., et al., "Phosphatidylinositol-3 Kinase Activity Is Regulated by BCR/ABL and Is Required for the Growth of Philadelphia Chromosome-Positive Cells," Blood 86:726-736 (1995).
Slupianek, A., et al., "BCR/ABL Modifies the Kinetics and Fidelity of DNA Double-Strand Breaks Repair in Hematopoietic Cells," DNA Repair 5:243-250 (2006).
Soverini, S., et al., "Contribution of ABL Kinase Domain Mutations to Imatinib Resistance in Different Subsets of Philadelphia-Positive Patients: By the GIMENA Working Party on Chronic Myeloid leucemia," Clin Cancer Res 12:7374-7379 (2006).
Stamos, J., et al., "Structure of the Epidermal Growth Factor Receptor Kinase Domain Alone and in Complex with a 4-Anilinoquinazoline Inhibitor," J Biol Chem 277:46265-46272 (2002).
Szabo, P. E., et al., "The Chicken β-Globin Insulator Element Conveys Chromatin Boundary Activity but Not Imprinting at the Mouse Igf2/H19 Domain," Development 129:897-904 (2002).
Talpaz, M., et al., "Dasatinib in Imatinib-Resistant Philadelphia Chromosome-Positive Leucemias," N Engl J Med 354:2531-2541 (2006).
Tang, S. H. E., et al., "A Cre/loxP-Deleter Transgenic Line in Mouse Strain 129S1/SvImJ," Genesis 32:199-202 (2002).
Tanner, K. G., et al., "Silent Information Regulator 2 Family of NAD-Dependent Histone/Protein Deacetylases Generates a Unique Product, 1-0-Acetyl-ADP-Ribose," Proc Natl Acad Sci USA 97:14178-14182 (2000).
Tanny, J. C., et al., "Coupling of Histone Deacetylation to NAD Breakdown by the Yeast Silencing Protein Sir2: Evidence for Acetyl Transfer from Substrate to an NAD Breakdown Product," Proc Natl Acad Sci USA 98:415-420 (2001).
Tissenbaum, H. A., et al., "Increased Dosage of a sir-2 Gene Extends Lifespan in *Caenorhabditis elegans*," Nature 410:227-230 (2001).
Van Der Horst, A., et al., "FOXO4 Is Acetylated Upon Peroxide Stress and Deacetylated by the Longevity Protein hSir2$^{SIRT1}$," J Biol Chem 279:28873-28879 (2004).
Vaziri, H., et al., "hSIR2$^{SIRT1}$ Functions as an NAD-Dependent p53 Deacetylase," Cell 107:149-159 (2001).
Ventura, A., et al., "Cre-lox-Regulated Condicional RNA Interferente from Transgenes," Proc Natl Acad Sci USA 101:10380-10385 (2004).
Von Bubnoff, N., et al., "A Cell-Based Screen for Resistance of Bcr-Abl-Positive leucemia Identifies the Mutation Pattern for PD166326, an Alternative Abl Kinase Inhibitor," Blood 105:1652-1659 (2005).
Von Bubnoff, N., et al., "Bcr-Abl Resistance Screening Predicts a Limited Spectrum of Point Mutations to be Associated with Clinical Resistance to the Abl Kinase Inhibitor Nilotinib (AMN107)," Blood 108:1328-1333 (2006).
Von Bubnoff, N., et al., "Resistance of Philadelphia-Chromosome Positive Leucemia Towards the Kinase Inhibitor Imatinib (STI571, Glivec): a Targeted Oncoprotein Strikes Back," Leucemia 17:829-838 (2003).
Wales, M. M., et al., "p53 Activates Expresión of HIC-1, a New Candidate Tumour Suppressor Gene on 17p13.3," Nat Med 1:570-577 (1995).
Weisberg, E., et al., "Characterization of AMN107, a Selective Inhibitor of Native and Mutant Bcr-Abl," Cancer Cell 7:129-141 (2005).
Woo, R. A., et al., "Activated Oncogenes Promote and Cooperate with Chromosomal Instability for Neoplastic Transformation," Genes Devel 18:1317-1330 (2004).
Wood, J. G., et al., "Sirtuin Activators Mimic Caloric Restriction and Delay Ageing in Metazoans," Nature 430:686-689 (2004).
Xiao, H., et al., "Acidic pH Induces Topoisomerase II-Mediated DNA Damage," Proc Natl Acad Sci USA 100:5205-5210 (2003).
Yu, C., et al., "Histone Deacetylase Inhibitors Promote STI571-Mediated Apoptosis in STI571-Sensitive and -Resistant Bcr/Abl$^+$ Human Myeloid Leukemia Cells," Cancer Res 63:2118-2126 (2003).
Yuan, Z., et al., "SIRT1 Regulates the Function of the Nijmegen Breakage Syndrome Protein," Mol Cell 27:149-162 (2007).
Scappini, B., et al., "Changes Associated with the Development of Resistance to Imatinib (STI571) in Two Leukemia Cell Lines Expressing p210 Bcr/Abl Protein," Cancer 100:1459-1471 (2004).
Talhout, R., et al., "Understanding Binding Affinity: A Combined Isothermal Titration Calorimetry/Molecular Dynamics Study of the Binding of a Series of Hydrophobically Modified Benzamidinium Chloride Inhibitors to Trypsin," J. Am. Chem. Soc. 125:10570-10579 (2003).
Wang, Z., et al., "SIRT1 Deacetylase Promotes Acquisition of Genetic Mutations for Drug Resistance in CML Cells," Oncogene 1-10 (2012) doi:10.1038/onc.2012.83.
"Exploring Roles of HIC1 and SIRT1 in Chemoresistance of Chronic Myelogenous Leukemia," abstract only, published on or about Jan. 27, 2006, accessed Jun. 28, 2012.

* cited by examiner

CATTCAACGGTGGCCGACGGGCTCATCACCACGCTCCATTATCCAGCCCCAAAG<u>CGCAACAAGCCC</u>
<u>ACTGTCTATGG</u>TGTGTCCCCCAACTACGACAAGTGGGAGATGGAACGCACGGACATCACCATGAA
 PcDNA →
GCACAAGCTGGGCGGGGGCCAGTACGGGGAGGTGTACGAGGGCGTGTGGAAGAAATACAGCCT
GACGGTGGCCGTGAAGACCTTGAAGGT//AGGAGGACACCATGGAGGTGGAAGAGTTCTTGAAAG
AAGCTGCAGTCATGAAAGAGATCAAACACCCTAACCTGGTGCAGCTCCTTGGTGAGTAAGCCCGG
GGCTCTGAAGAGAGGGTCTCGCGCCGCACCCCAGGGTGACACAGGCGCTGGGGAAGACGCACG
GGCGGCTCACTGCACAAAACCTCGTTGGAATATTTGTGCTCTGCCGACGTTCAGCCGCGGGTAAAAT
GAGGCCTGTATGGGATGGGTGTGTGCGTGTGTGCACATATGCACATGTATGTATGAGAGGGAGAAT
GTGATTATTTTAAGTGGATACCTAAAAGCAGTCAAATGCAAATCTGAAATTAGTTTCTGAAACTTGGG
CATTTTCCAGAGTTTTCTCACTGAAGTGATTCTGTAAGTAGACACATAACCATCAGACCTAACCATTCA
GGGGTAAACTGACGGTGGTGAAGGTCATTTGAGGTGGGGCCAGGTCTGCGTCTGAATTCTGTGGCA
GCCTCTCCCTGCGTAAATTCAAGTTCACTGGCTTGAGAAGAAGAAAAGAGCCTGGCCATGTCCCTCC
CACACGAGCACAGTCTCAGGATGCAGGTGCTTGGGACCATGTTGGAAGTTGGGCCCAGGACTGAG
GA<u>*GCAGAGTCAGAATCCTTCAG*</u>AAGGCTTTTTCTTTAGACAGTTGTTTGTTCAGTTGG
 PgDNA

GAGCG<u>*GAGCCACGTGTTGAAGTCCT*</u>CGTTGTCTTGTTGGCAGGGGTCTGCACCCGGGAGCCCCCG
  PgDNA
TTCTATATCATCACTGAGTTCATGACCTACGGGAACCTCCTGGACTACCTGAGGGAGTGCAACCG
GCAGGAGGTGAACGCCGTGGTGCTGCTGTACATGGCCACTCAGATCTCGTCAGCCATGGAGTACC
TGGAGAAGAAAAACTTCATCCACAGGTAGGGGCCTGGCCAGGCAGCCTGCGCCATGGAGTCACAG

GGCGTGGA<u>*GCCGGGCAGCCTTTTACAAA*</u>AAGCCCC//TCTTAGAGATCTTGCTGCCCGAAACTGCCT
  PgDNA
GGTAGGGGAGAACCACTTGGTGAAGGTAGCTGATTTTGGCCTGAGCAGGTTGATGACAGGGGAC
ACCTACACAGCCCATGCTGGAGCCAAGTTCCCCATCAAAT<u>GGACTGCACCCGAGAGCCTGGCC</u>TA
              PcDNA

CAACAAGTTCTCCATCAAGTCCGACGTCTGGGGTAAGGGCTGCTGCTGCACTGAAGTGGTCCTT

Figure 18

GCAGCAGGTACAGAGGCCCTGAGGCCTTTTATTGTGTCTTTTTGCTTGAGCGAGTA
ACTTAGAGCACACGTAGAGAAAGACAGCAGAAGTGATCTTCTAAACACTCTGTCCT
GTGTGGAGAGCTCCTTATGTGAGATTTTGCTGTGTAGTGAATTAAGGCTCAGCCAA
ACTGGCTCACGTGAGCTCTTTGAGCTT<u>GCCTGTCTCTGTGGGCTGAAGG</u>CTGTTC
CCTGTTTCCTTCAGCTCTACGTCTCCTCCGAGAGCCGCTTCAACACCCTGGCCGA
GTTGGTTCATCATCATTCAACGGTGGCCGACGGGCTCATCACCACGCTCCATTATC
CAGCCCCAAAGCGCAACAAGCCCACTGTCTATGGTGTGTCCCCCAACTACGACAA
GTGGGAGATGGAACGCACGGACATCACCATGAAGCACAAGCTGGGCGGGGGCCA
GTACGGGGAGGTGTACGAGGGCGTGTGGAAGAAATACAGCCTGACGGTGGCCGT
GAAGACCTTGAAGGTAGGCTGGGACTGCCGGGGGTGCCCAGGGTACGTGGGG<u>CA
AGGCGTCTGCTGGCATTA</u>GGCGATGCATCTGCCTGGAAGTCTACCTCCTGCCTGC
TGTCCGAGGGCTTCATTGGCGCCACGGAATTGACTTTTCCGTCTTATATCATTCCT
GTGTCTTTGTAGGAGTGGAATCATTCTCATAGTCCGAGTGTGTTTCCACATATGGT
GAGAGCTGACAAGCATGGAGGGGTTTTGGTGTAAAAAGATTAGTCATTTGGAGAG
GTTTTCTCATTTTATGGCAAGGTTCTTTTAAAGCCGTGGATTTCCATG

Forward: 5'-GCCTGTCTCTGTGGGCTGAAG-3'
Reverse: 5'-TAATGCCAGCAGACGCCTTG-3'

Figure 19

```
TCTTGCTGCGCCTCCGCCTCCTCCTCTGCTCCGCCACCGGCTTCCTCCTCCTGAGCAGTCAGCCCG
CGCGCCGGCCGGCTCCGTTATGGCGACCCGCAGCCCTGGCGTCGTGATTAGTGATGATGAACCAG
GTTATGACCTTGATTTATTTTGCATACCTAATCATTATGCTGAGGATTTGGAAAGGGTGTTTATTCCTC
ATGGACTAATTATGGACAGGACTGAACGTCTTGCTCGAGATGTGATGAAGGAGATGGGAGGCCATC
ACATTGTAGCCCTCTGTGTGCTCAAGGGGGGCTATAAATTCTTTGCTGACCTGCTGGATTACATCAAA
GCACTGAATAGAAATAGTGATAGATCCATTCCTATGACTGTAGATTTTATCAGACTGAAGAGCTATTG
TAATGACCAGTCAACAGGGGACATAAAAGTAATTGGTGGAGATGATCTCTCAACTTTAACTGGAAAGA
ATGTCTTGATTGTGGAAGATATAATTGACACTGGCAAAACAATGCAGACTTTGCTTTCCTTGGTCAGG
CAGTATAATCCAAAGATGGTCAAGGTCGCAAGCTTGCTGGTGAAAAGGACCCCACGAAGTGTTGGAT
ATAAGCCAGACTTTGTTGGATTTGAAATTCCAGACAAGTTTGTTGTAGGATATGCCCTTGACTATAAT
GAATACTTCAGGGATTTGAATCATGTTTGTGTCATTAGTGAAACTGGAAAAGCAAAATACAAAGCCTA
AGATGAGAGTTCAAGTTGAGTTTGGAAACATCTGGAGTCCTATTGACATCGCCAGTAAAATTATCAAT
GTTCTAGTTCTGTGGCCATCTGCTTAGTAGAGCTTTTTGCATGTATCTTCTAAGAATTTTATCTGTTTT
GTACTTTAGAAATGTCAGTTGCTGCATTCCTAAACTGTTTATTTGCACTATGAGCCTATAGACTATCAG
TTCCCTTTGGGCGGATTGTTGTTTAACTTGTAAATGAAAAAATTCTCTTAAACCACAGCACTATTGAGT
GAAACATTGAACTCATATCTGTAAGAAATAAAGAGAAGATATATTAGTTTTTTAATTGGTATTTTAATTT
TTATATATGCAGGAAAGAATAGAAGTGATTGAATATTGTTAATTATACCACCGTGTGTTAGAAAAGTAA
GAAGCAGTCAATTTTCACATCAAAGACAGCATCTAAGAAGTTTTGTTCTGTCCTGGAATTATTTTAGTA
GTGTTTCAGTAATGTTGACTGTATTTTCCAACTTGTTCAAATTATTACCAGTGAATCTTTGTCAGCAGT
TCCCTTTTAAATGCAAATCAATAAATTCCCAAAAATTT
```

METHODS OF TREATING CHEMORESISTANCE AND RELAPSE IN CANCER CELLS

PRIORITY CLAIM

This application claims the benefit of U.S. Provisional Patent Application Ser. No. 60/888,307, filed Feb. 5, 2007, which is incorporated herein by reference.

GOVERNMENT INTEREST

The present invention was supported by the Department of Defense (Grant No. W81XWH-06-1-0268). The government may have certain rights in the present invention.

FIELD OF THE INVENTION

The present invention relates to methods of treating and/or preventing chemoresistance and/or relapse in cells or a subject afflicted with cancer and research models of studying the same.

BACKGROUND

Epigenetic disruptions of gene expression such as by DNA methylation and histone modifications are profoundly involved in tumorigenesis. For leukemia, the gene hypermethylated in cancer 1 ("HIC1") is unique because hypermethylation of the gene's promoter region occurs progressively towards the late phases of hematologic malignancies. HIC1 encodes a DNA-binding, zinc finger transcriptional factor that is essential for mammalian development. The HIC1 gene is inactivated but not mutated in certain human cancers such as chronic myelogeneous leukemia (CML) and relapsed acute lymphocytic leukemias following chemotherapy. Using mouse genetics, the importance of HIC1 in of tumorigenesis has recently been demonstrated. Germline disruption of one copy of HIC1 predisposes mice to a late on-set and gender-dependent spectrum of malignant tumors wherein promoter hypermethylation of the wild type HIC1 allele is associated with loss of function of this gene. It is also known that HIC1 plays a synergistic role with p53 in suppressing the development of age-dependent cancers. Germline disruption of one copy each of HIC1 and p53 on opposite (trans) chromosomes or same (cis) chromosomes in mice results in altered tumor spectrum, earlier appearance and increased prevalence and aggressiveness of osteosarcomas. Indeed, a low frequency of blast crisis megakaryocytic leukemia is found in cis HIC1 and p53 double heterozygous mice.

A key mechanism by which HIC1 suppresses tumorigenesis is through its regulation of the stress and DNA damage responsive gene, SIRT. SIRT1 is a mammalian orthologue of yeast silent information regulator 2 (Sir2) that is required for yeast lifespan extension upon calorie restriction. An extra copy of Sir2 extends life span in yeast, fly and worm. SIRT1 is a class III histone deacetylase whose enzymatic activity is dependent on cofactor NAD. SIRT1 is insensitive to histone deacetylase inhibitor trichostatin A (TSA) which inhibits class I and II deacetylases. The mammalian SIRT1 maintains cell survival during stress and DNA damage through multiple pathways, one of which includes the deacetylation of p53 and attenuation of its ability to activate downstream targets to control apoptosis. HIC1 forms a complex with SIRT1 protein. This HIC1/SIRT1 protein complex directly binds to the SIRT1 promoter in vivo to repress SIRT1 gene transcription. Loss of HIC1 expression by promoter hypermethylation upregulates SIRT1 in cancer cells, attenuates p53 activity by deacetylation and allows cells to bypass apoptosis and survive stress and DNA damage. Inhibition of SIRT1 function in cells without HIC1 abolishes the resistance to apoptosis.

Chronic myelogenous leukemia is a fatal hematopoietic disorder resulting from malignant transformation of bone marrow progenitor cells. The disease progresses from chronic phase, to accelerated phase to terminal blast crisis phase. CML is characterized by a reciprocal translocation of chromosome 9 and 22 that creates an oncogenic fusion gene, BCR-ABL. This gene produces a protein with deregulated BCR-ABL tyrosine kinase activity. Imatinib mesylate (also known as imitanib, Gleevac or STI-571) is a potent ABL tyrosine kinase inhibitor. In most chronic phase patients, treatment with imatinib results in major and complete hematologic responses and infrequent relapse. However, in most blast crisis patients, there is a poor response to imatinib treatment and a high frequency of relapse in those patients having an initial response. The molecular mechanisms of the resistance to imatinib may consist of both BCR-ABL dependent and independent pathways. BCR-ABL dependent pathways are characterized by genetic alterations of the BCR-ABL gene.

The clinical resistance to imatinib treatment is mediated primarily by genetic mutations of the BCR-ABL kinase domain, and to a lesser extent, by amplification of the BCR-ABL gene. In relapsed CML patients, more than 15 BCR-ABL mutations have been identified. These mutations confer various degrees of resistance to imatinib. Mechanisms for formation of BCR-ABL mutations in CML are not clear. The vast majority of BCR-ABL mutations are detected in relapsed patients, but pre-existing mutations including a T315I mutation are also found in patients before imatinib treatment (Gorre et al., 2001; Shah et al., 2002). The T315I mutation has been identified thus far as being the most frequent and powerful mutation. Located in the center of the imatinib binding site is $Thr^{315}$ and the T315I mutation blocks the drug from binding to the ABL kinase. In vitro studies of the process by which BCR-ABL is mutated in CML cells is difficult because, unlike what occurs in vivo, nearly all CML cell lines derived from blast crisis CML are sensitive to 1 µM STI-571 treatment. (Deininger et al., 1997). Nilotinib (AMN107) is a recently developed BCR-ABL inhibitor having greater potency. It inhibits most of the known mutants with the exception of the T315I mutation. Similarly, the potent dual SRC-ABL kinase inhibitor dasatinib (BMS-354825) inhibits 14 of 15 BCR-ABL mutants but not T315I. However, in vivo, CML patients with a T315I mutation do not respond to either nilotinib or dasatinib. Without further effective treatment, these blast crisis patients are terminal. Accordingly, a method of treating these relapsed patients or preventing formation of this resistant mutation is highly desired.

Several resistant CML cell lines have been developed by gradually exposing cells to increasing concentrations of STI-571. (Mahon et al., 2000). However, these resistant cell lines all have BCR-ABL gene amplification but lack mutations. This is opposite to the results seen in patients. Today, most in vitro mutation studies are carried out using murine cell lines such as Ba/F3 cells, a murine pro-B cell line transfected with genetically engineered BCR-ABL mutations. (La Rosee et al., 2002; Shah et al., 2004; von Bubnoff et al., 2006; von Bubnoff et al., 2005; Weisberg et al., 2005). Although these cell lines are important for addressing mutant kinase activity, they do not reflect in vivo mechanisms of BCR-ABL mutagenesis, and thereby cannot be use to address mechanisms of BCR-ABL mutagenesis in natural cellular and molecular contexts of CML, and cannot be applied to development of strategies for preventing such mutations. The use of these cells also excludes the possibility of studying other genetic and epigenetic alterations accompanying the BCR-ABL mutagenesis process in mutant CML cells. Thus, a CML cell line having one or more BCR-ABL mutations is also highly desired because it is useful as a model system for CML disease. Use of such cell lines will facilitate further study of the mechanism of disease development and progression and assist in the further identification of therapeutic treatments for this disease.

SUMMARY

Methods of treating or preventing BCR-ABL drug resistance in chronic myelogenous leukemia (CML) comprise administering a therapeutically effective amount of one or more SIRT1 modulators to the cells or subject in need thereof. Thus, in one aspect, the invention provides a method of inhibiting growth of a tumor cell. If the tumor cell is a leukemia cell, it may be chronic myelogenous leukemia, acute myelogenous leukemia, chronic lymphocytic leukemia, acute lymphocytic leukemia, or hairy cell leukemia. In another aspect, the invention provides a method of inhibiting relapse growth of cancer cells or preventing chemoresistance. This method comprises use of a modulator of SIRT1 such as a SIRT1 inhibitor. A modulator includes inhibitors of SIRT1 protein, inhibitors of the SIRT1 gene (transcription or translation inhibition, or both). A SIRT1 inhibitor may be a napthol compound (for example, sirtinol or splitomicin), an indole, siRNA, a derivative of a SIRT1 inhibitor, an analogue of a SIRT1 inhibitor or any combination thereof. Chemoresistance, such as BCR-ABL drug resistance, may be caused by administration of a cancer treating drug such as STI-571 (imatinib), nilotinib, dasatinib, or another cancer treating drug. Alternatively, drug resistance may be caused by another drug or compound administered to the patient, environmental factors, or may be a naturally occurring resistance. The drug resistance may be the result of a genetic mutation such as the T315I mutation of the BCR-ABL gene. The SIRT1 inhibitor may also treat or prevent insulin and transferrin-induced resistance.

Additionally, a method for making a model of acquired resistance in human cancers which simulates a patient's chemoresistance response is provided. Such a method allows for the study of mechanisms involved in the development of acquired resistance such as through induction of genetic mutations of oncogenic tyrosine kinases as well as through alteration of DNA damage response pathways. Cell line models are also provided. Use of these model systems allow for the screening, identification, testing and discovery of therapeutic compounds useful for treating cancer and especially cancer relapse from chemoresistant cell growth.

A novel CML resistance model using naïve blast crisis CML cells is also provided. Using this model, key features of clinical resistance such as rapid growth of cancer cells after direct exposure of the cancer cells to therapeutically effective concentrations of chemotherapeutic compounds can be replicated. Cancer cells which survive chemotherapeutic treatment (also referred to herein as "relapse" growth) exhibit genetic mutations at the BCR-ABL locus. This model will serve as a useful system for designing, testing, screening and identifying new therapeutic strategies for treating chemoresistant cancer. The methods provided herein are also useful for developing cell culture models of acquired resistance in solid tumors such as non-small cell lung carcinomas. Over active SIRT1 pathway is a mechanism by which acquired resistance develops in hematologic as well as solid tumors. The present invention provides treatment and diagnostic modalities based upon this discovery.

BRIEF DESCRIPTION OF THE DRAWINGS

In FIG. 1(A), the triangle is germline deletion of HIC1, the asterisk is HIC1 promoter hypermethylation, and the rectangle represents somatic HIC1 deletion. FIG. 1(B) shows how HIC1 inactivation is mediated by promoter hypermethylation in trans HIC1+/−p53+/−mice, but genetic deletion in cis mice. Interstitial chromosomal deletion between 20 and 66 cM occurs after loss of wild type p53 in trans tumors, but the entire chromosome harboring wild type p53 and HIC1 is deleted in cis tumors. The diamond and triangle are germline deletion of p53 and HIC1, respectively; the asterisk is HIC1 promoter hypermethylation, and the rectangle is somatic p53 deletion.

FIG. 2(A) shows mouse SIRT1 protein level in MEF nuclear extract from HIC1, LSH or INK4a locus knock-out. The numbers underneath Western blots are relative SIRT1 levels normalized to lamins. FIG. 2(B) shows SIRT1 RNA levels in HIC1 knockout MEF by Northern blot. 18S RNA was used as a loading control. The numbers underneath the SIRT1 blot are relative SIRT1 levels normalized to 18S RNA. FIG. 2(C) shows over-expression of HIC1, but not lacZ or mutant HIC1, repressed nuclear SIRT1 in breast cancer MCF-7 cells. FIG. 2(D) shows luciferase reporter assay of SIRT1 promoter. A DNA fragment covering the entire SIRT1 promoter CpG island (from −1231 to +900) was isolated to drive luciferase expression in a pGL2 vector. The luciferase activity was assayed in COS-7 cells with expression of the constructs and infection with recombinant adenoviral vectors as shown. FIG. 2(E) shows ChIP assay with HIC1 and SIRT1 on the SIRT1 promoter using HIC1-expressing WI38 cells. Two HIC1 binding sites (−1116 and −1039 in the same orientation), as indicated by wide arrows, are located 5' to the promoter CpG island, and the other two (+575 and +660) in the opposite orientation to one another are located inside intron 1 towards the 3' end of the island. ChIP was performed with HIC1 polyclonal antibody or SIRT1 monoclonal antibody, and both 5' and 3' binding regions were examined by multiplex PCR with GAPDH as an internal non-binding control. CTL (R), normal rabbit IgG control; CTL (M), normal mouse IgG control. The triangles indicate increasing amount of HIC1 or SIRT1 antibodies. FIG. 2(F) shows ChIP upon ChIP assay for 5' HIC1 binding sites on SIRT1 promoter. Sonicated WI38 cell chromatin was first immunoprecipitated with rabbit HIC1 antibody and the eluted product was re-immunoprecipitated with mouse SIRT1 antibody (HIC1, SIRT1). For control, normal rabbit IgG was used for the first round of immunoprecipitation and normal mouse IgG for the second (CTL(R, M)). ChIP upon ChIP was also performed with a reverse order of immunoprecipitation, namely SIRT1 ChIP, first, followed by HIC1 ChIP (SIRT1, HIC1); or control mouse IgG followed by rabbit IgG (CTL (M, R)). PCR amplification of 5' HIC1 binding sites was carried out as in panel E. (Chen, et al 20005, Cell 123, 437-448.).

FIG. 16(A) shows structure of Aurora A kinase. Destruction box (D box, in black) and A box (dark grey) are required for degradation of Aurora A during cell cycle. The kinase domain is in light grey. FIG. 16(B) shows expression of Aurora A and B in KCL-22 and KCL-22M cells following two days of drug treatment.

FIG. 18 shows the BCR-ABL kinase domain sequence with the identified mutations as indicated [SEQ ID NO: 1]. Bold text represents exons and regular text represents introns. The primers for sequencing cDNA (PcDNAt) are underlined [SEQ ID NOS:5 & 6]. The primers for sequencing genomic templates (PgDNA) are underlined and in italic text [SEQ ID NOS: 7-9]. The 579-bp kinase domain is located between the two PgDNA primers. Mutation sites are indicated in large font. Accession information: >gi|71648777|gb|DQ145721.1| Homo sapiens v-abl Abelson murine leukemia viral oncogene homolog 1 (ABL1) gene, complete cds.

FIG. 19 shows additional primers for BCR-ABL kinase domain sequencing: Two primers for sequencing genomic templates for E255 [SEQ ID NO:3] and Y253 [SEQ ID NO: 4] mutations are located at introns and are indicated in underlined text. Additional primers for BCR-ABL kinase domain sequencing: >gi|71648777|gb|DQ145721.1| [SEQ ID NOS: 10 & 11].

FIG. 20 shows the HPRT sequence [SEQ ID NO: 12]. Sequence corresponding to sequencing primers is underlined [SEQ ID NOS: 13 & 14]. Start and stop codons are in bold text. Accession information: >gi|4504482|ref |NM_000194.1| Homo sapiens hypoxanthine phosphoribosyltransferase 1 (Lesch-Nyhan syndrome) (HPRT1), mRNA.

DETAILED DESCRIPTION

Figure 1:
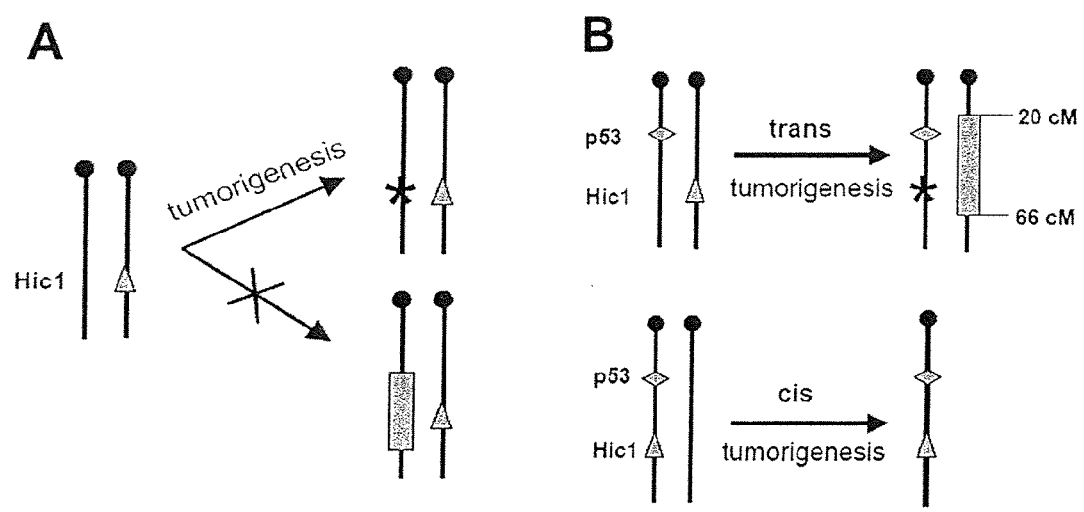
FIG. 1 illustrates roles of HIC1 in tumor suppression. In tumors from HIC1$^{+/-}$ mice, HIC1 inactivation is mediated by promoter hypermethylation but not genetic deletion.
Figure 2:
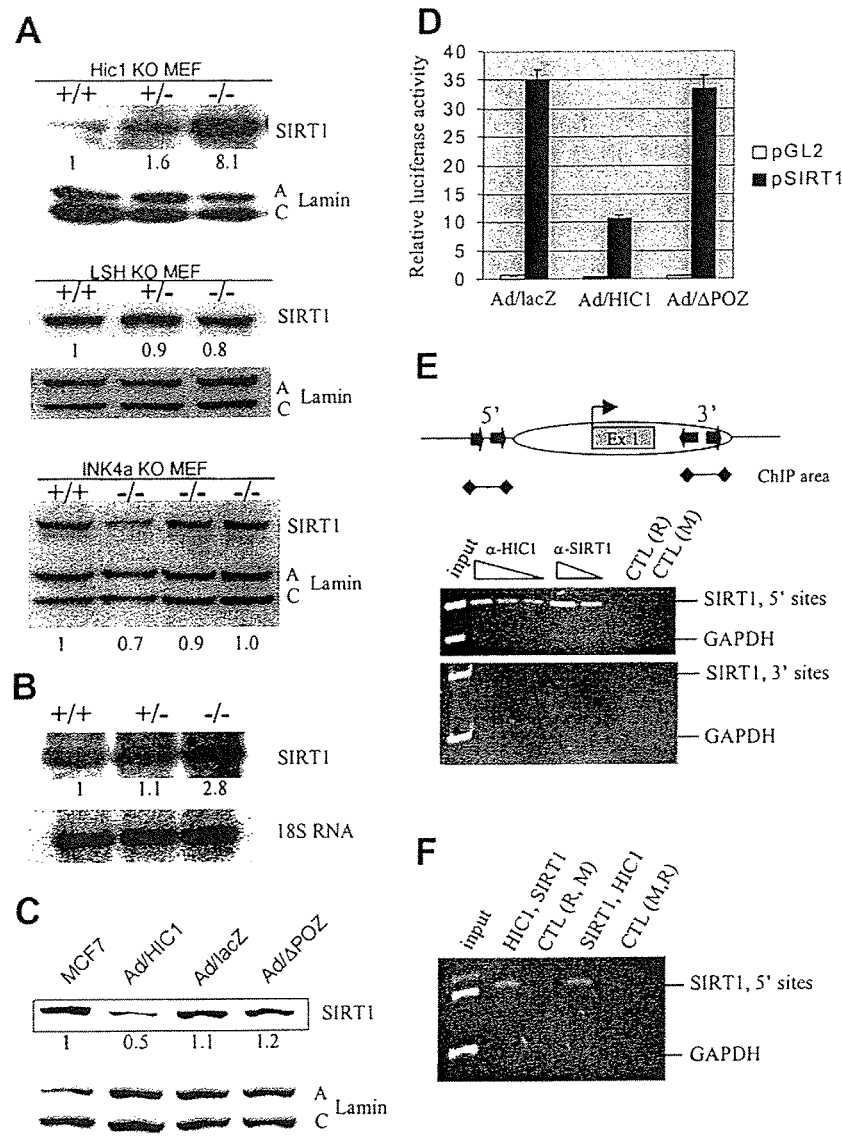
FIG. 2 shows how HIC1 directly regulates SIRT1 transcription.

The presently disclosed methods and models are not limited to the particular configurations, process steps, and materials disclosed herein as such configurations, process steps, and materials may vary without materially varying from the scope and spirit. It is also to be understood that the terminology employed herein is used for the purpose of describing particular embodiments only and is not intended to be limiting. The examples are intended only to illustrate the invention, and are not meant as limitations on it. All references referred to herein are incorporated by reference in their entirety.

Definitions

"Agonist" refers to a ligand that interacts with or binds to its receptor to up-regulate, accelerate, or activate the activity of a compound, receptor, gene, or protein.

"Antagonist" refers to a ligand that interacts with or binds to its receptor to downregulate, suppress, or inhibit the activity of a compound, receptor, gene, or protein.

"Antisense molecule" refers to a nucleic acid molecule that hybridizes to all or a portion of a target gene or all or a portion of an mRNA encoded by a target gene. Hybridization of an antisense molecule to a target gene or a portion thereof may inhibit expression of the target gene by inhibiting transcription of the gene sequence, while hybridization of an antisense molecule to a transcript encoded by a target gene may inhibit expression of the target gene by inhibiting translation of the transcript into a polypeptide sequence.

"Cell culture" refers to a cell strain or a cell line.

"Chemotherapeutic agent" refers to any chemical compound or treatment method that induces cell damage, results in cell death, or both. Specific chemotherapeutic agents include but are not limited to kinase inhibitors such as tyrosine kinase inhibitors (TKI), which include, imatinib, gefitinib, erlotinib, lapatinib, CI-1033, PKI-166, GW-2016, as well as others that will be known to one of ordinary skill in the art. Other chemotherapeutic agents include imatiactinomycin-D, adriamycin, androgens, asparagine, azathioprine, BCG, bleomycin, camptothecin, cisplatin, epirubicin, etoposide, gemcitabine, hydroxyurea, interferon alpha, interferon beta, interferon gamma, mitomycin C, paclitaxel, thioguanine, 5-fluorouracil, 6-mercaptopurine, or other drugs. In addition, "chemotherapeutic agent" may refer to radiation and waves, such as electroemissions, gamma radiation, microwaves, UV-irradiation, or X-rays. Other chemotherapeutic agents may include natural or synthetic antibodies, tyrosine kinase inhibitors, enzymatic inhibitors, growth factor inhibitors, metastases-inhibiting compounds, or oncogenic protein inhibitors, such as compounds that inhibit RAS, protein kinase, or DNA topoisomerase.

"SIRT1 inhibitor" refers to one or more compound that inhibits SIRT1 activity. Such inhibition includes direct as well as indirect inhibition of SIRT1 activity. Exemplary SIRT1 inhibitors include, but are not limited to, one or more agent or compound which results in inhibition of SIRT1 function, inhibition of expression of SIRT1 protein, inhibition of transcription or translation of the SIRT1 gene, or both. For example, a SIRT1 inhibitor includes sirtinol as well as its derivatives and other small molecule compounds able to reduce or inhibit SIRT1 activity. SIrt1 inhibitors include sirtinol, a sirtinol analogue or derivative, splitomicin, a splitomicin analogue, napthol, a napthol derivative, an indole, an indole derivative, siRNA, shRNA, antisense RNA, or any combination thereof.

"Duration" refers to the amount of time a desired gene is expressed, and may be measured, for example, in months, weeks, days, hours, minutes and/or seconds. "Inhibit" with regards to an activity means to suppress the activity, either by decreasing the level or rate of the activity, blocking or preventing the activity entirely, or preventing an increase in the activity under conditions in which the activity would normally be increased.

"In combination with" refers to two or more substances being administered simultaneously or in series close enough in time to bring about a therapeutically effective result.

"Leukemic disorder" refers to a cancerous disorder of blood forming tissues (e.g., spleen, bone marrow, lymphatics, liver) characterized by excessive leukocyte production. The term encompasses myeloid leukemias such as, for example, acute myeloid leukemia (AML), chronic myeloid leukemia (CML), and various subtypes thereof, and lymphocytic leukemias such as, for example, acute lymphocytic leukemia (ALL), chronic lymphocytic leukemia (CLL), hairy cell leukemia (HCL), and various subtypes thereof.

"Pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

"Polynucleotide" refers to any polyribonucleotide, polydeoxyribonucleotide, or hybrid polyribo-polydeoxyribonucleotide, including naturally occurring polynucleotides, synthetic polynucleotides, or any chemically, enzymatically, or metabolically modified forms of naturally occurring polynucleotides. The term encompasses both single- and double-stranded molecules, including DNA-DNA, DNA-RNA, or RNA-RNA duplexes, as well as molecules that are a mixture of single- and double-stranded regions. "Polynucleotide" also refers to triple-stranded molecules comprising DNA, RNA, or both DNA and RNA. Polynucleotides may contain any of the standard pyrimidine or purine bases (i.e., adenine, guanine, cytosine, thymine, uracil), as well as any modified or uncommon bases such as tritylated bases or inosine. In addition, the backbone of a polynucleotide may be modified for stability or for other reasons. "Polynucleotides" also refers to relatively short polynucleotides, often referred to as oligonucleotides, and to peptide nucleic acids (PNAs) formed by conjugating bases to a peptide backbone.

"Prodrug" as used herein refers to a derivative of a pharmaceutically or therapeutically active drug that is transformed into the active drug by an enzymatic or chemical process. Prodrugs may be developed to alter the metabolic stability or transport characteristics of a drug, to mask side effects or toxicity of a drug, or to improve or alter other characteristics of the drug. See, for example, Notari, R. E. 1985. Theory and practice of prodrug kinetics. Methods Enzymol 112:309-323; Bodor, N. 1981. Novel approaches in prodrug design. Drugs of the Future 6:165-182; Bundgaard, H. 1985, "Design of prodrugs: bioreversible derivatives for various functional groups and chemical entities," Chap. 1 in Design of Prodrugs, H. Bundgaard, Ed., Elsevier, N.Y., 1985.

"RNA interference" (RNAi) refers to a post-transcriptional gene silencing (PGSR) process whereby one or more exogenous small interfering RNA (siRNA) molecules are used to silence expression of a target gene.

"siRNAs" (short interfering RNAs) are double-stranded RNA molecules, generally around 15-30 nucleotides in length, that are complementary to the sequence of the mRNA molecule transcribed from a target gene. Following introduction into a cell, the siRNA molecule associates with one or more cellular proteins to form a siRNA/protein complex (RISC), which then binds to the mRNA transcript of the target gene. RISC binding results in degradation of the mRNA molecule, thereby preventing translation.

"shRNAs" (small hairpin RNAs) are short "hairpin-turned" RNA sequences that may be used to inhibit or suppress gene expression.

"Subject" refers to any animal, including a human, having a cell that may be treated by the methods or products discovered or tested by the methods of this disclosure.

"Route of administration" may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

"Therapeutically effective amount" is an amount of a compound that produces a desired therapeutic effect in a subject, such as preventing or treating a target condition or alleviating symptoms associated with the condition. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21st Edition, Univ. of Sciences in Philadelphia (USIP), Lippincott Williams & Wilkins, Philadelphia, Pa., 2005.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

Embodiments

Methods for treating or preventing cancer cell growth, treating or preventing resistance of a cancer cell to chemotherapy, or treating or preventing the relapse growth of one or more cancer cell are provided. The cancer cell is usually a hematologic disorder or a solid tumor. Commonly, the hematologic disorder is chronic myelogenous leukemia (CML). An exemplary cancer cell associated with a solid tumor is non-small cell lung carcinoma (NSCLC). A therapeutically effective amount of a SIRT1 modulator or a combination of multiple SIRT1 modulators is administered to a subject in need thereof. Frequently, a therapeutically effective amount of a modulator such as a SIRT1 inhibitor is administered. A SIRT1 inhibitor includes one or more inhibitors of sirtuins (class III histone/protein deacetylases), such as sirtinol or its analogue, which is administered in combination with the chemotherapeutic agent. Generally, the SIRT1 modulator is administered at or about the same time as the chemotherapeutic agent, but can also, if desired, be administered prior to or subsequent to the administration of the chemotherapeutic agent. The SIRT1 modulator may either be an agonist or antagonist of SIRT1 and may be any molecule, compound or agent that acts to modulate SIRT1. Such modulators include, but are not limited to, derivatives, analogues, small molecules, decoy molecules, drugs or prodrugs, polynucleotides, particularly antisense molecules and RNA interference using siRNA, shRNA, polypeptides, antibodies, including chimeric antibodies, or any other substance that acts on SIRT1 in an intended manner. If the SIRT1 modulator is a SIRT1 antagonist, acting to inhibit SIRT1, the inhibitor is preferably a napthol compound (for example, sirtinol or splitomicin), EX-527, an indole or its derivative, siRNA, shRNA, or any combination thereof.

Drug resistance or cancer cell relapse may be caused by administration of a chemotherapeutic agent such as imatinib, gefitinib, nilotinib, dasatinib, or another cancer-treating drug. Imatinib is a tyrosine kinase inhibitor. It interferes with BCR-ABL protein function. Gefinitib inhibits EGFR kinase. BCR-ABL drug resistance may be caused by administration of a chemotherapeutic agent such as imatinib, nilotinib, dasatinib, VX-680 (a dual Aurora kinase and BCR-ABL inhibitor) or another cancer-treating drug. Alternatively, resistance may be caused by another drug or compound administered to the patient, environmental factors, or may be a naturally occurring resistance. Relapse in chronic myeloid leukemia patients treated with imatinib, such as STI-571, is an example of one form of clinical chemoresistance associated with a point mutation or amplification of the BCR-ABL gene. Thus, the SIRT1 modular may also be administered in conjunction with a tyrosine kinase inhibitor.

Both the SIRT1 modulator and the chemotherapeutic agent are to be applied in therapeutically effective amounts and for any duration necessary to treat the cancer or prevent relapse of the cancer. A clinician can gauge the dosages for each required by the subject using known methods of optimizing drug performance and delivery by taking into account clinical data regarding tolerances, age, gender, severity of the disease, health of the subject, and the like. Preferably, the SIRT1 modulator is an inhibitor that is administered to the subject in a pharmaceutically acceptable carrier. The route of administration may be any route effective to carry the therapeutic SIRT1 modulator to the cancer cells in the subject, including any of the routes discussed above. In addition, the SIRT1 modulator may also be used treat or prevent insulin and transferrin-induced resistance as well as EGFR (epidermal growth factor receptor) associated resistance.

A method of preventing chemoresistance in CML cells comprising administering a therapeutic drug or combination of therapeutic drugs that prevent formation of a T315I mutation and other BCR-ABL mutations is also provided. These BCR-ABL mutations in cancer cells, particularly, CML cells are responsible for anti-apoptotic activity and, as such, prevent the cancerous cells from responding to traditional chemotherapy, radiotherapy, or other cytotoxic agents. Preferably, the therapeutic drug is comprises a SIRT1 antagonist, such as sirtinol, a sirtinol analogue, splitomicin, an indole, siRNA, shRNA, Aurora kinase inhibitor, or any combination thereof.

Another embodiment improves the efficacy of a cytotoxic agent directed to CML cells, in a subject, by administering to the subject at least one cytotoxic agent directed to CML cells, and administering to the subject a SIRT1 inhibitor in a therapeutically effective amount, so that the SIRT1 inhibitor enhances the efficacy of the cytotoxic agent relative to the effect of the cytotoxic agent in the absence of the SIRT1 inhibitor. The cytotoxic agent may be a BCR-ABL inhibitor, such as STI-571, imatinib, nilotinib, or dasatinib, or any combination thereof and the SIRT1 inhibitor is siRNA, a napthol compound, sirtinol, splitomicin, an indole, or any combination thereof. This method also treats or prevents insulin and transferrin-induced resistance. The methods of the present invention may be performed on any animal with cancer or CML, but are preferably for humans.

A novel tissue culture model to study mechanisms of BCR-ABL drug resistance is also provided, which simulates a subject's responses to chemotherapeutic treatment, such as to STI-571 treatment. Blast crisis CML cell line KCL-22 is refractory to treatment with 1 µM imatinib (Deininger et al., 1997). By treating KCL-22 cells with therapeutically effective doses of imatinib, while apoptosis of the KCL-22 cells was induced, relapse occurs in two weeks with development of T315I BCR-ABL mutation. Following the initial apoptosis upon STI-571 treatment with dosages equivalent to that found in human plasma, the KCL-22 cells developed the T315I mutation of the BCR-ABL kinase domain at high frequency in two weeks. However, when small molecule inhibitors of SIRT1 were used in combination with STI-571, the BCR-ABL mutation was prevented and CML cells were eliminated without relapse. These results demonstrate T315I mutation can be rapidly induced by Imatinib treatment but is preventable.

The method of screening for a candidate SIRT1 inhibitor for reducing chemoresistance or relapse in a cancer cell culture can be broadly applied and has the following steps. First, a base level of chemoresistance or relapse is established in a cancer cell culture, such as a cancer cell line, after administration of one or more chemotherapeutic agents by treating the cancer cell culture with the chemotherapeutic agent under conditions which induce chemoresistance or relapse in the cell culture. Then, the candidate SIRT1 inhibitor is administered to previously untreated cells of the cell culture before, during, and/or after administering the one or more chemotherapeutic agents. Finally, the level of chemoresistant or relapsed cells after treatment with the candidate SIRT1 inhibitor and the chemotherapeutic drug is measured. A reduction or absence of chemoresistant or relapsed cells as compared to base level of chemoresistance or relapse established at the outset of the model indicates that the compound is a SIRT1 inhibitor.

Therefore, the culture system developed provides, among other things, the first in vitro system of its kind to study mechanisms of BCR-ABL mutagenesis in the natural molecular and cellular contexts of CML. The methods and system provided herein can be used to develop strategies to treat and prevent formation of such a mutation. The discovery that SIRT1 inhibitors can block T315I mutation and completely eliminate CML cells when administered with imatinib also provides a novel treatment modality for CML patients. In addition, the T315I mutant cells generated from this system also provide invaluable tools for studying mechanisms of resistance after mutation and strategies to eradicate these highly resistant cells.

Using this model, key features of clinical resistance such as rapid relapse through BCR-ABL mutations after imatinib treatment can be replicated. This model will serve as a system for designing, testing, screening and identifying new therapeutic strategies for treating CML. For example, the resistance model can be used to screen modulators of enzymatic activity or small molecule inhibitors such as those which inhibit SIRT1, chemotherapeutics, compounds, or anti-cancer modalities having therapeutic efficacy or those able to inhibit BCR-ABL mutation based resistance. The resistance model may also be used for further studies of resistance mechanisms, which will allow for the design of new therapeutic strategies, such as use of small molecule inhibitors to prevent the induction of those mutations that accompany a cancer drug treatment, The novel tissue culture method provided herein closely simulates in vivo CML relapse on imatinib treatment using KCL-22 cells. By direct exposure of cells to Imatinib with concentrations pertinent to those in patient plasma, the T315I mutation of BCR-ABL can be induced rapidly with high frequency. The resultant T315I mutant cells differ from parental KCL-22 cells in size, morphology and cell cycle, and they are highly resistant to various treatments. SF medium or supplying insulin in serum medium will also provide CML cells resistance to Imatinib treatment. Finally, the combination of Imatinib with SIRT1 inhibitors will prevent CML relapse and abolish growth-factor-induced resistance. Thus, the methods outlined herein provide a platform for studying strategies for preventing formation of such a mutation and screening for small molecule inhibitors for blocking CML relapse.

The present invention also includes the discovery of a novel mechanism for acquired resistance through active induction of genetic mutations of oncogenic tyrosine kinases in human cancer. SIRT1 is a key gene for controlling active induction of genetic mutations on tyrosine kinases through altering DNA damage pathways. Inhibitors of SIRT1 will inhibit acquired resistance through prevention of genetic mutations, and thus are especially useful in the clinical setting where combination cancer therapeutics are applicable or utilized. The present invention, however, is not limited to CML. Rather, as is understood by a person of ordinary skill in the art, the mechanisms of acquired resistance and functions of SIRT1 and its inhibitors described herein can also be applied to treatment of acquired resistance in other cancers.

Clonal cells derived from parental KCL-22 cells also predominantly develop resistance to imatinib by BCR-ABL mutations including the T315I [SEQ ID NO: 2], E255K [SEQ ID NO: 3] and Y253H [SEQ ID NO: 3] [SEQ ID NO: 4] mutations. The mutations exhibited by the clonal cells recapitulate the most frequently observed mutations in CML patients (Shah et al., 2002; Soverini et al., 2006). Furthermore, the rapid relapse is similar to that seen in blast crisis patients. The ability to form BCR-ABL mutations in clonal cells indicates that pre-existing rare mutant cells from the original patient are not required for development of resistance. The BCR-ABL mutation frequency varies among clones while HPRT mutation frequency remains relatively constant. Unlike the broad mutation spectrum of HPRT observed in parental or clonal cells, BCR-ABL mutations may be limited to one mutation in a parental cell or a clone. Additionally, while the spontaneous mutation frequency of HPRT remains relatively constant throughout cell passages, frequency of BCR-ABL mutation declines in later passages. The data provided herein indicate that BCR-ABL mutations upon imatinib treatment are not always derived from random DNA replication error during clonal expansion or cell propagation, but are actively induced by imatinib treatment. The invention includes a novel model system for testing and identifying therapeutic modalities and compounds for treating CML. The invention includes systems, methods and cell lines based on the discovery that the targeting of a tyrosine kinase (as an anti-cancer treatment) may in itself be mutagenic and thereby induce DNA mutations thereby directly or indirectly contributing to clinical acquired chemoresistance.

EXAMPLES

The following examples are put forth so as to provide those of ordinary skill in the art exemplary descriptions of how to make and use the methods and compositions of the invention, and are not intended to limit the scope of the invention.

Example 1

An in vitro model of CML chemoresistance. CML cell lines KCL-22 and K562 were purchased from German Collection of Cell Cultures, Braunschweig, Germany, and grown in RPMI 1640 medium with 10% fetal bovine serum (Hyclone). STI-571 was provided by Novartis, Basel, Switzerland. Sirtinol, splitomicin, nicotinamide, trichostatin A and 5-aza-2-deoxycytidine were purchased from Sigma. For serum-free culture, basic supplements (ITS I-1884), EGF and HDL were purchased from Sigma and insulin from Roche.

In contrast to the in vivo resistance observed in blast crisis CML patients treated with STI-571, CML cell lines derived from blast crisis patients are sensitive to STI-571 treatment. STI-571 at 1 μM selectively kills CML cells in BCR-ABL dependent manner with the exception of KCL-22 cells, whereas 10 μM STI-571 results in cell death independent of BCR-ABL. In chronic phase CML patients, STI-571 is given at 400 mg/day that produces the average peak plasma concentration at 4.4 μM and trough concentration at 2.0 μM. For blast crisis patients, STI-571 dosage is increased to 600 mg/day. Therefore, effects of imatinib concentrations at 1, 2.5, 5 and 10 μM were examined on the survival of KCL-22 cells during prolonged culture.

$5 \times 10^5$ KCL-22 or K562 cells were seeded in 1 ml medium per well in 24-well plates, and treated with various combinations of drugs. Cells were maintained in these cultures without changing medium. Aliquots of cells were taken out at specified time points and cell numbers counted using a hematocytometer. Cell viability was accessed by trypan blue exclusion where necessary. Typically, after three to five weeks in culture when medium volume significantly decreased, fresh drug-free medium was supplied to the cells to restore the wells to the original volume for prolonged culture.

Figure 3:
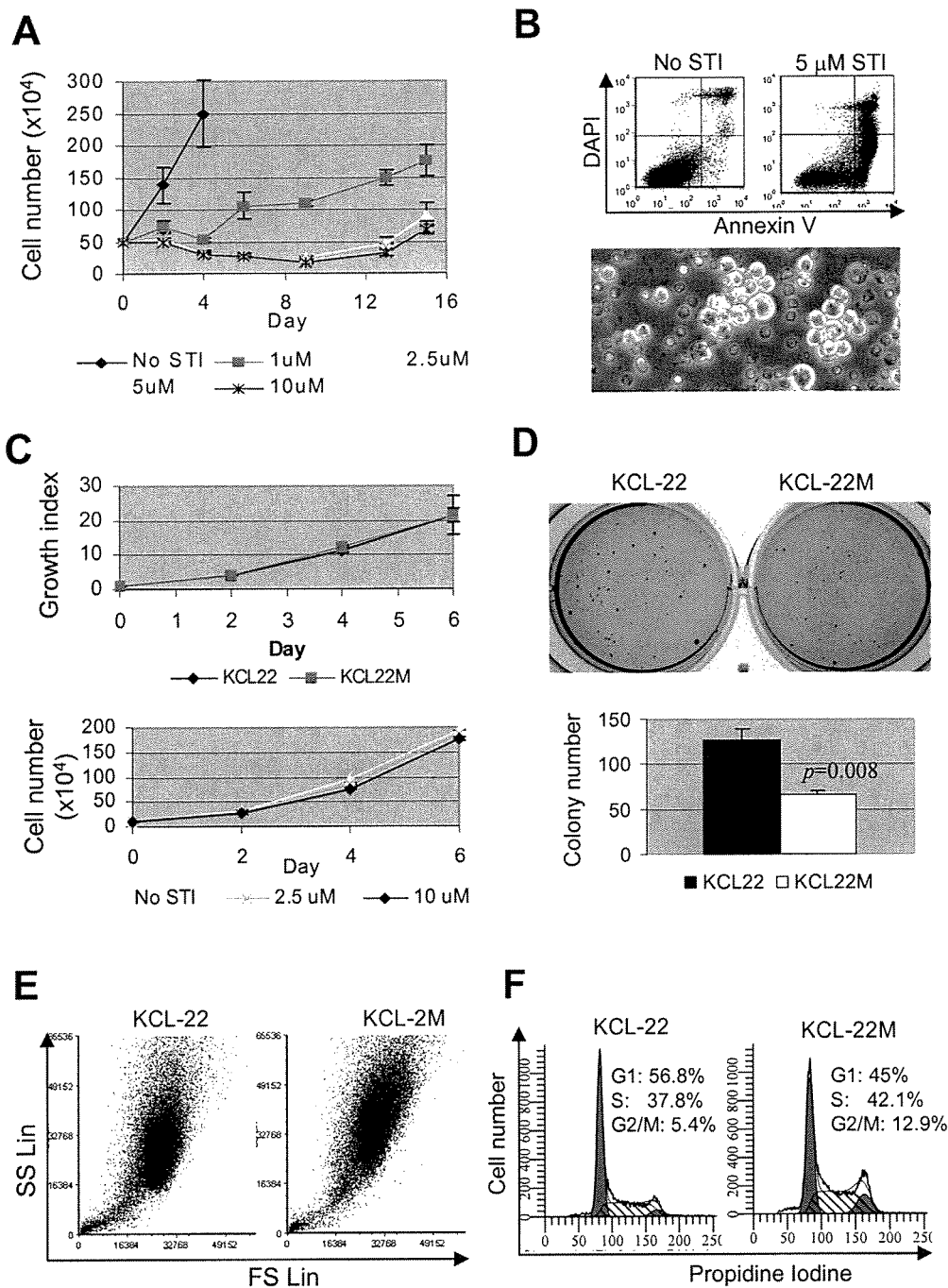
FIG. 3 shows a model of CML acquired resistance. (A) KCL-22 cells treated with 1, 2.5, 5, and 10 μM imatinib (STI). Relapse on 2.5 μM and higher concentrations of imatinib two weeks post treatment. (B) Top: apoptosis of KCL-22 cells after treatment with imatinib was analyzed by annexin V staining. Bottom: formation of clusters of resistant cells (light) among scattered dead cells (dark). (C) Top: growth curves for resistant cells (KCL-22M) and KCL-22 cells analyzed by XTT. Growth indexes were relative XTT readings normalized to the initial XTT readings at day 0. Bottom: comparison of growth of KCL-22M cells in the absence and presence of imatinib. (D) Soft agar colony formation of KCL-22 and KCL-22M cells. (E) Comparison of cell size and complexity of KCL-22 and KCL-22M cells. KCL-22M cells exhibited increase at both forward scatter (FS) and side scatter (SC) parameters. (F) Comparison of cell cycle of KCL-22 and KCL-22M cells with propidium iodine (PI) staining.

It was found that KCL-22 cells were refractory to 1 µM STI-571 treatment as they continued to grow and at a lower rate than in the absence of the drug. STI-571 at 2.5 µM and above effectively suppressed cell growth and induced partial cell death over time (FIG. 3A). Small clusters of cells formed after about 10 days in treatment groups with 2.5 µM and above of STI-571 and these cells appeared visibly larger with frequent bizarre shapes (FIG. 3B). After two weeks they repopulated the culture, indicating the relapse on the drug treatment. These emerging cells, named KCL-22M, grew equally well as KCL-22 cells, and no longer responded to presence of imatinib in the medium (FIG. 3C). They formed fewer and smaller soft agar colonies (FIG. 3D). The abnormal size and shape of KCL-22M cells were confirmed by flow cytometric analysis, showing increase on both forward scatter (for size) and side scatter (for complexity) (FIG. 3E). KCL-22M cells also exhibited different cell cycle status from KCL-22 cells by increasing S/G2 population (FIG. 3F).

Figure 4:
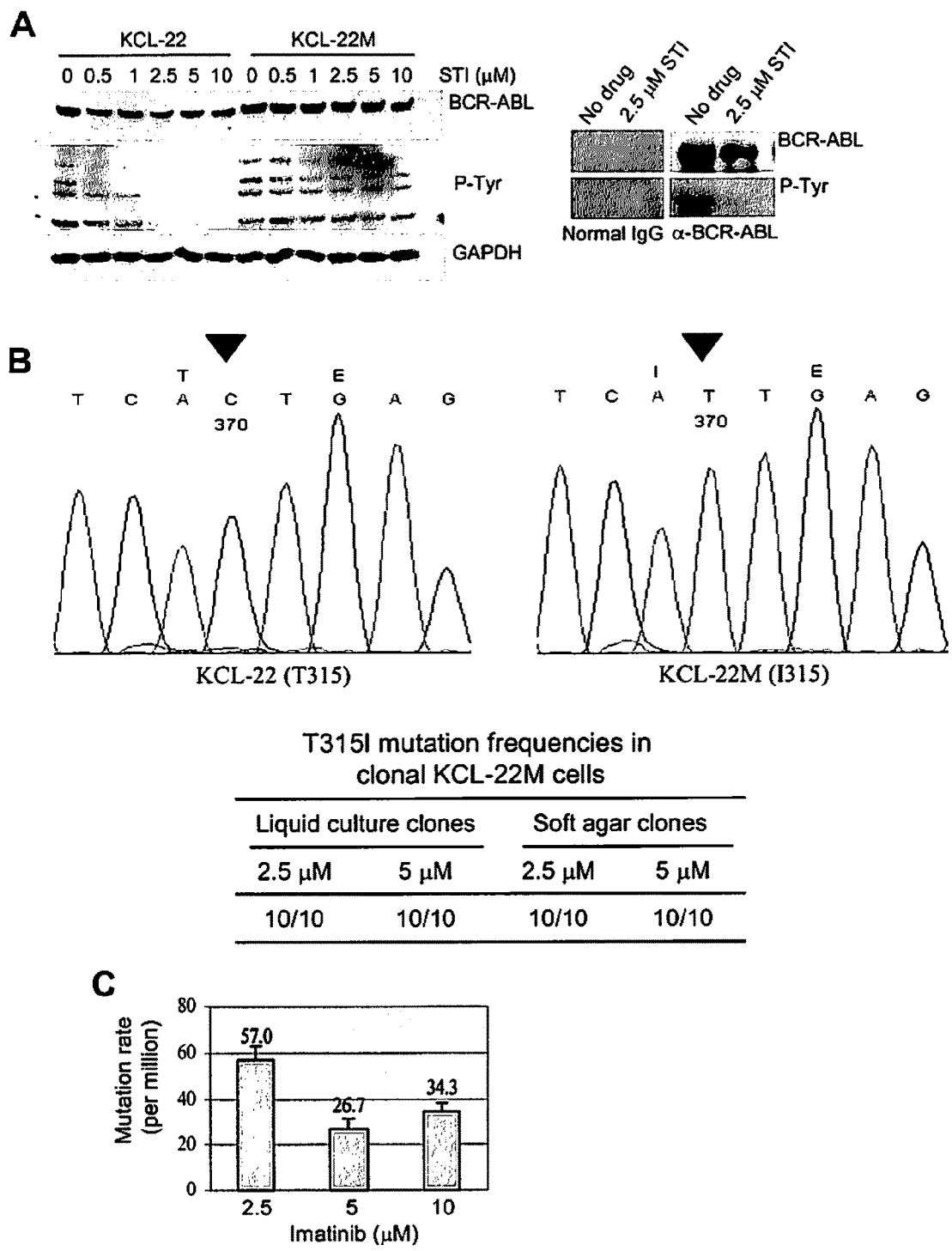
FIG. 4 shows the molecular characterization of a CML resistance model. (A) Left: Western blot analysis of BCR-ABL expression and phosphorylation in KCL-22 and KCL-22M cells with and without imatinib treatment. Right: immunoprecipitation of BCR-ABL in KCL-22 cells followed by Western analysis for expression and phosphorylation. (B) Left: sequencing analysis of BCR-ABL kinase domain with cDNA or genomic DNA from KCL-22 and KCL-22M cells. The point mutation of C to T [SEQ ID NO: 1] (arrow heads) resulting in a T315I amino acid change [SEQ ID NO: 2]. Right: sequencing of BCR-ABL kinase domain mutations in clonal cells.

Molecular characterization of KCL-22M cells was also performed. The KCL-22 cells were refractory to imatinib treatment. Imatinib effectively inhibited tyrosine phosphorylation by direct Western blot analysis of total cell lysate or immunoprecipitation of BCR-ABL protein (FIG. 4A). Tyrosine phosphorylation was not altered by imatinib treatment in KCL-22M cells (FIG. 4A). Since genetic mutations are predominant mechanisms for in vivo resistance of STI-571, it was examined whether mutations occurred in the KCL-22M cells. Both cDNA and genomic DNA were sequenced for BCR-ABL kinase domain using the strategies described by Gorre et al (2001). In the 579-bp cDNA region of BCR-ABL kinase domain covering the ATP-binding pocket and activation loop, a single mutation (C to T nucleotide change that resulted in amino acid T315I mutation at ABL) SEQ ID NO: 2was found in KCL-22M but not parental KCL-22 cells (FIG. 4B). This is the same mutation as identified in patients. The mutant clones represented 40% for 2.5 µM STI-571 or 30% for 5 µM STI-571 treatment in all clones sequenced respectively. Given that KCL-22 cells have a normal copy of ABL gene, which is also be amplified during RT-PCR, half of clones are expected to be wild type. Therefore, the results show that at least 60 to 80% of KCL-22M clones may carry T315I mutation [SEQ ID NO: 2]. Sequencing of genomic DNA further confirmed such a mutation. As T315I mutation [SEQ ID NO: 2] is the most powerful mutation generated after relapse on STI-571, this model recapitulates the BCR-ABL mutagenesis observed in clinical relapse.

The ABL kinase domain was amplified by RT-PCR of total RNA or by PCR of genomic DNA with a high fidelity DNA polymerase (Strategene) using primers. PCR products were cloned into the pCR2.1 vector using TOPO TA Cloning kit (Invitrogen). At least ten clones for each treatment were sequenced by Sequencing Facility of Beckman Research Institute.

Example 2

To determine whether the KCL-22M cells were a mixture of T315I mutants and non-mutants, limiting dilution was performed to obtain individual mutant cells from KCL-22M relapsed on 2.5 and 5 µM imatinib, respectively. Ten clones for each BCR-ABL mutation were sequenced using genomic templates. It was found that 20 clones carried the T315I mutation [SEQ ID NO: 2] (FIG. 4B). Clonal resistant cells were separately derived by plating KCL-22 cells on soft agar with 2.5 or 5 µM imatinib and cell colonies were grown. After three weeks, resistance cell colonies were randomly picked and expanded for DNA sequence analysis. Twenty clones (10 from each concentration of imatinib) carried the T315I mutation [SEQ ID NO: 2] (FIG. 4B). KCL-22 cells at various passages relapsed on imatinib and all recurrent cells had the T315I mutation [SEQ ID NO: 2]. These results indicate that KCL-22 cells develop acquired resistance preferably through the T315I BCR-ABL mutation.

T315I mutation rate. The T315I mutation rate was measured by plating KCL-22 cells on soft agar with imatinib. A standard two-layer soft agar culture was performed with bottom layer of 0.7% agarose and top layer of 0.35% agarose. One million cells per well in 6-well plates on warm top agar with imatinib in both top and bottom agar layers to their final concentrations were incubated for three weeks. Plates were then stained with 0.005% Crystal Violet for 1 hour, and colonies were scored with aid of microscope. The mutation rate with 5 and 10 µM imatinib was around $3\times10^{-5}$, and $5.7\times10^{-5}$ with 2.5 µM imatinib (FIG. 4C). The mutation rate in liquid culture was also measured by serial two-fold dilutions of KCL-22 cells followed by treatment with 5 µM imatinib. The lowest number of cells that consistently relapsed on imatinib was determined. The medium T315I mutation rate was about 1/12,500 or $8\times10^{-5}$. This is in general agreement with the rate observed in soft agar analysis given that the plating efficiency for KCL-22 cells in soft agar was about 25%. These results indicate that imatinib treatment of KCL-22 cells results in acquired resistance through rare T315I mutation. This model recapitulates a key BCR-ABL mutagenesis process that occurs in clinical relapse. This is the first CML resistance model through BCR-ABL mutations that can be rapidly reproduced within two weeks after exposing cells to in vivo effective concentrations of imatinib.

Acquired Resistance of Clonal KCl-22 Cells

In vivo, most BCR-ABL mutations are found in relapsed CML patients although pre-existing T315I mutation [SEQ ID NO: 2] is detected in some CML patients before imatinib treatment (Shah et al., 2002; Soverini et al., 2006). Whether the pre-existing BCR-ABL mutant cells originating in the patient is a requirement for development of resistance was investigated. Individual KCL-22 cell clones were isolated by limiting dilution or soft agar plating without drug treatment. Eleven liquid culture clones (L1-L11) and thirteen soft agar clones (Ag1-Ag13) were expanded for analysis (Table 1). Most of the clones failed to elapse, but four relapsed in two weeks with high frequency at different concentrations of imatinib. These were clones L1, L7, Ag3 and Ag11 (Table 1 and FIG. 5A). After sequence analysis of relapsed cells, it was determined that clone L1 relapsed on 2.5 and 5 µM with E255K BCR-ABL mutation [SEQ ID NO: 3]; clone L7 relapsed on all doses of the drug with Y253H BCR-ABL mutation [SEQ ID NO: 4]; clone Ag3 relapsed without BCR-ABL kinase domain mutations on 2.5 and 5 µM imatinib, but with T315I mutation [SEQ ID NO: 2] on 10 µM imatinib; clone Ag11 relapsed with T315I mutation [SEQ ID NO: 2] on 2.5 µM imatinib which is similar to parental cells (Table 1). In Table 1, no mutations have been detected in clones L1, L7, Ag3 and Ag11 before STI treatment. ND was not done. The asterisk indicates that there was relapse after 50 days and remain sensitive to 2.5 µM STI 571.

TABLE 1

Relapse and mutation analysis in clonal cells

| Clone | STI 2.5 uM Relapsed wells/seeded wells | Mutation | STI 5 uM Relapsed wells/seeded wells | mutation | STI 10 uM Relapsed wells/seeded wells | mutation |
|---|---|---|---|---|---|---|
| L1 | 7/8 | E255K | 4/5 | E255K | 0/5 | |
| L2 | 0/6 | | 0/3 | | ND | |
| L3 | 0/6 | | 0/3 | | ND | |
| L4 | 0/6 | | 1/3 | No | ND | |
| L5 | 1/6 | G250E | 0/3 | | ND | |
| L6 | 0/6 | | 0/3 | | ND | |
| L7 | 8/8 | Y253H | 4/5 | Y253H | 4/5 | Y253H |
| L8 | 0/6 | | 0/3 | | ND | |
| L9 | 0/6 | | 0/3 | | ND | |
| L10 | 0/6 | | 0/3 | | ND | |
| L11 | 0/6 | | 0/3 | | ND | |
| Ag1 | 0/6 | | 0/3 | | ND | |
| Ag2 | 1/6* | ND | 0/3 | | ND | |
| Ag3 | 8/8 | No | 2/2 | No | 5/5 | T315I |
| Ag4 | 0/6 | | 0/3 | | ND | |
| Ag5 | 0/6 | | 0/3 | | ND | |
| Ag6 | 0/6 | | 0/3 | | ND | |
| Ag7 | 1/6 | No | 0/3 | | 0/3 | |
| Ag8 | 5/6* | ND | 0/3 | | 0/3 | |
| Ag9 | 1/6 | No | 0/3 | | 0/3 | |
| Ag10 | 0/6 | | 0/3 | | ND | |
| Ag11 | 8/8 | T315I | 2/2 | ND | 5/5 | ND |
| Ag12 | 0/6 | | 0/3 | | ND | |
| Ag13 | 0/6 | | 0/3 | | ND | |

Figure 5:
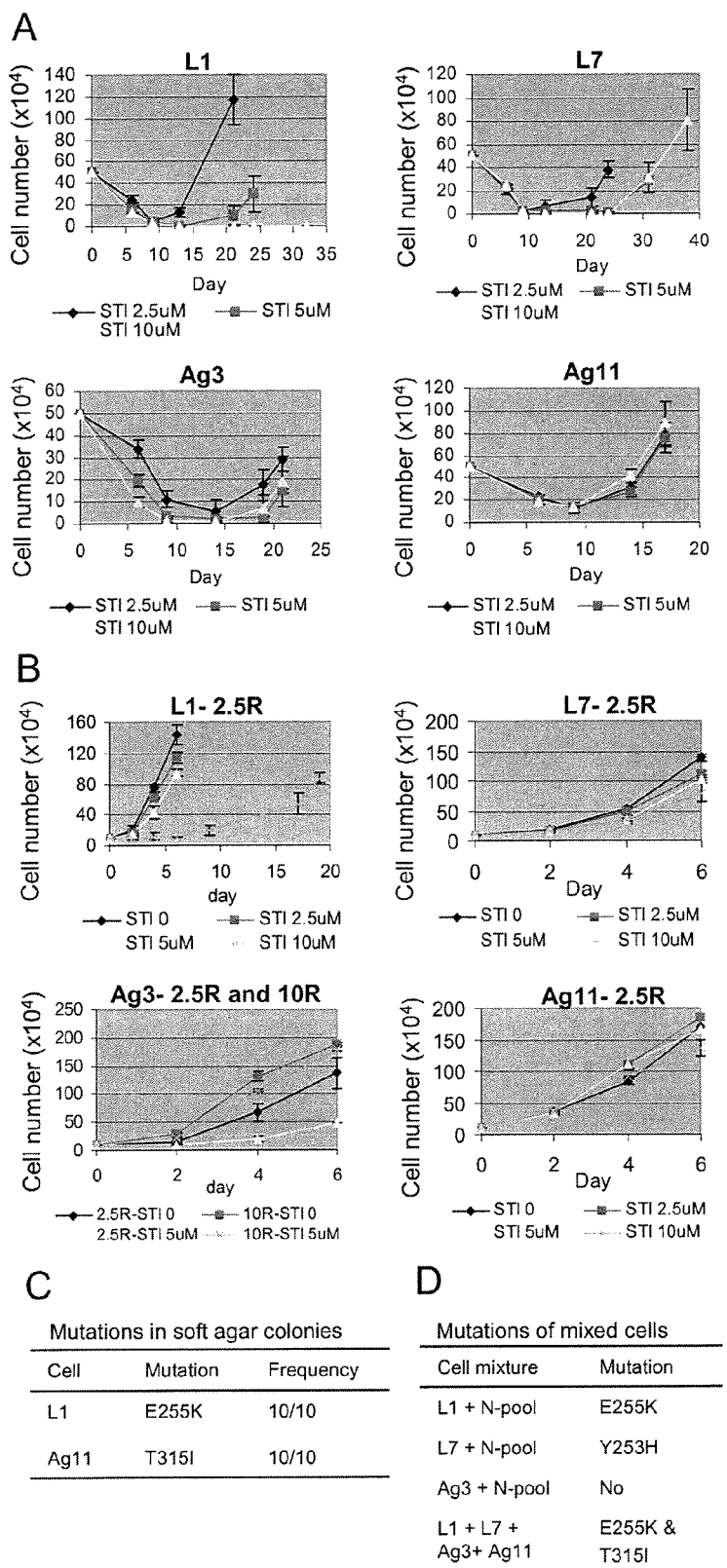
FIG. 5 shows acquired resistance of clonal CML cells on imatinib treatment. (A) Time course of relapse for four KCL-22 clones as analyzed in FIG. 13A. (B) Resistance of recurrent clonal cells to higher concentrations of imatinib. Recurrent cells derived from 2.5 µM imatinib treatment are labeled as 2.5R and recurrent Ag3 cells derived from 10 µM imatinib labeled as Ag3-10R. The different levels of resistance of L1 -2.5R (E255K mutation; [SEQ ID NO: 3]), L7-2.5R (Y253H mutation; [SEQ ID NO: 4]) and Ag11-2.5R (T315I mutation; [SEQ ID NO: 2]) to the higher concentrations of imatinib. Growth of Ag3-2.5R (no mutation) was inhibited by 5 µM imatinib, but not for Ag-3-10R (T315I mutation; SEQ ID NO: 2). (C) Cells from clones L1 and Ag11 were plated on soft agar with 2.5 µM imatinib for three weeks and ten colonies each were picked for sequencing analysis of BCR-ABL kinase domain mutations. (D) Mutations from mixed clonal cells. Equal numbers of eight never-relapse clones were mixed to form a non-relapse pool (N-pool). Clone L1, L7 or Ag3 was then mixed 1:1 with N-pool respectively for resistance analysis in liquid culture, and recurrent cells were analyzed for BCR-ABL mutations. Similarly, equal numbers of clones L1, L7, Ag3 and Ag11 were mixed for resistance and mutation analysis.

These mutations conferred resistance of clonal cells to imatinib with T315I having the greatest protective effect against proliferation inhibition by high concentrations of the drug (FIG. 5B). Compared to parental cells, more BCR-ABL mutations emerged from these clones. The ability of these clones to develop resistance through BCR-ABL kinase domain mutations indicates that a pre-existing mutant cell originating from a patient is not required for resistance.

Example 3

Development of different mutations from parental cells. The development of different mutations from parental cells was examined using the model system of the present invention. It was verified that the clonal cells did develop different mutations. L1 and Ag11 cells were plated on soft agar with 2.5 μM imatinib and ten imatinib-resistant colonies were isolated after three weeks. All resistant L1 colonies carried the E255K [SEQ ID NO: 3] mutation only and all resistant Ag11 colonies carried the T315I mutation [SEQ ID NO: 2] only (FIG. 5C), indicating clone-specific mutation patterns exist for resistance.

Whether the parental mutation type (T315I) [SEQ ID NO: 2] could be restored in clonal cells when re-supplied with a culture environment with the mixture of clonal cells was determined. Clones L1, L7 or Ag3, respectively, were mixed with an equal number of cells from a pool consisting of eight never-relapse clones (N-pool). Identical mutation phenotypes were maintained for relapsed L1, L7 and Ag3 even after treatment with 2.5 or 5 μM imatinib (FIG. 5D). Whether T315I mutation [SEQ ID NO: 2] dominates over other mutations for resistance development was also determined. Equal numbers of cells from clones L1, L7, Ag3 and Ag11 were mixed together and treated with imatinib. In recurrent cells from liquid culture, both E255K [SEQ ID NO: 3] and T315I [SEQ ID NO: 2] mutations were readily detected (FIG. 5D), which was consistent with the fact that L1 and Ag11 were fast relapse clones whereas L7 and Ag3 had slower relapse time courses (FIG. 5A), indicating that T315I [SEQ ID NO: 2] is not superior to E255K [SEQ ID NO: 3] for imatinib resistance. Together, these data indicate a certain plasticity of mutagenesis process in CML cells that may allow induction of different mutations in clonal cells. This plasticity is particularly evident in clone Ag3 which exhibits concentration-dependent induction of T315I [SEQ ID NO: 2] mutation at 10 μM imatinib. Mutation phenotypes of some clonal cells are distinguished from that of parental cells and become clone-dependent.

Figure 6:
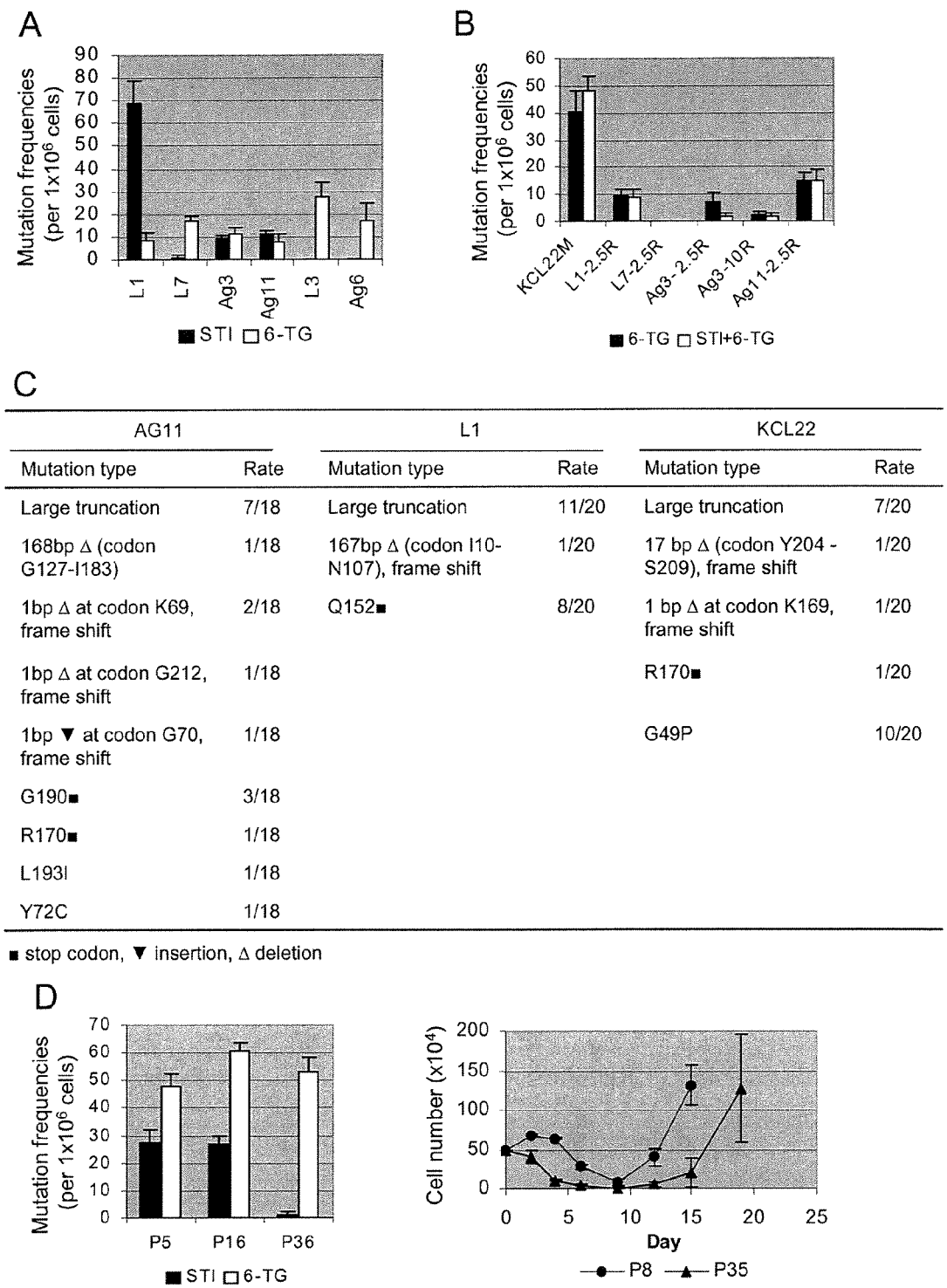
FIG. 6 shows induction of BCR-ABL mutations as compared to spontaneous HPRT mutations. (A) Comparison of BCR-ABL and HPRT mutation rates. Clone Ag3 developed imatinib-resistant colonies through non-BCR-ABL mutation mechanisms. (B) Effects of imatinib treatment on HPRT mutation rate. (C) HPRT mutation spectrum in clone Ag 11, L1 and parental KCL-22 cells. (D) Left: BCR-ABL and HPRT mutation rates of KCL-22 cells at passages 5, 16, and 36 measured by soft agar clonogenic assay. Imatinib, 5 µM; 6-TG, 2.5 µg/ml. Right: time courses for relapse of KCL-22 cells on 2.5 µM imatinib at passages 8 and 35.

Induction of BCR-ABL mutations by imatinib. Because blast crisis CML cells are genetically unstable, over-expression of BCR-ABL alters the fidelity of DNA double-strand break repair (Slupianek et al., 2006) and increases expression and activity of error-prone DNA polymerase which increases DNA replication error (Canitrot et al., 1999). Whether DNA replication error is a cause of rare mutations in clonal or parental cells during clonal expansion and cell propagation was assessed. BCR-ABL mutation rates versus spontaneous mutation rates introduced by DNA replication error were determined. The latter was measured by spontaneous mutations on the HPRT (hypoxanthine phosphoribosyl transferase) gene that resulted in cells resistant to 6-thioguanine (6-TG). As shown in FIG. 6A, BCR-ABL mutation rate was compared side by side with HPRT mutation rate in four relapse-prone clones (L1, L7, Ag3 and Ag11) and two never-relapse clones (L3 and Ag6). HPRT showed relatively constant mutation rate (0.8 to $2.5 \times 10^{-5}$) among all clones regardless of their ability to relapse, whereas BCR-ABL mutation rate was highly clone-dependent, from none (clone L3 and Ag6) to $7 \times 10^{-5}$. The stable HPRT mutation rate among clones reflects the nature of random mutations introduced by DNA replication error in these clones during clonal expansion, which appears different from BCR-ABL mutations that are highly clone-dependent.

Treatment of CML cell lines K562 and BV173 with low doses of imatinib for a short time will specifically induce DNA damage in these cells, but has no effect on non-BCR- ABL expressing leukemic or normal cells (Czechowska et al., 2005). Whether imatinib treatment increases HPRT mutation rate through elevating overall DNA damage level was determined. Since naïve CML cells cannot survive the prolonged culture required for a clonogenic assay, recurrent cells derived from parental and clonal cells were used for treatment with 6-TG and 2.5 µM. As shown in FIG. 6B, imatinib treatment did not alter overall DNA damage levels among these cells.

HPRT mutation types in 6-TG resistant cells were also examined. Loss of function for human HPRT has been well characterized with a broad mutation spectrum including large truncation, deletion, insertion and point mutations on codons (Burkhart-Schultz et al., 1996; Podlutsky et al., 1998). From DNA sequencing analysis of 6-TG resistant soft agar colonies derived from clones Ag11, L1 and parental KCL-22 cells, numerous HPRT truncation, deletion, insertion and point mutations were identified in all these colonies (FIG. 6C). This is consistent with previous observations (Burkhart-Schultz et al., 1996; Podlutsky et al., 1998). The broad spectrum of HPRT mutations differs from the single mutations seen for the above-described parental cells and clones indicating the possibility of a different mutagenesis pathway for BCR-ABL on imatinib. The T315I mutation frequency in parental KCL-22 cells was stable in early passages (p8 and p16) but declined significantly in the late passage (p36) (FIG. 6D). Thus, the relapse of late-passage KCL-22 cells was delayed, although the recurrent cells still harbored T315I mutation. In contrast, HPRT mutation rates remained relatively constant even in the late passages of KCL-22 cells. This indicates that BCR-ABL mutations are actively induced by imatinib treatment.

Example 4

Figure 7:
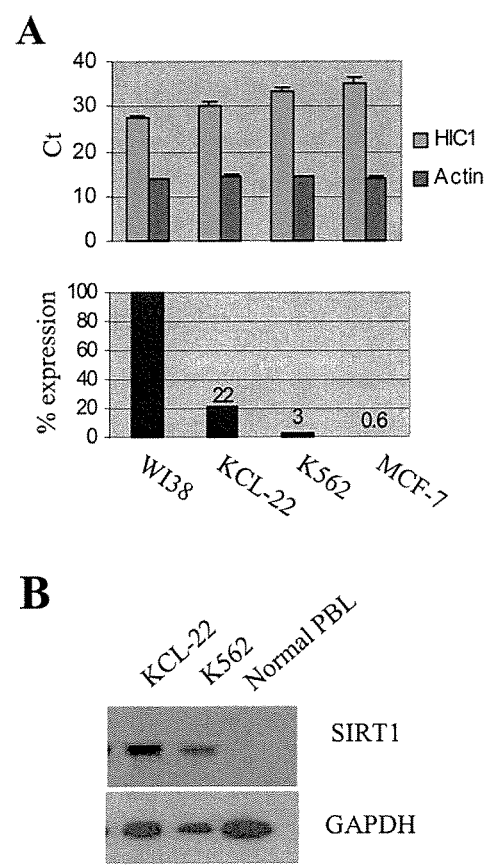
FIG. 7 shows HIC1 and SIRT1 expression in CML cells. (A) HIC1 expression by qRT-PCR. Ct of HIC1 or control actin for PCR amplification was first determined (top) and relative abundance of HIC1 level was calculated with WI-38 cells as positive control (100% expression) and MCF-7 as silencing control. (B) SIRT1 expression by Western blot. Normal peripheral blood mononuclear cells (PBL) as control.

SIRT1 inhibitor sirtinol synergizes with STI-571 for apoptosis induction in CML cells. Expression of HIC1 in CML cell lines KCL-22 and K562 was examined by quantitative real-time RT-PCR for the major HIC1 transcript from its promoter 1a. The gene was silenced or down regulated in both cell lines compared to full HIC1 expression in WI-38 cells and silencing in MCF-7 cells (FIG. 7A). This is a consequence of promoter hypermethylation (Chen et al., 2003; Issa et al., 1997). Western blot analysis showed that SIRT1 was overexpressed in both cell lines after HIC1 gene silencing (FIG. 7B).

Total cellular RNA was extracted with Trizol (Invitrogen) using a standard protocol. The first strand DNA was synthesized and HIC1 expression was analyzed by quantitative real-time RT-PCR using a kit with SYBR Green label (Invitrogen) as per the manufacture's instruction on BioRad machine OPTICON. HIC1 primers were used spanning introns, 5'-GGACGGACCAGCAGGACA-3' (exon 1a) [SEQ ID NO: 15] and 5'-GCGCTGGTTGTTGAGCTG-3' (exon 2) [SEQ ID NO: 16]. SIRT1 expression was analyzed by Western blot using 1:5000 diluted rabbit monoclonal SIRT1 antibody (Epitomics). GAPDH was analyzed as a loading control with a rabbit antibody (Trevigen) at 1:5000 dilution.

Figure 8:
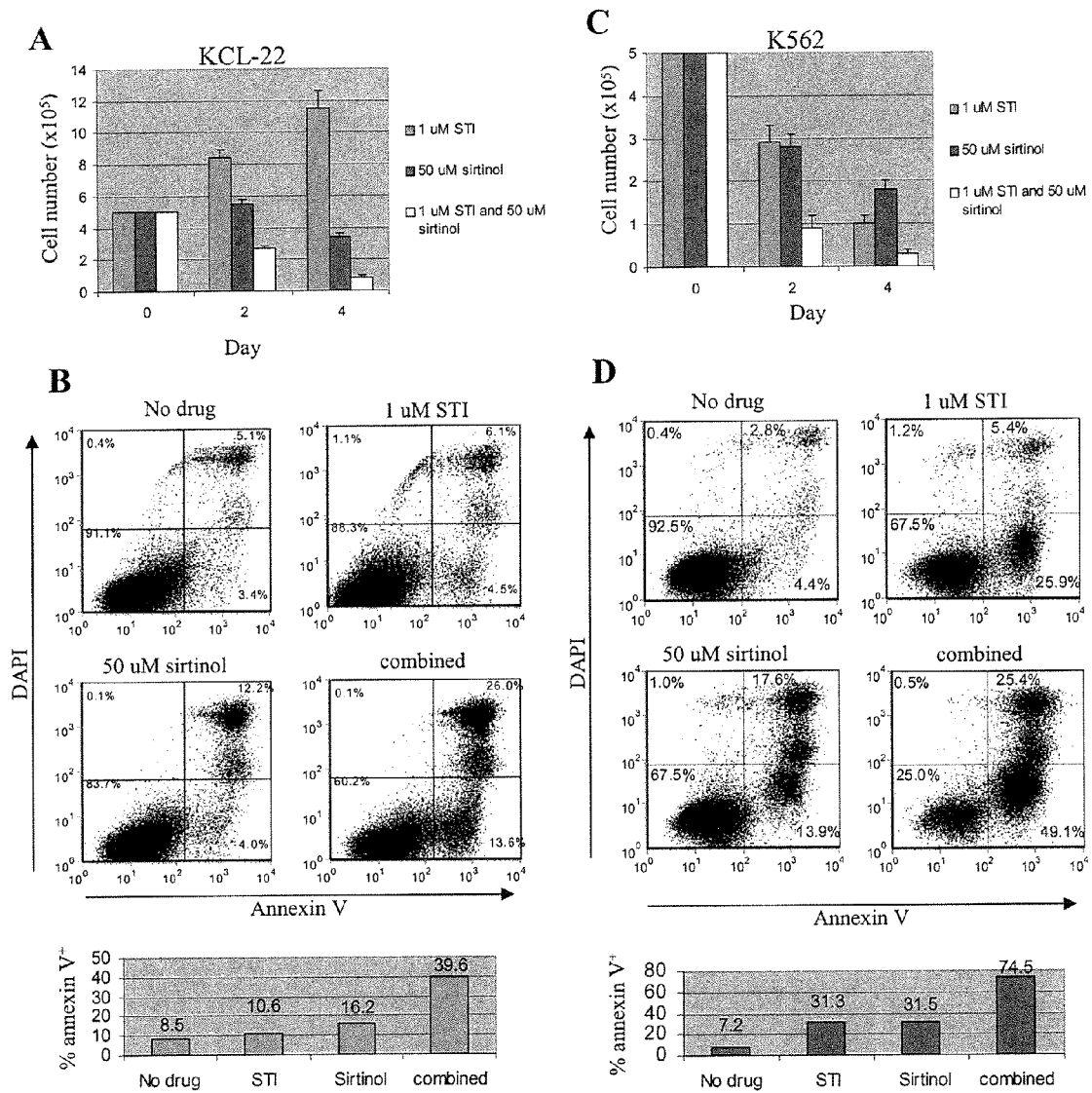
FIG. 8 shows SIRT1 inhibitor promotes apoptosis of CML cells. KCL-22 cells (A, B) or K-562 cells (C, D) were treated with 1 µM STI-571 (STI) with or without 50 µM sirtinol. Half millions per well were seeded in a 24-well plate and at 2 and 4 days after initiation of drug treatment, surviving cells were counted (A, B). Apoptosis in both cell lines was analyzed at two days (KCL-22) or one day (K-562) after drug treatment (C, D). The percentage of annexin V positive cells including early and late apoptotic cells was plotted underneath FACS charts.
Figure 9:
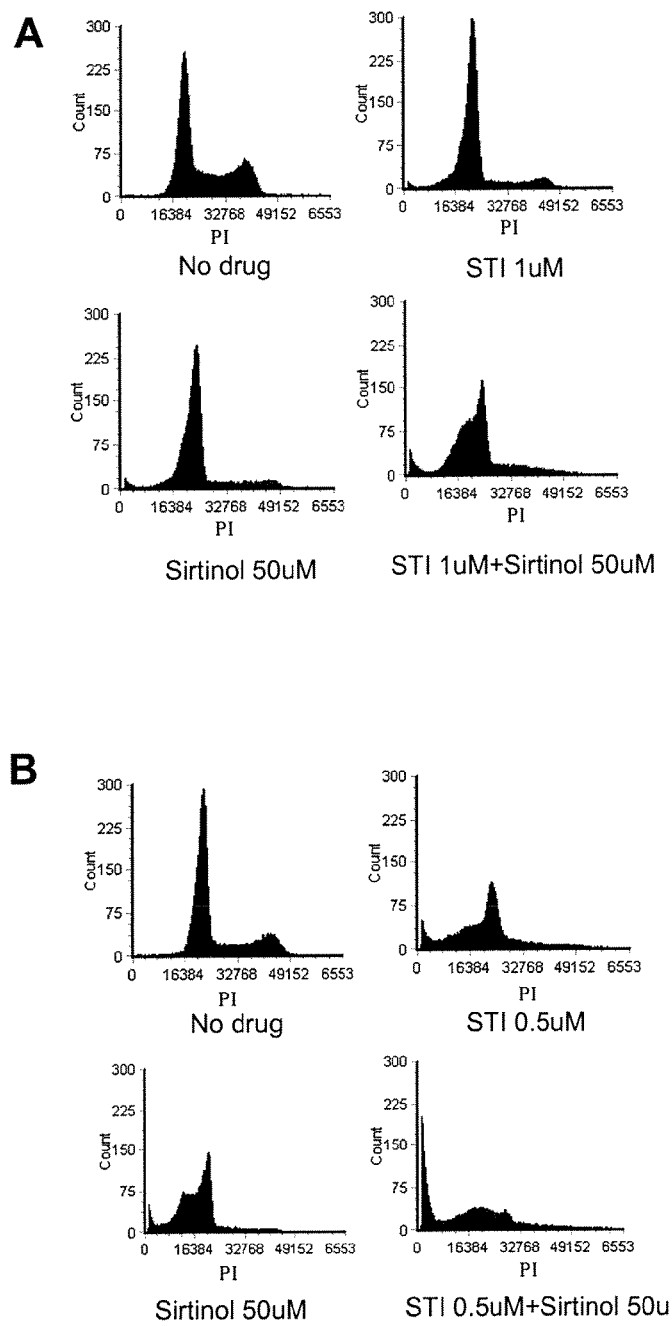
FIG. 9 shows cell cycle change upon sirtinol and STI-571 treatment. KCL-22 (A) and K-562 (B) cells were treated with conditions as indicated for two days and cells were labeled with propidium iodine (PI) for cell cycle analysis.

Sirtinol inhibits SIRT1 and other sirtuin deacetylases with an $IC_{50}$ about 50 to 130 µM (Grozinger et al., 2001; Mai et al., 2005; Ota et al., 2005). STI-571 treatment alone induced rapid apoptosis in K562 cells with $IC_{50}$ of about 0.5 µM while it had a mild effect on KCL-22 cells (FIG. 8) (Mahon et al., 2000). Treatment with 50 µM sirtinol alone inhibited the growth of both cell lines, and the combination of two drugs synergized their inhibitory effects (FIG. 8 A, C). Sirtinol alone significantly induced annexin V positive apoptotic cells in both lines and when combined with STI-571, it induced more dramatic apoptosis than each individual drug (FIG. 8B, D). Sirtinol and STI-571 both affected cell cycle of CML cells by reducing S/G2 and increasing sub-G1 population in KCL-22 cells (FIG. 9A) while they rapidly increased sub-G1 and apoptotic fraction in K562 cells (FIG. 9B). Cell cycle was analyzed by fixing cells with 70% ethanol and then stained with propidine iodine (50 µg/ml) for 30 min at room temperature. Cell apoptosis was analyzed with annexin V kit (BD Pharminggen) as per the manufacturer's instruction.

Figure 10:
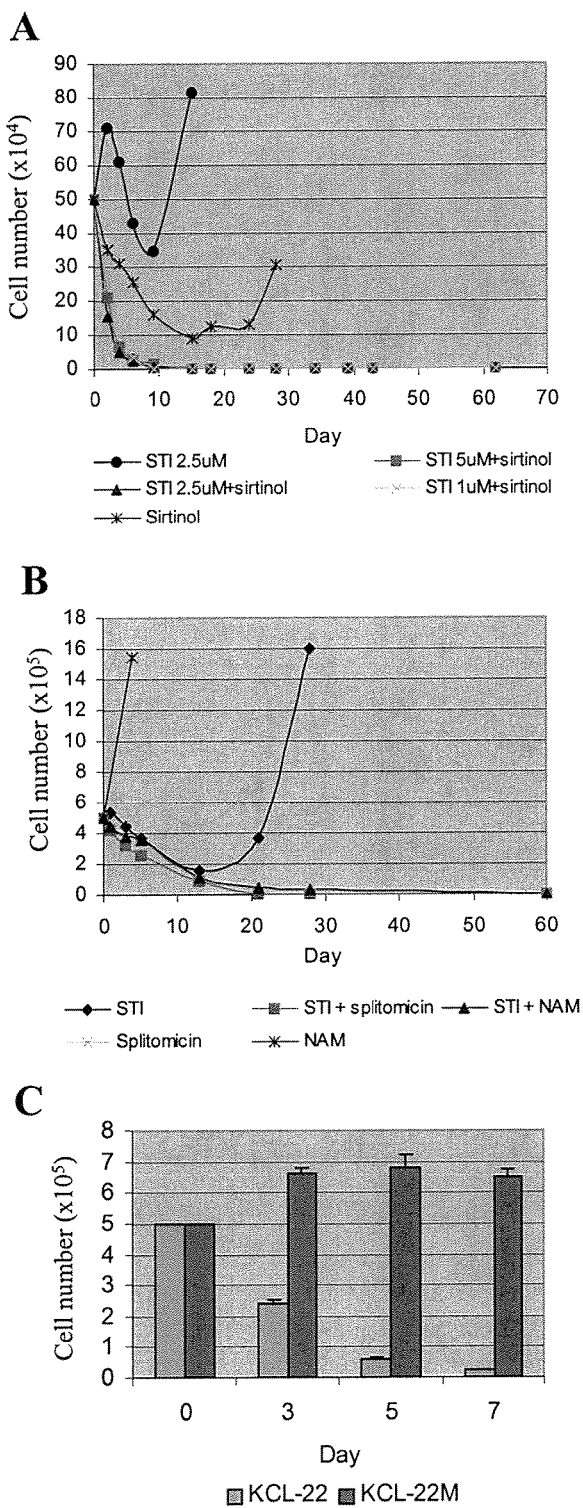
FIG. 10 shows SIRT1 inhibitors block relapse of CML on imatinib treatment. (A) One half million KCL-22 cells were treated with 50 µM sirtinol or STI-571 alone at the concentration indicated or in combination of the two drugs. Cells for STI-571 treatment alone all relapsed. Sirtinol blocked relapse at all dosages of STI-571. A small volume of drug-free medium was supplied after three to five weeks of treatment to restore the original volume during the prolonged culture for two to three months. (B) KCL-22 cells were treated with 300 µM splitomicin or 15 mM nicotinamide alone or their combination with 5 µM STI-571. Both splitomicin and nicotinamide blocked relapse. (C) Comparison of KCL-22M and KCL-22 cells in response to the treatment with 2.5 µM STI-571 combined with 50 µM sirtinol.

Pharmacological inhibition of SIRT1 prevents CML relapse on STI-571. Using the CML acquired resistance model as described herein, prevention of CML relapse on STI-571 was examined. Inhibition of SIRT1 with small molecule inhibitors prevented CML relapse on STI-571. KCL-22 cells were treated with STI-571 at 1, 2.5 and 5 µM in combination with various concentrations of sirtinol. At 50 µM and above, sirtinol effectively eliminated KCL-22 cells in two to three weeks and blocked relapse of KCL-22 cells on all three concentration of STI-571 in culture for two to three months and no viable cells were visible under microscope (FIG. 10A). As with STI-571, treatment with sirtinol alone resulted in relapse after two weeks (FIG. 10A). The combination of sirtinol and STI-571 is a powerful therapeutic approach for inhibiting acquired resistance of CML.

Testing of additional SIRT1 inhibitors. Another sirtuin specific inhibitor, splitomicin (Bedalov et al., 2001; Hirao et al., 2003), was also tested for its ability to block relapse. Splitomicin is also a naphthol compound and structurally similar to sirtinol. Nicotinamide is a natural inhibitor of SIRT1 (Avalos et al., 2005; Bitterman et al., 2002). At 300 µM splitomicin and 15 mM nicotinamide, relapse of KCL-22 cells on 5 µM STI-571 was effectively blocked during prolonged culture as shown in FIG. 10B. In contrast to sirtinol, splitomicin and nicotinamide did not, by themselves, induce significant cell death and did not dramatically enhance cell killing by STI-571 during the first two weeks (FIG. 10B). These results indicate that prevention of relapse does not require enhanced cell killing.

The T315I mutation is resistant to treatment with nilotinib (Weisberg et al., 2005) as well as dasatinib (Shah et al., 2004). In murine cells transduced with wild type BCR-ABL, the T315I mutation is also commonly induced by these drugs (von Bubnoff et al., 2006; von Bubnoff et al., 2005). Using the KCL-22M cell line, combined treatment with sirtinol and STI-571 was able to inhibit cell growth (FIG. 10C).

Example 5

Figure 11:
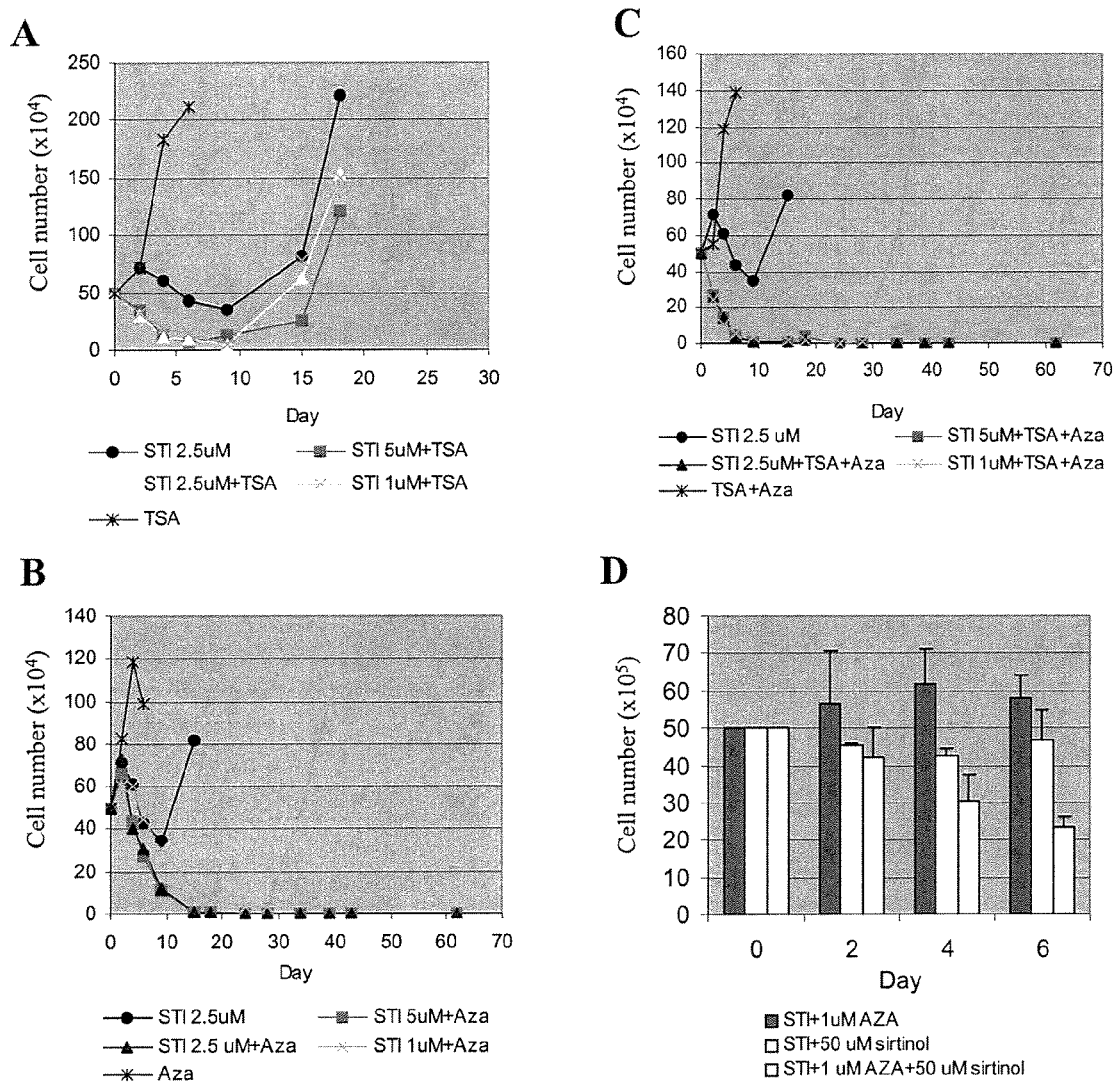
FIG. 11 shows effects of inhibitors for HDACs and DNMTs on CML chemoresistance. (A-C) KCL-22 cells were treated with 1 µM TSA (A), 1 µM AZA (azacytidine) (B), or 1 µM TSA (trichostatin A) plus 1 µM AZA (C) without and with STI-571 at the concentration indicated. AZA but not TSA blocked relapse at 2.5 and 5 µM of STI-571. (D) Responses of KCL-22M cells to the treatment with 2.5 µM STI-571 in combination with 1 µM AZA, 50 µM sirtinol, or 1 µM AZA plus 50 µM sirtinol.

Effects of inhibitors of deacetylases and DNA methyltransferases (DNMT) on chemoresistance of BCR-ABL positive leukemia. In vitro, enhanced killing of CML cells occurs when imatinib is combined with DNMT inhibitor 5-aza-2-deoxycytidine (AZA) (La Rosee et al., 2004) or with HDAC inhibitors (Kawano et al., 2004; Yu et al., 2003). Whether these inhibitors prevent CML relapse on STI-571 was examined. TSA at 1 µM alone had little toxicity on KCL-22 cells, but when combined with STI-571, massive apoptosis and dramatic cell killing was observed on all dosages of STI-571 (FIG. 11A and data not shown). After ten days, cells on all dosages of STI-571 relapsed (FIG. 11A). These results indicate that an initial rapid and massive cell killing does not necessarily prevent relapse of CML on imatinib treatment. However, the combination of AZA with STI-571 while killing cells more slowly than TSA, did successfully block relapse on 2.5 and 5 µM (FIG. 11B). When AZA, TSA, and STI-571 were all combined, initial rapid cell death occurred due to the presence of TSA and relapse was blocked on 2.5 and 5 µM of imatinib due to the presence of AZA (FIG. 11C). TSA and AZA alone or in combination could not reactivate HIC1 expression or reduce SIRT1 level despite their effects on KCL-22 cells. This is in contrast to HIC1 reactivation by these drugs in carcinoma cells (Narayan et al., 2003; Rathi et al., 2003), indicating that hypermethylated HIC1 promoter is more difficult to reactivate in CML cells. For KCL-22M cells, TSA had no effect on cell growth, whereas 1 µM AZA inhibited its growth but did not promote significant cell death. The combination of 1 µM AZA with 50 µM sirtinol induced partial cell death (FIG. 11D).

Figure 12:
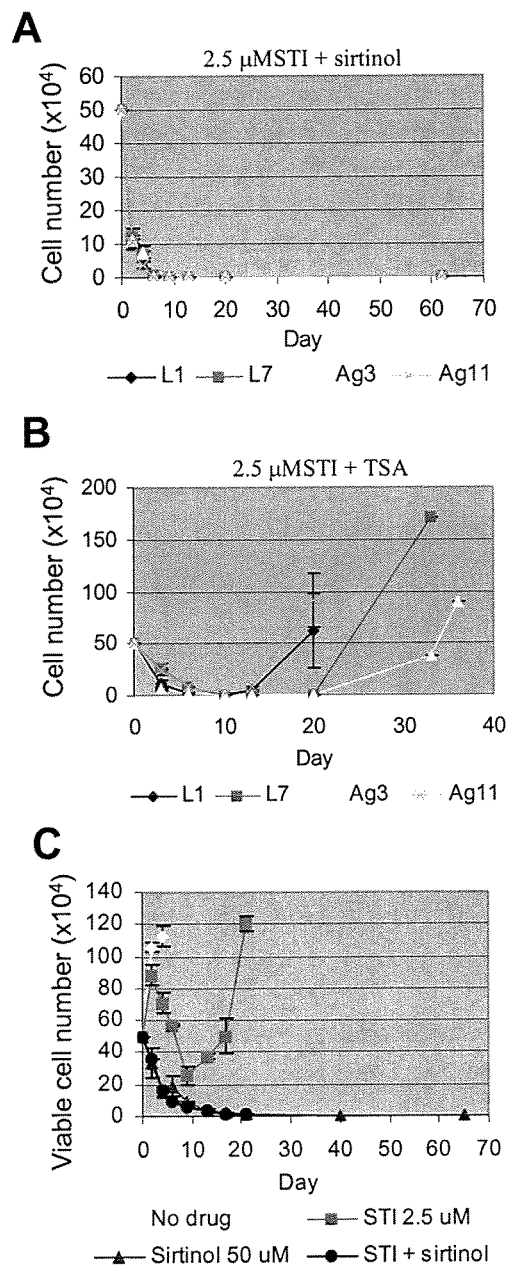
FIG. 12 shows effects of deacetylase inhibitors on clonal CML cells and BCR-ABL positive ALL cells. (A, B) One half million each of clonal KCL-22 CML cells were treated with 2.5 µM imatinib plus 50 µM sirtinol (A) or 1 µM TSA (B). (C) SD-1 ALL cells were treated with 2.5 µM imatinib, 50 µM sirtinol or combination. Cells relapsed on imatinib treatment alone without detectable BCR-ABL mutations.

Using the acquired resistance model of the invention, the effects of sirtinol and TSA was further investigated using clonal cells. These clones of KCL-22 cells develop acquired resistance to imatinib through different mutations in three clones (E255K [SEQ ID NO: 3] for clone L1, Y253H [SEQ ID NO:4] for clone L7 and T315I [SEQ ID NO: 2] for clone Ag11) and non-mutation mechanism in clone Ag3 (Yuan et al., 2008). As shown in FIG. 12A&B, the combination of sirtinol with 2.5 µM imatinib blocked relapse in all four clones; in contrast, all clones relapsed on the combination of TSA with imatinib. Clone Ag3, developed resistance through non-BCR-ABL mutation mechanism by 2.5 µM imatinib alone, but developed resistance through T315I mutation [SEQ ID NO: 2] upon the combined imatinib and TSA treatment. These data suggest that HDAC inhibitors transiently provide enhancement of cell killing, but promote genetic mutations of BCR-ABL and acquired resistance.

Example 6

Resistance in acute lymphocytic leukemia. The ability of sirtinol and imatinib to block resistance related to BCR-ABL mutations and non-mutants was determined in acute lymphocytic leukemia (ALL) cells. In humans, adult BCR-ABL bearing (ALL) is highly chemoresistant and treatments are rarely successful, resulting in a poor survival rate ranging from <10% to 20% (Bassan et al., 2004). Similar to KCL-22 cells, the ALL cell line, SD1 is refractory to STI-571 treatment (Deininger et al., 1997). Here, it was observed that prolonged treatment of SD1 cells with STI-571 induced partial cell death, with cells relapsing after ten days without BCR-ABL mutations (FIG. 12C). SIRT1 inhibitor sirtinol alone or in combination with STI-571 could eliminated these cells during prolonged cell culture (FIG. 12C) indicating again, that SIRT1 controls key molecular pathways for chemoresistance of BCR-ABL positive leukemia. Suppression of SIRT1 along with BCR-ABL is an effective therapeutic approach.

Example 7

Figure 13:
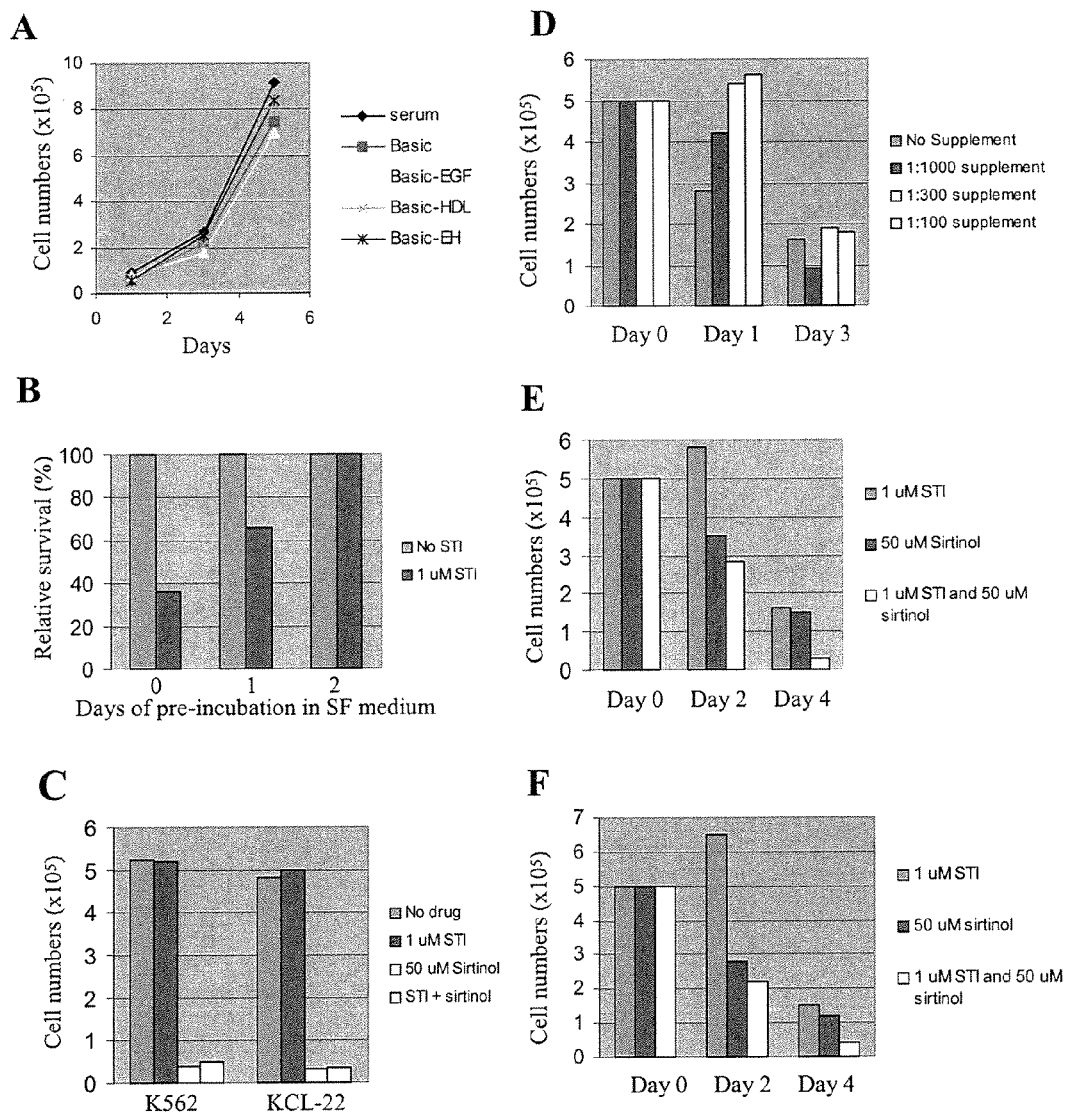
FIG. 13 shows sirtinol inhibits growth factor-induced transient resistance of CML cells (A) Growth curves of K562 cells in serum medium, and serum-free medium supplied with basic supplements containing 5 µg/ml insulin and 5 µg/ml transferrin (basic) with or without 75 ng/ml EGF, 25 µg/ml HDL or both (EH). (B) Responses of K562 cells to STI-571 treatment in SF medium with basic supplements. Cells were immediately switched from serum to SF medium (Day 0) or pre-incubated in SF medium for 1 or 2 days before treatment with 1 µM STI-571. Relative survival of imatinib treated cells was calculated by comparison to no drug treatment. Pre-incubation for two days renders resistance. (C) K562 cells were pre-incubated in SF medium for two days as in B, and then treated with 1 µM STI-571, 50 µM sirtinol or both. Since sirtinol is insoluble in SF medium, HDL 25 µg/ml was added to help dissolve the drug. (D) Effects of basic supplements in serum medium. K562 cells were placed in serum medium and treated with 1 µM STI-571 with or without the supply of basic supplements to final dilution as 1:100, which gives 5 µg/ml insulin and 5 µg/ml transferrin, or lower as indicated. Viable cells were counted one and three days after the treatment. (E) K562 cells were placed in serum medium with the supply of basic supplements at 1:100 dilution and treated with 1 µM STI-571, 50 µM sirtinol or both. (F) Effects of insulin in resistance. K562 cells were cultured in serum medium with addition of 500 ng/ml insulin and treated with 1 µM STI-571, 50 µM sirtinol or both.

Sirtinol overcomes growth factor-induced transient resistance in CML cells. With the exception of KCL-22 cells, no other CML cell lines are known to survive 1µM STI-571 treatment in serum containing culture. Whether serum-free medium supplied with select growth factors provides a better culture environment for developing CML chemoresistance was determined. Serum-free (SF) medium with insulin, transferring, epidermal growth factor (EGF) and high density lipoprotein (HDL) was used. SF medium with the basic supplements (5 µg/ml insulin and 5 µg/ml transferrin) was sufficient to support growth of both K562 cells (FIG. 13A) and KCL-22 cells. Pre-incubation of K562 cells in SF medium with basic supplements for two days made K562 cells as refractory as KCL-22 cells for treatment with 1 µM STI-571 (FIG. 13B, C). Sirtinol alone or in combination with STI-571 resulted in rapid killing of both K562 and KCL-22 cells (FIG. 13C) and no relapse over prolonged culture. Sirtinol is able to overcome CML resistance in SF culture. Addition of basic supplements to routine serum media also provided K562 cells transient resistance to treatment with 1 µM STI-571 (FIG. 13D), which lasted up to two days. Again, treatment with 50 µM sirtinol abolished this transient resistance (FIG. 13E).

Transient resistance conferred by insulin and transferrin supplement is of interest as insulin receptor is over-expressed in about 90% primary CML cells. The key insulin downstream target phosphatidylinositol-3 kinase (PI3K) is required for BCR-ABL mediated transformation and inhibition of PI3K-Akt-mTor pathway has been explored to overcome CML chemoresistance. SIRT1 is a key gene for regulating insulin secretion and directly regulates Akt downstream target FOXO proteins through deacetylation. Therefore, the effect of insulin itself for transient resistance to imatinib and the response of sirtinol treatment was examined. The addition of a broad range of concentrations of insulin, from 1 ng/ml to 5 µg/ml, provided about equal transient resistance of K562 to the treatment with 1 µM STI-571; and again, sirtinol alone or in combination with STI-571 abolished this transient resistance (FIG. 13F). Together, these data show that activation of insulin pathway is sufficient to render CML cells transient resistance in vitro, and it can be inhibited by SIRT1 inhibition.

Example 8

Figure 14:
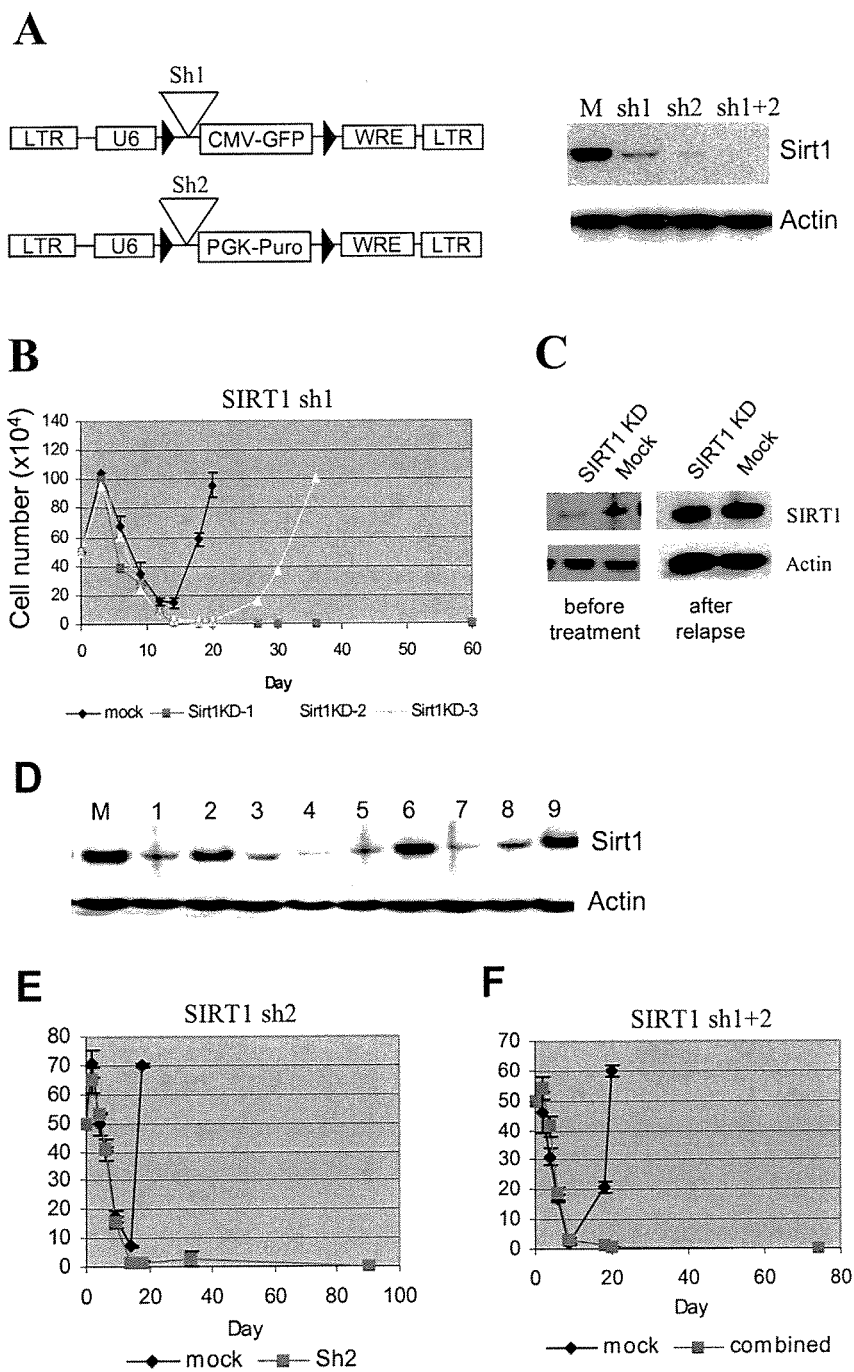
FIG. 14 shows SIRT1 is essential for CML acquired resistance. (A) Structures of SIRT1 shRNA lentiviral vectors and effects of SIRT1 knockdown in KCL-22 cells. The first shRNA (Sh1) was cloned into the pSicoR CMV-GFP vector and the second (Sh2) was cloned into the pSicoR PGK-puro vector. Scrambled shRNA was packaged in both vectors for mock controls. (B) SIRT1 Sh1 knockdown or mock knockdown KCL-22 cells were enriched by FACS, and one half million cells each were treated with 5 µM STI-571 in triplicate. All triplicate samples of mock knockdown relapsed at the same time and were plotted as a single curve with error bars shown. The triplicate SIRT1 knockdown samples were plotted individually as they either did not relapse (sample 1) or delayed the relapse (sample 2 and 3). (C) Western blot analysis of SIRT1 expression in SIRT1 knockdown cells before and after relapse on STI-571 treatment. (D) SIRT1 expression in clones of SIRT1 knockdown KCL-22 cells with Sh1 vector. The FACS-enriched cells were cloned by limiting dilution and single cell seeding was confirmed by microscope. M, mock knockdown. (E) Effects of SIRT1 knockdown with the second shRNA (Sh2) cloned in pSicoR PGK-pure. The transduced cells were selected with puromycin for one week before analysis. The protein knockdown was shown in (A). (F) Effects of SIRT1 knockdown by Sh1 and Sh2. The protein knockdown was shown in (A).

SIRT1 is essential for CML chemoresistance. The effects of SIRT1 stable knockdown on blockage of CML relapse by SIRT1 inhibitors was determined. SIRT1 shRNAs were designed as described previously (Reynolds et al., 2004). The first SIRT1 shRNA, Sh1, was subcloned into a lentiviral vector pSicoR (Ventura et al., 2004) which contains an expression cassette for green fluorescent protein (GFP) (FIG. 14A). A scrambled shRNA was subcloned into the vector as a mock control. The VSV-G (G protein of vesicular stomatitis virus) pseudotyped lentiviral vectors were produced using a four-plasmid transfection system as described (Kowolik et al., 2003). These vectors transduced KCL-22 and K562 cells with high efficiency and significant SIRT1 knockdown was observed in both cell lines (FIG. 14A). Mock or SIRT1 knockdown cells were enriched by fluorescent activated cell sorting (FACS) for GFP expression. No significant growth inhibition by SIRT1 knockdown on CML cells was observed. Treatment with imatinib resulted in relapse of the mock knockdown KCL-22 cells after two weeks. The SIRT1 knockdown showed significantly delayed or abolished relapse with relapse ranging from complete blockage during the two-month culture to delay by 27 days (FIG. 14B). SIRT1 expression in the relapsed SIRT1 knockdown cells was restored to the same level as that in the mock knockdown cells indicating that relapse in the SIRT1 Sh1 knockdown cells is mediated by those cells which contain little SIRT1 knockdown in the original knockdown pool (FIG. 14C).

The heterogeneity of SIRT1 knockdown in the pooled population was confirmed using limiting dilution to clone individual SIRT1 knockdown and mock knockdown cells. About one-third of SIRT1 knockdown clones did not have significant SIRT1 knockdown (FIG. 14D) while SIRT1 level in mock knockdown clones remained unchanged.

Additional SIRT1 knockdown was also generated using different shRNA targets. Sh2 was cloned into a vector similar to pSicoR CMV-GFP with a PKG-puro expression cassette instead of CMV-GFP cassette (FIG. 14A). This allows for enrichment of transduced cells using puromycin selection.

SIRT1 Sh2 exhibited a higher knockdown efficiency than Sh1 (FIG. 14A). The mock knockdown KCL-22 cells relapsed after two weeks but SIRT1 Sh2 knockdown completely blocked the relapse for two months (FIG. 14E). Whether the vector sequence affects shRNA function was also assessed. SIRT1 Sh1 was subcloned into pSicoR PGK-puro vector and found to function similarly to Sh1 in pSicoR CMV-GFP vector—only able to delay the relapse. This indicates that it is the level of knockdown but not the type of vector used that affects resistance. SIRT1 knockdown using both Sh1 and Sh2 resulted in a further decreased SIRT1 level (FIG. 14A), completely blocking relapse of KCL-22 cells for two months (FIG. 14F). This indicates that SIRT1 is a gene that regulates CML acquired resistance by promoting BCR-ABL mutagenesis during imatinib treatment.

Example 9

Figure 15:
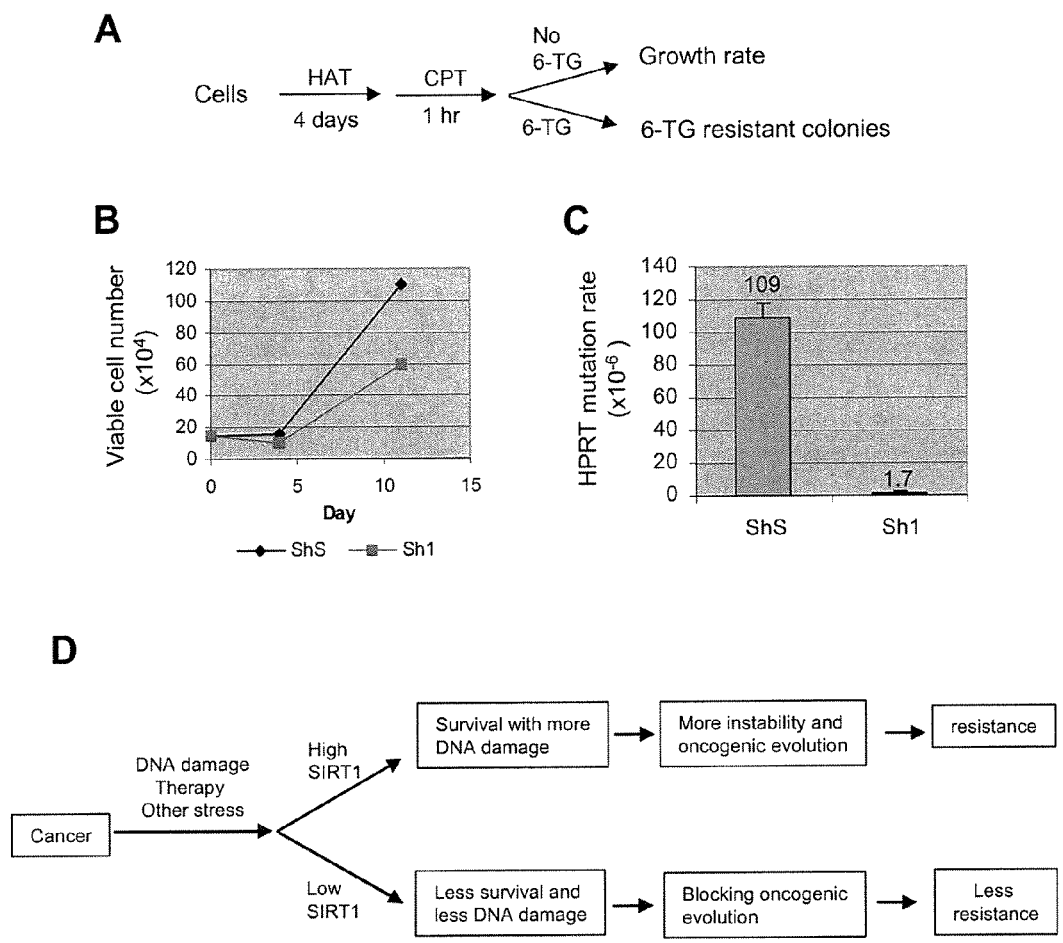
FIG. 15 shows effects of SIRT1 on DNA damage-induced mutations. (A) Schematic of de novo HPRT mutation assay. (B) Survival and proliferation of HAT-selected and CPT treated cells. KCL-22 cells with SIRT1 Sh1 knockdown had half the survival/proliferation rate of mock knockdown cells. (C) HPRT mutation rate of HAT-selected and CPT treated cells. The effectiveness of HAT pre-selection was confirmed by plating one million HAT-selected cells on soft agar with 6-TG and produced no colony (not shown). One million HAT-selected and CPT treated cells each from SIRT1 or mock knockdown were analyzed for 6-TG resistance. (D) Model of roles of SIRT1 in cancer chemoresistance. High expression levels of SIRT1 promote cancer cells survival under conditions of DNA damage agents, chemotherapy, and other stress, whereas accumulating DNA damages, promoting genetic instability and evolution of ontogenesis such as resistant mutations, to survive and resist treatments. Inhibition of SIRT1 blocks such process and prevents acquired resistance.

SIRT1 promotes genetic instability and oncogenic evolution in cancer. The role of SIRT1 in regulating de novo DNA damage in CML cells was investigated. SIRT1 and mock knockdown KCL-22 cells were treated with hypoxanthine aminopterin thymidine (HAT) to remove preexisting HPRT mutation, followed by treatment with camptothecin (CPT) to induce DNA damage. Cells were then analyzed for survival/proliferation and HPRT mutations. SIRT1 Sh1 knockdown cells exhibited two fold less survival over time than mock cells (FIG. 15B). HPRT mutation rate in SIRT1 knockdown cells was decreased by 64 fold (FIG. 15C). Similar results were obtained by SIRT1 Sh2 knockdown. The sharp reduction in de novo HPRT mutation rate observed in SIRT1 knockdown cells is a novel finding. These results indicate that SIRT1 is a key protein promoting genetic instability and the evolution of oncogenes to resist and survive drug therapy and overcome DNA damage (FIG. 15D).

Example 10

Molecular basis of differential effects of sirtinol and TSA on CML chemoresistance. Sirtinol inhibits NAD-dependent class III histone deacetylases (sirtuin family) while TSA inhibits class I and II histone deacetylases (HDACs). The sirtuin family deacetylases are structurally unrelated to HDACs. Both SIRT1 and HDACs are critically involved in regulating gene transcription and post-translational deacetylation of numerous proteins. However, two inhibitors exhibit sharply different outcomes on blocking KCL-22 relapse on STI-571. Gene expression microarray approach was used to search for differential transcriptional regulation and to use a proteomic approach to search for differential protein acetylation profiles.

The effects of these inhibitors on global gene transcription and global protein acetylation is analyzed. Total RNA is extracted from four groups of KCL-22 cells: untreated, treated with STI-571 alone, treated with STI-571 and sirtinol, and treated with STI-571 and TSA at three time points (2, 4 and 8 days) before relapse occurs. Each sample is collected in triplicate. Samples are then analyzed using Affymetrix expression arrays followed by statistical analyses of gene expression changes among different groups. Relevant genes are identified and RT-PCR or Western blot is used to confirm their expression. The functional significance of new genes/targets in CML chemoresistance is further studied by knockdown in KCL-22 cells similar to that described for SIRT1.

Total cell lysate is extracted from the four groups of KCL-22 cells at three time points as described for the expression array. Lysates are immunoprecipitated with anti-acetylated lysine antibody and bound proteins are eluted for gel electrophoresis. The gel is stained with Coomassie and differential bands are sliced for mass-spectrum analysis. Once key acetylation targets are identified, they are verified individually by immunoprecipitation and Western blot. The following antibodies for protein analysis by Western blot are used: rabbit monoclonal anti-SIRT1 (1:5000, Epitomics), rabbit polyclonal anti-PGC-1α (1:1000, Chemicon) and anti-GAPDH (1:5000, Trevigen).

Example 11

The potential downstream targets of SIRT1 that are involved in controlling the CML cell resistance are determined. p53 is a key downstream target of SIRT1 for apoptotic control in solid tumors. However, p53 is mutated in both KCL-22 and K562 cells, indicating that other SIRT1 targets might be involved. Involvement of another SIRT1 target, peroxisome proliferator-activated receptor-gamma coactivator 1 alpha (PGC-1α), for induction of BCR-ABL mutations through regulating reactive oxygen species (ROS) is examined. The ROS production is dramatically increased in blast crisis CML, which results in accumulation of DNA damage product 7,8-dihydro-8-oxo-2'-deoxyguanosine (8-oxoG). Over-expression of BCR-ABL in murine cells induces ROS production, DNA damage and BCR-ABL mutations. However, cellular ABL plays an important role in cellular DNA damage repair and treatment with STI-571 will also inhibit ABL and inactivate cellular DNA repair system. Most of the cellular ROS is produced by electron transport chain of active mitochondrial metabolism. PGC-1α is a master activator for mitochodrial biogenesis and respiration that promotes ROS production. SIRT1 plays a critical role in this regulation by deacetylating PGC-1α and thus activating its function. STI-571 treatment inhibits BCR-ABL function and cell growth but simultaneously reduces ability of cellular DNA damage repair and results in T315I mutation, unless SIRT1 is inactivated by sirtinol or PGC-1α is inactivated.

Example 12

Specific roles of BCR-ABL and SIRT1 for resistance of T315I mutant CML. Next examined was whether mutant BCR-ABL remains a major factor for resistance by using shRNA to knockdown BCR-ABL in KCL-22M cells and studying its effect on growth and apoptosis in the presence and absence of SIRT1 knockdown. KCL-22 cells express e13a2 (or b2a2) splice variant of p210 BCR-ABL, which can be knocked down with siRNAs designed against the fusion site. Several sets of shRNA were designed and tested against this region and make lentiviral vectors to knockdown BCR-ABL in KCL-22M with similar strategies used for SIRT1 knockdown. The efficiency of knockdown by Western blot was monitored with an antibody recognizing both c-ABL and BCR-ABL. shRNA knocks down BCR-ABL but not c-ABL. The effects of BCR-ABL knockdown on growth and apoptosis of KCL-22M cells were then determined in the presence or absence of SIRT1 shRNA knockdown.

Example 13

Roles of Aurora A for resistance of T315I mutant CML. Aurora kinases are evolutionarily conserved family of serine/threonine kinases, with three homologous genes Aurora A, B, and C in mammals. Aurora A is essential for bipolar spindle assembly during mitosis and Aurora B ensures proper chromosome attachment to the mitotic spindle, while Aurora C is involved in regulation of cilia and flagella. Aurora A is over-expressed in various types of human cancer and its gene amplification overrides the mitotic spindle assembly checkpoint, results in defective spindle formation and multinucleation, and increases cellular resistance to chemotherapeutic agent paclitaxel. Selective inhibitors of Aurora kinases have been developed for treatment of various cancers.

Figure 16:
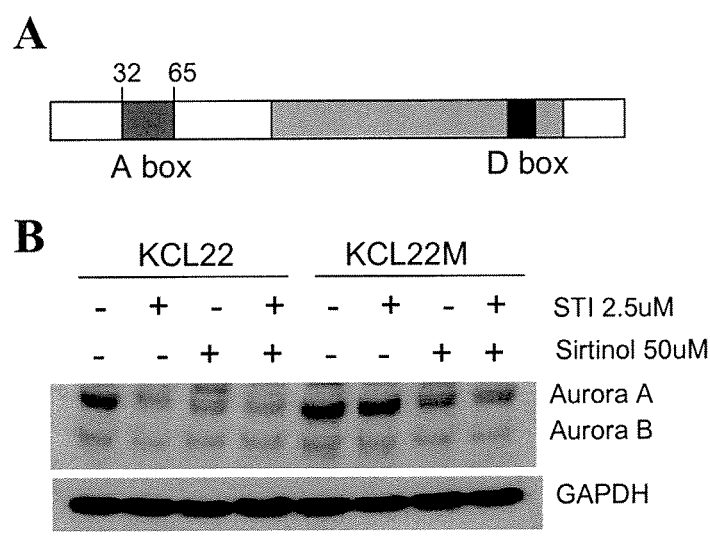
FIG. 16 illustrates expression of Aurora kinases in KCL-22 and KCL-22M cells.

The increase of G2/M cell number, enlarged cell size and bizarre morphology of KCL-22M cells show potential defects in cell mitosis, which will deregulate Aurora kinases in these cells. Using Western blot, it was found that the overall level of Aurora B in KCL-22 and KCL-22M cells are similar, but Aurora A was abnormally stabilized in KCL-22M cells that might account for morphological and cell cycle changes in these cells (FIG. 16). It has been found that the Aurora kinase inhibitor, VX-680, potently inhibits T315I BCR-ABL through a different structural mechanism from STI-571. Three CML patients with T315I mutation responded to VX-680 treatment, indicating that clinical responses of CML patients with T315I can be enhanced with inhibition of Aurora kinases, mutant BCR-ABL, or both. Aurora kinase plays a role in the resistance of T315I mutation in CML cells. VX-680 is a useful approach for eradicating mutant cells. Aurora A is abnormally stabilized in KCL-22M cells that have been treated with STI-571, but is degraded by treatment with SIRT1 inhibitor sirtinol (FIG. 16B). Abnormal stabilization of Aurora A can be caused by mutations of its DNA sequences for destruction boxes A and D (FIG. 16A) due to the pressure imposed by STI-571 treatment. Where inhibition of BCR-ABL alone is insufficient to eradicate T315I BCR-ABL mutant cells, combination treatment with SIRT1 inhibitors along with a dual BCR-ABL and Aurora inhibitor such as VX-680 is useful for eradicating the resistant cells.

Whether stabilization of Aurora A in KCL-22M cells might be due to alterations of its destruction signals is determined. Aurora A is destructed after mitotic exit through ubiquibin ligase, which is regulated by two conserved short amino acid sequences, an N-terminal A box and a C-terminal D box (FIG. 16A), and mutations of these sequences stabilize Aurora A. Besides, phosphorylation of serine S51 in the A box of human Aurora A or S53 in Xenopus also inhibits its destruction. There is structural similarity of kinase domains of BCR-ABL and Aurora, and cross reactivity of their inhibitors. These results show that Aurora A is involved in resistance of KCL-22M cells.

The effects of Aurora A knockdown for KCL-22M cells was also determined. Aurora A shRNAs was designed and tested. The knockdown of Aurora A was confirmed by Western blot. Whether this knockdown reduces G2/M cell population and restores normal cell morphology in KCL-22M cells by flow cytometry, and whether it promotes apoptosis or inhibits growth of KCL-22M cells is also assessed.

To determine the role of Aurora A over-expression in CML chemoresistance, Aurora A is expressed with an exogenous promoter in KCL-22 cells to examine whether it accelerated resistance, and in STI-571 sensitive K562 cells to examine whether it helped these cells to develop resistance. Wild type and/or mutant Aurora A is used depending on the sequencing results from the first experiment. Full length cDNA of Aurora A was PCR-amplified and subcloned into an expression cassette with Simian virus 40 (SV40) promoter in a lentiviral vector carrying CMV-GFP, which is similar to the vector used for shRNA packaging. When a mutant is needed, site-directed mutagenesis is performed in the subcloned Aurora A vector. Recombinant viruses are then produced and used to infect KCL-22 or K-562 cells, and over-expression of Aurora A is verified by Western blot. Infected cells are isolated by FACS sorting for GFP expression, and if necessary, cloning of individual cells. Resistance in these cells was measured by rate of mutation, time for relapse, and concentrations of STI571 needed to repress cell growth and induce apoptosis.

Knockdown of BCR-ABL has a greater impact on KCL-22 cells than KCL-22M cells, and other gene changes such as Aurora A also have important roles in resistance of KCL-22M cells. Over-expression of Aurora A can render KCL-22 cells more resistant to STI-571 treatment and may develop resistant cells even without genetic mutations, and persistent Aurora A may also render K-562 cells resistant to 1 μM STI-571 treatment. Simultaneous knockdown of BCR-ABL and Aurora A can have a more significant impact than individual knockdown on cell growth and apoptosis of KCL-22M cells. Treatment with VX-680 kills KCL-22M and KCL-22 cells efficiently as it inhibits both Aurora kinases and wild type or T315I BCR-ABL.

Example 14

SIRT1 is required for STI-571 resistance in mouse models and in primary human CML cells. It is examined whether the mechanisms that SIRT1 inhibition enhances CML apoptosis and prevents relapse on STI-571 in vitro applies to in vivo treatment. First, a xenograft model of human CML cells was used in non-obese diabetic severe combined immunodeficient (NOD-SCID) mice and examined whether the combined treatment with sirtinol and STI-571 eliminates KCL-22 cells in recipient mice and prolongs their survival without relapse. Also examined was another CML cell line KU-812 for xenograft study. KU-812 is very sensitive to STI-571 in vitro, but in vivo one third of mice with KU-812 xenograft relapse on STI-571 treatment after 48 to 60 days. It is determined whether the combination of STI-571 and sirtinol blocks this relapse. Second, murine bone marrow retroviral transduction and transplantation model was used to define specific roles of SIRT1 in vivo for BCR-ABL transformation and STI-571 resistance with SIRT1 knockout mice. Many hallmarks of human CML are faithfully reproduced in BALB/c mouse models employing retroviral transduction of bone marrow cells with P210 BCR-ABL followed by transplantation to syngeneic recipients. Mice develop CML-like myeloproliferative disease characterized by massive extramedullary hematopoiesis in spleen, liver and bone marrow with striking peripheral blood granulocytosis, and die within 3-4 weeks after transplantation. Treatment with STI-571 prolongs survival in 80% of mice, while the rest exhibit primary resistance and no mice can be cured by the treatment. It is examined whether homozygous SIRT1 knockout inhibits development of myeloproliferative disease in this model or significantly enhances the effects of STI-571 treatment to inhibit resistance and even cure the disease, and whether combination of sirtinol and STI-571 will significantly improve treatment of the disease generated with wild type mouse bone marrow. In vitro colony-forming-unit (CFU) assay is used to determine whether combination of sirtinol with STI-571 will suppress blast-forming unit-erythroid (BFU-E) and CFU-granulocyte-monocyte (CFU-GM) colonies from late phase CML patients more efficiently than STI-571 itself.

Since no animal studies have been conducted with sirtinol before, the pharmacokinetics of the compound was first determined. Female NOD-SCID mice 6 to 8 weeks of age were given a single dose of sirtinol intraperitoneally (i.p.) and at seven time points, namely 0.5, 1, 2, 4, 6, 8, and 24 hours, mice are sacrificed and blood, bone marrow and liver are collected for HPLC-MS analysis.

Figure 17:
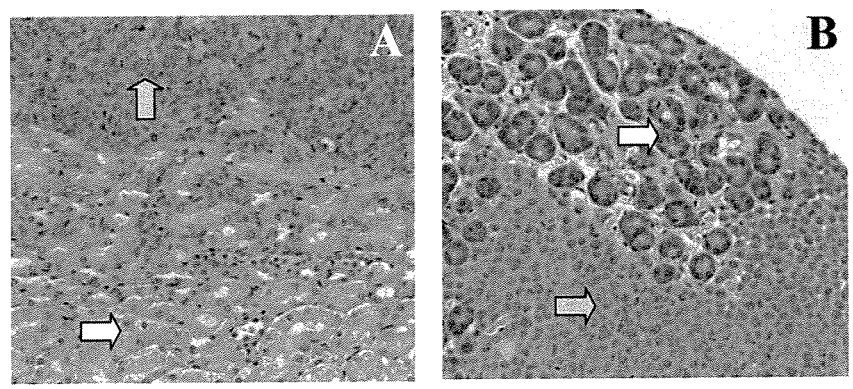
FIG. 17 shows a xenograft of human KCL-22 CML cells in NOD-SCID mice. The KCL-22 leukemia cells (shaded arrows) infiltrate kidney (FIG. 17A) and pancreas (FIG. 17B). Normal surrounding tissues are indicated by clear arrows for kidney (FIG. 17A) and pancreatic acini (FIG. 17B).

Second, the effects of the combination of sirtinol and STI-571 for treatment of xenografted CML cells were determined. Induction of tumors by KCL-22 cells in NOD-SCID mice was tested. Mice were irradiated with 270 Rads, and 4 to 6 hours later, transplanted with 3 million cells in phosphate-buffered saline each through tail vein. Of 12 recipients, one died within one week likely due to infection and the other 11 recipients developed tumors between 3 to 5 weeks. Most of mice exhibited visible tumors on neck, eye, and abdomen. Necropsy and histopathological examination revealed that these solid tumors were derived from lymph nodes throughout the body, with the highest frequency in axillary, pancreatic and renal nodes, and tumors frequently infiltrated kidney, eye and muscle (FIG. 17). A significant number of human cells were not detected in peripheral blood by flow cytometric analysis of CD45+ cells in all 11 mice before they were sacrificed for tumor burden. Microscopically visible tumors were not found in the spleen, liver and lung.

To facilitate non-invasive assessment of in vivo anti-tumor activity of drugs, KCL-22 cells stably expressing firefly luciferase were generated. Cells were examined for their responses for STI-571 and sirtinol treatment to ensure that luciferase expression does not alter effects of drugs. Luciferase-expressing KCL-22 cells are transplanted into NOD-SCID mice. Mice with established tumors (by luciferase imaging) are divided into 4 groups with 5 mice each: group 1, vehicle control; group 2, oral administration of STI-571 twice daily with a morning dose of 50 mg/kg and an evening dose of 100 mg/kg; group 3, single i.p. injection of sirtinol with a dose producing stable plasma concentration of at least 50 µM; group 4, combination of STI-571 and sirtinol. Mice were imaged 5 to 7 days after treatment, and total body bioluminescence was collected to quantify the changes of tumor progression and regression.

Example 15

Inhibition of Acquired Resistance in Other Human Cancers

Acquired resistance through secondary mutations on the targeted oncogenes are also predominant in other cancers, such as c-Kit receptor and the platelet-derived growth factor receptor (PDGFR) in gastrointestinal stromal tumors, and epidermal growth factor receptor (EGFR) in non-small cell lung cancer (NSCLC). SIRT1 in NSCLC resistance with and without secondary mutations would be assessed in cell lines H3255 and H1650. The H3255 line carries activating mutation L858R and the H1650 cells carry activating deletion (E746-A750) on the EGFR kinase domain, which render these cells sensitive to treatment with EGFR inhibitors gefitinib and erlotinib. Both cell lines can relapse upon gefitinib treatment, and H3255 cells develop resistance with the secondary T790M mutation (Engelman et al., 2006. Allelic dilution obscures detection of a biologically significant resistance mutation in EGFR-amplified lung cancer. J Clin Invest 116: 2695-2706) whereas H1650 cells develop resistance through mechanisms other than secondary mutations (Kwak et al., 2005. Irreversible inhibitors of the EGF receptor may circumvent acquired resistance to gefitinib. Proc Natl Acad Sci U S A 102:7665-7670.) A previous H1650 resistance model was derived by exposing cells directly to 20 µM gefitinib and a H3255 model was derived by exposing cells to gradually increasing concentrations of gefitinib (starting with 40 nM) for a few months. For patients receiving gefitinib 250 mg/d, the mean steady-state plasma concentration of the drug ranges from 0.4 to 1.4 µM, and higher concentrations of gefitinib result in off-target effects and toxicity (Cohen et al., 2004. United States Food and Drug Administration Drug Approval summary: Gefitinib (ZD1839; Iressa) tablets. Clin Cancer Res 10:1212-1218; Baselga et al., 2002. Phase I safety, pharmacokinetic, and pharmacodynamic trial of ZD1839, a selective oral epidermal growth factor receptor tyrosine kinase inhibitor, in patients with five selected solid tumor types. J Clin Oncol 20:4292-4302.). These previous methods did not use therapeutically effective concentrations of gefitinib. The NSCLC model provided herein employs approaches as those used in the described CML model studies.

NSCLC resistant models. $2.5 \times 10^5$ cells of H3255 or H1650 per well are seeded in 6-well plates. Multiple wells of each cell line are plated to allow sampling of cells at different time points. After overnight seeding, cells are treated with 1 µM gefitinib, or a therapeutically effective dose. The drug is maintained in the culture until cells relapse and re-grow as described for the CML studies. Fresh medium is supplied to restore the original volume during the prolonged culture as needed. Relative cell numbers are measured at various time points by staining cells with crystal violet and quantifying cell mass with Infrared Imaging System.

The relapsed cells are expanded and tested for their resistance to gefitinib as compared to parental cells. Total RNA is extracted for synthesis of cDNA and sequencing of EGFR kinase domain (exons 18-24), and genomic DNA is extracted for direct sequencing to verify mutations detected by cDNA sequencing using primers described previously (Pao et al., PNAS 101:13306-13311, 2004). Because H3255 harbors more than 40 copies of EGFR that results in allelic dilution of the T790M mutation, a mutant-enriched PCR sequencing assay is used to detect the mutation. (Inukai et al., Cancer Res 66:7854-7858, 2006). Briefly, after round one of amplification of both wild type and mutant alleles, the wild type PCR products are selectively cleaved by restriction enzyme BstUI, which allows second round preferential amplification of the mutant allele for sequencing. The mutant-enriched PCR sequencing assay can detect one mutant allele among 1000 copies of wild type alleles, and thus is sensitive enough for analysis of T790M mutation in H3255 cells. Using the above described method, genetic mutants in the NSCLC acquired resistant cells are identified.

Effects of SIRT1 inhibition on NSCLC resistance. SIRT1 expression levels in lung cancer cells are assessed. SIRT1 protein level was previously found increased in lung cancer cell lines H460 and H209 that bear wild type EGFR. SIRT1 expression in H3255 and H1650 cells before and after relapse, as compared to normal human lung lysates, will be analyzed by Western blot. Combination treatment of sirtinol at various concentrations with 1 µgefitinib may enhance apoptosis and inhibit growth of H3255 and H1650 cells. The apoptosis is analyzed by TUNEL staining and growth inhibition analyzed by crystal violet staining described above. The combination of the two drugs to block relapse of these two cell lines will be examined for the prolonged culture up to two months. Third, mock and SIRT1 knockdown are generated in H3255 and H1650 NSCLC cells using lentiviral shRNA vectors developed for CML resistance studies as described above. The knockdown of SIRT1 is confirmed by Western blotting. Whether SIRT1 knockdown delays or blocks relapse of NSCLC cells upon gefitinib treatmentis examined.

Methods: H3255 cell line is obtained from National Cancer Institute and H1650 cell line from American Type Culture Collection (ATCC). Gefitinib is obtained from AstraZeneca or purchased from Euroasia Pharmaceuticals, and sirtinol will be purchased from Sigma. For resistance assay, $2.5\times10^5$ H3255 or H1650 cells are seeded per well in 6-well plates overnight, and treat with drugs in 3 ml culture medium each. Cells are maintained in culture without medium changes. Relative cell numbers are analyzed over time in triplicate wells. Cells are fixed with 4% formaldehyde, stained with 0.1% crystal violet and quantified by using Odyssey Infrared Imaging System (LI-COR Biosciences). When relapse occurs, emerging cells reach confluence rapidly and are expanded into larger culture dishes. If the H3255 cells are unable to survive the applied dosage of gefitinib, then a lower therapeutic dose is used such as 0.4 µM, or the lowest therapeutically effective dose.

Total RNA and DNA are isolated using standard protocols. For sequencing the EGFR kinase domain, the EGFR kinase domain is amplified by RT-PCR of total RNA or by PCR of genomic DNA with a high fidelity DNA polymerase (Strategene) using primers previously described (Pao et al., 2004). PCR products are cloned into the pCR2.1 vector using TOPO TA Cloning kit (Invitrogen). At least ten clones for each treatment are sequenced. For mutant-enriched PCR sequencing of T790M mutation, the EGFR exon 20 is amplified using primers described (Inukai et al., 2006). After digestion of the first round PCR product with BstUI (NEB), the second round nested PCR is performed and the PCR products are sequenced directly.

For production of lentiviral vectors, four million 293T cells are co-transfected with 15 µg of the vector, 15 µg of gag-pol, 5 µg of VSV-G, and 5 µg of Rev plasmids by the method of calcium phosphate co-precipitation (Kowolik, C. M., P. Yam, Y. Yu, and J. K. Yee. 2003. HIV vector production mediated by Rev protein transduction. *Mol Ther* 8:324-331). The supernatant is collected at 24 hours and 36 hours after transfection. The supernatants are pooled and passed through a 0.45 um filter, concentrated by ultracentrifugation. To determine vector titer, $1\times10^5$ 293T cells are seeded in a six-well plate in the presence of 4 mg/ml polybrene, and cells are transduced for 5 hours and analyzed by FACS for GFP expression within 24 hours.

For protein analysis by Western blot, the following antibodies are used: rabbit monoclonal anti-SIRT1 (1:5000, Epitomics), and anti-GAPDH (1:5000, Trevigen). Apoptosis analysis was performed using a TMR-red In situ Cell Death Detection Kit (Roche) as per manufacturer's protocol. Normal human lung lysate are purchased from ProSci.

Using the above procedures, resistance models may be reproduced for H1650 cells. In addition, a faster relapse for H3255 cells with T790M mutation may be obtained (e.g. in two weeks). Inhibition of SIRT1 by sirtinol or by shRNA may have a synergistic or additive effect with gefitinib for inducing apoptosis and suppressing growth. The relapse normally obtained through mutation or non-mutation mechanisms will be blocked or delayed.

The resistance models may be also reproduced for other cancer cell lines, such as for example, another NSCLC cell line PC-9 that also relapses on gefitinib treatment.

Example 16

Methods

Cell culture and drugs. CML cell lines KCL-22 and K562 were purchased from German Collection of Cell Cultures, Braunschweig, Germany, and grown in RPMI 1640 medium with 10% fetal bovine serum (Hyclone). STI-571 was provided by Novartis, Basel, Switzerland; 6-thioguanine (6-TG) was purchased from Sigma and 2.5 µg/ml final concentration was used for selection. Sirtinol, splitomicin, nicotinamide, trichostatin A, 5-aza-2-deoxycytidine and HAT were purchased from Sigma. For serum-free culture, basic supplements (ITS 1-1884), EGF and HDL were purchased from Sigma and insulin from Roche.

Resistance Assay $5\times10^5$ KCL-22 or K562 cells in 1 ml medium per well in 24-well plates, and treated with various combinations of drugs. Cells were maintained in these cultures without changing medium. Aliquots of cells at specified time points were removed and cell numbers were counted on a hematocytometer. Cell viability was assessed by trypan blue exclusion whenever necessary. Typically, after three to five weeks in culture when their medium volume significantly decreased, fresh drug-free medium was supplied to the cells.

Soft agar colony formation assay. A standard two-layer soft agar culture was performed with a bottom layer of 0.7% agarose and top layer of 0.35% agarose. Five hundred cells per well in 6-well plates were seeded with warm top agar and were incubated for three weeks. Plates were then stained with 0.005% Crystal Violet for 1 hour, and colonies were scored with aid of microscope. For resistance assay in soft agar, one million cells were added per well and imatinib or 6-TG added to both top and bottom agar to their final concentrations. To clone or recover soft agar colonies for further analysis, individual colonies were plucked and expanded in liquid culture.

Cell cycle, cell proliferation and apoptosis analysis Cell cycle was analyzed by fixing cells with 70% ethanol and then staining with propidine iodine (50 µg/ml) for 30 min at room temperature. Cell proliferation was analyzed using a XTT Cell Proliferation kit (Roche), and apoptosis was analyzed with annexin V kit (BD Pharmingen) as per the manufacturer's instruction.

Sequencing ABL kinase domain [SEQ ID NO: 17] and HPRT [SEQ ID NO: 12]

The ABL kinase domain [SEQ ID NO: 17] was amplified by RT-PCR of total RNA or by PCR of genomic DNA with a high fidelity DNA polymerase (Strategene) using primers previously described (Gorre et al., 2001). PCR products were cloned into the pCR2.1 vector using TOPO TA Cloning kit (Invitrogen). At least ten clones for each treatment were sequenced. For analysis of genomic DNA mutations PCR products were directly sequenced without subcloning. For HPRT sequencing, the codon sequence was amplified by RT-PCR using primers previously described (Osterholm et al., 1995). PCR products were purified with a PCR product clean-up kit (Qiagen) and sequenced directly.

PRIMERS

Sequencing primers for the 579 bp kinase domain using cDNA templates:

```
                                          [SEQ ID NO: 5]
   Forward primer: 5' GCGCAACAAGCCCACTGTCTATGG 3'

[SEQ ID NO: 6]
   Reverse primer: 5' GCCAGGCTCTCGGGTGCAGTCC 3'
```

For nested RT-PCR from BCR-ABL junction, the forward primer is

```
                                          [SEQ ID NO: 18]
        5' GAAGCTTCTCCCTGACATCCGT,
```

Sequencing primers for T315I mutation using genomic templates:

```
                                    [SEQ ID NO: 19]
Forward primer A: 5'-GCAGAGTCAGAATCCTTCAG-3'

[SEQ ID NO: 20]
Forward primer B: 5'-GAGCCACGTGTTGAAGTCCT-3'

[SEQ ID NO: 21]
Reverse primer: 5'-TTTGTAAAAGGCTGCCCGGC-3'
```

Additional primers for BCR-ABL kinase domain sequencing:

```
                                    [SEQ ID NO: 22]
Forward primers: GCCTGTCTCTGTGGGCTGAAG

[SEQ ID NO: 23]
Reverse primer: CAAGGCGTCTGCTGGCATTA
```

Two primers for sequencing genomic templates for E255 [SEQ ID NO: 3] and Y253 [SEQ ID NO: 4] mutations:

```
                                    [SEQ ID NO: 22]
Forward: 5'-GCCTGTCTCTGTGGGCTGAAG-3'

[SEQ ID NO: 24]
Reverse: 5'-TAATGCCAGCAGACGCCTTG-3'
```

Primers for sequencing HPRT cDNA:

```
                                    [SEQ ID NO: 13]
Forward: 5'-ACCGGCTTCCTCCTCCTGAG-3'

[SEQ ID NO: 14]
Reverse: 5'-GATAATTTTACTGGCGATGT-3'
```

III. Real-time PCR primers
GAPDH [>ref|NT_009759.15|Hs12_9916:6497433-6502281 Homo sapiens chromosome 12 genomic contig, reference assembly]

```
                                    [SEQ ID NO: 25]
Forward: 5'-GGAAGGTGAAGGTCGGAGTC-3'

[SEQ ID NO: 26]
Reverse: 5'-TTCCCGTTCTCAGCCTTGAC-3'
```

HIC1[>ref|NT_010718.15|Hs17_10875:1561637-1565694 Homo sapiens chromosome 17 genomic contig, reference assembly]

```
                                    [SEQ ID NO: 15]
Forward (1a): 5'-GGACGGACCAGCAGGACA-3'

[SEQ ID NO: 16]
Reverse (1b): 5'-GCGCTGGTTGTTGAGCTG-3
```

SIRT1 shRNAs
ACCESSION AF083106, Homo sapiens sirtuin type 1 (SIRT1) mRNA, complete cds.
Sh1:

Sense
                                    [SEQ ID NO: 27]
5'TGTTGACCTCCTCATTGTTATTCAAGAGATAACAATGAGGAGGTCAA

CTTTTTT3'

Anti sense
                                    [SEQ ID NO: 28]
5'TCGAGAAAAAAGTTGACCTCCTCATTGTTATCTCTTGAATAACAATG

AGGAGGTCAACA-3'

Sh2:

Sense
                                    [SEQ ID NO: 29]
5'TGTTGGATGATATGACACTGTTCAAGAGACAGTGTCATATCATCCAA

CTTTTTT3'

Anti sense
                                    [SEQ ID NO: 30]
5'TCGAGAAAAAAGTTGGATGATATGACACTGTCTCTTGAACAGTGTCA

TATCATCCAACA-3'

Cell cloning by limiting dilution

Cells were counted and diluted to 5 cells per ml, and seeded onto 96-well plate with 100 µl (or 0.5 cell) per well. Individual cell seeding was then confirmed by microscopy, and single cell clones were grown and expanded for further analysis.

Immunoprecipitation and Western blot alalysis

BCR-ABL expression and phosphorylation were directly analyzed by Western blot using anti-c-ABL monoclonal antibody (BD Pharmingen) and anti phospho-tyrosine antibody (Upstate Biotechnology). To validate BCR-ABL phosphorylation, BCR-ABL from 500 µg of total cell lysate of KCL-22 cells was isolated with 2 µg of anti-c-ABL and 100 µl of 50% slurry of protein A-agarose beads (Upstate). The phosphorylation was detected by Western blot with tyrosine phosphorylation antibody. GAPDH was analyzed as a loading control using a rabbit antibody (Trevigen) at 1:5000 dilution.

Gene Expression Analysis. Total cellular RNA with Trizol (Invitrogen) using a standard protocol. First strand DNA was synthesized and HIC1expression by quantitative real-time RT-PCR using a kit with SYBR Green label (Invitrogen) as per the manufacture's instruction on a BioRad machine OPTICON. The following are the HIC1primers (spanning introns), 5'-GGACGGACCAGCAGGACA-3' (exon 1a) [SEQ ID NO: 15] and 5'-GCGCTGGTTGTTGAGCTG-3' (Exon 2) [SEQ ID NO: 16]. SIRT1 expression was analyzed by Western blot using 1:5000 diluted rabbit monoclonal SIRT1 antibody (Epitomics). Controls used were GAPDH or actin as loading controls with rabbit anti-GAPDH (Trevigen) or anti-actin (Sigma) at 1:5000 dilution.

Production of lentiviral vectors Lentiviral vectors were produced as previously described (Kowolik et al., 2003). In brief, four million 293T cells are co-transfected with 15 µg of the vector, 15 µmg of gag-pol, 5 µg of VSV-G, and 5 µg of Rev plasmids by the method of calcium phosphate coprecipitation. The supernatant is collected at 24 hours and 36 hours after transfection. The supernatants are pooled and passed through a 0.45 µm filter, concentrated by ultracentrifugation. To determine vector titer, we seed $1 \times 10^5$ 293T cells in a six-well plate in the presence of 4 µg/ml polybrene, and cells are transduced for 5 hours and analyzed by FACS for GFP expression within 24 hours.

DNA damage assay. The assay was performed as described (Xiao et al., 2003). KCL-22 cells were pre-selected for four days in HAT medium to remove pre-existing HPRT mutations. The efficiency of HAT selection was confirmed by plating these cells on soft agar with 2.5 µg/ml 6-thioguanine, which produced zero colony. HAT-selected cells were then treated with 0.5 µM CPT for 1 hour and used for soft agar clonogenic assay with 6-thioguanine. The rest of HAT-selected cells were cultured in medium without selection. Soft agar colonies were scored after three weeks as described (Yuan et al., 2008).

References

Anand, S., S. Penrhhyn-Lowe, and A. R. Venkitaraman. 2003. AURORA-A amplification overrides the mitotic spindle assembly checkpoint, inducing resistance to Taxol. Cancer Cell 3:51-62.

Andrews, P. D. 2005. Aurora kinases: shining lights on the therapeutic horizon? Oncogene 24:5005-5015.

Avalos, J. L., Bever, K. M., and Wolberger, C. (2005). Mechanism of sirtuin inhibition by nicotinamide: altering the NAD(+) cosubstrate specificity of a Sir2 enzyme. Mol Cell 17, 855-868.

Balaban, R. S., S, Nemoto, and T. Finkel. 2005. Mitochondria, oxidants, and aging. Cell 120:483-495.

Baselga, J. 2006. Targeting tyrosine kinases in cancer: the second wave. Science 312:1175-1178.

Baselga, J., D. Rischin, M. Ranson, H. Calvert, E. Raymond, D. G. Kieback, S. B. Kaye, L. Gianni, A. Harris, T. Bjork, S. D. Averbuch, A. Feyereislova, H. Swaisland, F. Rojo, and J. Albanell. 2002. Phase I safety, pharmacokinetic, and pharmacodynamic trial of ZD1839, a selective oral epidermal growth factor receptor tyrosine kinase inhibitor, in patients with five selected solid tumor types. J Clin Oncol 20:4292-4302.

Bassan, R., Gatta, G., Tondini, C., and Willemze, R. (2004). Adult acute lymphoblastic leukaemia. Crit. Rev Oncol Hematol 50, 223-261.

Baur, J. A., K. J. Pearson, N. L. Price, H. A. Jamieson, C. Lerin, A. Kalra, V. V. Prabhu, J. S. Allard, G. Lopez-Lluch, K. Lewis, P. J. Pistell, S. Poosala, K. G. Becker, O. Boss, D. Gwinn, M. Wang, S. Ramaswamy, K. W. Fishbein, R. G. Spencer, E. G. Lakatta, D. Le Couteur, R. J. Shaw, P. Navas, P. Puigserver, D. K. Ingram, R. de Cabo, and D. A. Sinclair. 2006. Resveratrol improves health and survival of mice on a high-calorie diet. Nature 444:337-342.

Bedalov, A., T. Gatbonton, W. P. Irvine, D. E. Gottschling, and J. A. Simon. 2001. Identification of a small molecule inhibitor of Sir2p. Proc Natl Acad Sci USA 98:15113-15118.

Bi, S., T. Hughes, J. Bungey, A. Chase, P. de Fabritiis, and J. M. Goldman. 1992. p53 in chronic myeloid leukemia cell lines. Leukemia 6:839-842.

Bitterman, K. J., R. M. Anderson, H. Y. Cohen, M. Latorre-Esteves, and D. A. Sinclair. 2002. Inhibition of silencing and accelerated aging by nicotinamide, a putative negative regulator of yeast sir2 and human SIRT1. J Biol Chem 277:45099-45107.

Blume-Jensen, P., and T. Hunter. 2001. Oncogenic kinase signalling. Nature 411:355-365.

Bordone, L., Motta, M. C., Picard, F., Robinson, A., Jhala, U.S., Apfeld, J., McDonagh, T., Lemieux, M., McBurney, M., Szilvasi, A., et al. (2006). Sirt1 regulates insulin secretion by repressing UCP2 in pancreatic beta cells. PLoS Biol 4, e31.

Branford, S., Z. Rudzki, S. Walsh, A. Grigg, C. Arthur, K. Taylor, R. Herrmann, K. P. Lynch, and T. P. Hughes. 2002. High frequency of point mutations clustered within the adenosine triphosphate-binding region of BCR/ABL in patients with chronic myeloid leukemia or Ph-positive acute lymphoblastic leukemia who develop imatinib (STI571) resistance. Blood 99:3472-3475.

Brunet, A., Sweeney, L. B., Sturgill, J. F., Chua, K. F., Greer, P. L., Lin, Y., Tran, H., Ross, S. E., Mostoslaysky, R., Cohen, H. Y., et al. (2004). Stress-dependent regulation of FOXO transcription factors by the SIRT1 deacetylase. Science 303, 2011-2015.

Burchert, A., Wang, Y., Cai, D., von Bubnoff, N., Paschka, P., Muller-Brusselbach, S., Ottmann, O. G., Duyster, J., Hochhaus, A., and Neubauer, A. (2005). Compensatory PI3-kinase/Akt/mTor activation regulates imatinib resistance development. Leukemia 19, 1774-1782.

Burkhart-Schultz, K. J., Thompson, C. L., and Jones, I. M. (1996). Spectrum of somatic mutation at the hypoxanthine phosphoribosyltransferase (hprt) gene of healthy people. Carcinogenesis 17, 1871-1883.

Canitrot, Y., Lautier, D., Laurent, G., Frechet, M., Ahmed, A., Turhan, A. G., Salles, B., Cazaux, C., and Hoffmann, J. S. (1999). Mutator phenotype of BCR—ABL transfected Ba/F3 cell lines and its association with enhanced expression of DNA polymerase beta. Oncogene 18, 2676-2680.

Carter, M. G., M. A. Johns, X. Zeng, L. Zhou, M. C. Zink, J. L. Mankowski, D. M. Donovan, and S. B. Baylin. 2000. Mice deficient in the candidate tumor suppressor gene Hic1 exhibit developmental defects of structures affected in the Miller-Dieker syndrome. Hum Mol Genet. 9:413-419.

Carter, T. A., L. M. Wodicka, N. P. Shah, A. M. Velasco, M. A. Fabian, D. K. Treiber, Z. V. Milanov, C. E. Atteridge, W. H. Biggs, 3rd, P. T. Edeen, M. Floyd, J. M. Ford, R. M. Grotzfeld, S. Herrgard, D. E. Insko, S. A. Mehta, H. K. Patel, W. Pao, C. L. Sawyers, H. Varmus, P. P. Zarrinkar, and D. J. Lockhart. 2005. Inhibition of drug-resistant mutants of ABL, KIT, and EGF receptor kinases. Proc Natl Acad Sci USA 102:11011-11016.

Chen, P. M., Kwan, S. H., Hwang, T. S., Chiang, B. N., and Chou, C. K. (1983). Insulin receptors on leukemia and lymphoma cells. Blood 62, 251-255.

Chen, W. Y., and Baylin, S. B. (2005). Inactivation of Tumor Suppressor Genes: Choice Between Genetic and Epigenetic Routes. Cell Cycle 4.

Chen, W. Y., Cooper, T. K., Zahnow, C. A., Overholtzer, M., Zhao, Z., Ladanyi, M., Karp, J. E., Gokgoz, N., Wunder, J. S., Andrulis, I. L., et al. (2004). Epigenetic and genetic loss of Hic1 function accentuates the role of p53 in tumorigenesis. Cancer Cell 6, 387-398.

Chen, W. Y., D. H. Wang, R. C. Yen, J. Luo, W. Gu, and S. B. Baylin. 2005. Tumor suppressor HIC1 directly regulates SIRT1 to modulate p53-dependent DNA-damage responses. Cell 123:437-448.

Chen, W. Y., Zeng, X., Carter, M. G., Morrell, C. N., Chiu Yen, R. W., Esteller, M., Watkins, D. N., Herman, J. G., Mankowski, J. L., and Baylin, S. B. (2003). Heterozygous disruption of Hic1 predisposes mice to a gender-dependent spectrum of malignant tumors. Nat Genet. 33, 197-202.

Chu, F., P. M. Chou, X. Zheng, B. L. Mirkin, and A. Rebbaa. 2005. Control of multidrug resistance gene mdr1 and cancer resistance to chemotherapy by the longevity gene sirt1. Cancer Res 65:10183-10187.

Cohen, H. Y., Miller, C., Bitterman, K. J., Wall, N. R., Hekking, B., Kessler, B., Howitz, K. T., Gorospe, M., de Cabo, R., and Sinclair, D. A. (2004). Calorie restriction promotes mammalian cell survival by inducing the SIRT1 deacetylase. Science 305, 390-392.

Cohen, M. H., G. A. Williams, R. Sridhara, G. Chen, W. D. McGuinn, Jr., D. Morse, S. Abraham, A. Rahman, C. Liang, R. Lostritto, A. Baird, and R. Pazdur. 2004. United States Food and Drug Administration Drug Approval summary: Gefitinib (ZD1839; Iressa) tablets. Clin Cancer Res 10:1212-1218.

Cragg, M. S., J. Kuroda, H. Puthalakath, D. C. Huang, and A. Strasser. 2007. Gefitinib-induced killing of NSCLC cell lines expressing mutant EGFR requires BIM and can be enhanced by BH3 mimetics. PLoS Med 4:1681-1689; discussion 1690.

Crane, R., A. Kloepfer, and J. V. Ruderman. 2004. Requirements for the destruction of human Aurora-A. J Cell Sci 117:5975-5983.

Czechowska, A., Poplawski, T., Drzewoski, J., and Blasiak, J. (2005). Imatinib (STI571) induces DNA damage in BCR/ABL-expressing leukemic cells but not in normal lymphocytes. Chem Biol Interact 152, 139-150.

Daitoku, H., M. Hatta, H. Matsuzaki, S. Aratani, T. Ohshima, M. Miyagishi, T. Nakajima, and A. Fukamizu. 2004. Silent information regulator 2 potentiates Foxo1-mediated transcription through its deacetylase activity. Proc Natl Acad Sci USA 101:10042-10047.

de Ruijter, A. J., van Gennip, A. H., Caron, H. N., Kemp, S., and van Kuilenburg, A. B. (2003). Histone deacetylases (HDACs): characterization of the classical HDAC family. Biochem J 370, 737-749.

Deininger, M. W., and Druker, B. J. (2003). Specific targeted therapy of chronic myelogenous leukemia with imatinib. Pharmacol Rev 55, 401-423.

Deininger, M. W., Goldman, J. M., Lydon, N., and Melo, J. V. (1997). The tyrosine kinase inhibitor CGP57148B selectively inhibits the growth of BCR-ABL-positive cells. Blood 90, 3691-3698.

Engelman, J. A., K. Zejnullahu, T. Mitsudomi, Y. Song, C. Hyland, J. O. Park, N. Lindeman, C. M. Gale, X. Zhao, J. Christensen, T. Kosaka, A. J. Holmes, A. M. Rogers, F. Cappuzzo, T. Mok, C. Lee, B. E. Johnson, L. C. Cantley, and P. A. Janne. 2007. MET amplification leads to gefitinib resistance in lung cancer by activating ERBB3 signaling. Science 316: 1039-1043.

Engelman, J. A., T. Mukohara, K. Zejnullahu, E. Lifshits, A. M. Borras, C. M. Gale, G. N. Naumov, B. Y. Yeap, E. Jarrell, J. Sun, S. Tracy, X. Zhao, J. V. Heymach, B. E. Johnson, L. C. Cantley, and P. A. Janne. 2006. Allelic dilution obscures detection of a biologically significant resistance mutation in EGFR-amplified lung cancer. J Clin Invest 116: 2695-2706.

Ford, J., M. Jiang, and J. Milner. 2005. Cancer-specific functions of SIRT1 enable human epithelial cancer cell growth and survival. Cancer Res 65:10457-10463.

Frye, R. A. 1999. Characterization of five human cDNAs with homology to the yeast SIR2 gene: Sir2-like proteins (sirtuins) metabolize NAD and may have protein ADP-ribosyltransferase activity. Biochem Biophys Res Commun 260: 273-279.

Frye, R. A. 2000. Phylogenetic classification of prokaryotic and eukaryotic Sir2-like proteins. Biochem Biophys Res Commun 273:793-798.

Gambacorti-Passerini, C. B., Gunby, R. H., Piazza, R., Galietta, A., Rostagno, R., and Scapozza, L. (2003). Molecular mechanisms of resistance to imatinib in Philadelphia-chromosome-positive leukaemias. Lancet Oncol 4, 75-85.

Giles, F. J., Cortes, J., Jones, D., Bergstrom, D., Kantarjian, H., and S. J. Freedman. 2007. MK-0457, a novel kinase inhibitor, is active in patients with chronic myeloid leukemia or acute lymphocytic leukemia with the T315I BCR-ABL mutation. Blood 109:500-502.

Gorre, M. E., Mohammed, M., Ellwood, K., Hsu, N., Paquette, R., Rao, P. N., and Sawyers, C. L. (2001). Clinical resistance to STI-571 cancer therapy caused by BCR-ABL gene mutation or amplification. Science 293, 876-880.

Grozinger, C. M., E. D. Chao, H. E. Blackwell, D. Moazed, and S. L. Schreiber. 2001. Identification of a class of small molecule inhibitors of the sirtuin family of NAD-dependent deacetylases by phenotypic screening. J Biol Chem 276: 38837-38843.

Guarente, L. 2000. Sir2 links chromatin silencing, metabolism, and aging. Genes Dev 14:1021-1026.

Guerardel, C., Deltour, S., Pinte, S., Monte, D., Begue, A., Godwin, A. K., and Leprince, D. (2001). Identification in the human candidate tumor suppressor gene HIC-1 of a new major alternative TATA-less promoter positively regulated by p53. J Biol Chem 276, 3078-3089.

Haber, D. A., D. W. Bell, R. Sordella, E. L. Kwak, N. Godin-Heymann, S. V. Sharma, T. J. Lynch, and J. Settleman. 2005. Molecular targeted therapy of lung cancer: EGFR mutations and response to EGFR inhibitors. Cold Spring Harb Symp Quant Biol 70:419-426.

Harrington, E. A., D. Bebbington, J. Moore, R. K. Rasmussen, A. O. Ajose-Adeogun, T. Nakayama, J. A. Graham, C. Demur, T. Hercend, A. Diu-Hercend, M. Su, J. M. Golec, and K. M. Miller. 2-4. VX-680, a potent and selective small-molecule inhibitor of the Aurora kinases, suppresses tumor growth in vivo. Nat Med 10:262-267.

Hirao, M., Posakony, J., Nelson, M., Hruby, H., Jung, M., Simon, J. A., and Bedalov, A. (2003). Identification of selective inhibitors of NAD+-dependent deacetylases using phenotypic screens in yeast. J Biol Chem 278, 52773-52782.

Howitz, K. T., K. J. Bitterman, H. Y. Cohen, D. W. Lamming, S. Lavu, J. G. Wood, R. E. Zipkin, P. Chung, A. Kisielewski, L. L. Zhang, B. Scherer, and D. A. Sinclair. 2003. Small molecule activators of sirtuins extend *Saccharomyces cerevisiae* lifespan. Nature 425:191-196.

Huffman, D. M., W. E. Grizzle, M. M. Bamman, J. S. Kim, I. A. Eltoum, A. Elgavish, and T. R. Nagy. 2007. SIRT1 Is Significantly Elevated in Mouse and Human Prostate Cancer. Cancer Res 67:6612-6618.

Imai, S., C. M. Armstrong, M. Kaeberlein, and L. Guarente. 2000. Transcriptional silencing and longevity protein Sir2 is an NAD-dependent histone deacetylase. Nature 403:795-800.

Inukai, M., S. Toyooka, S. Ito, H. Asano, S. Ichihara, J. Soh, H. Suchisa, M. Ouchida, K. Aoe, M. Aoe, K. Kiura, N. Shimizu, and H. Date. 2006. Presence of epidermal growth factor receptor gene T790M mutation as a minor clone in non-small cell lung cancer. Cancer Res 66:7854-7858.

Issa, J. P., Zehnbauer, B. A., Kaufmann, S. H., Biel, M. A., and Baylin, S. B. (1997). HIC1 hypermethylation is a late event in hematopoietic neoplasms. Cancer Res 57, 1678-1681.

Jones, P. A., and Baylin, S. B. (2002). The fundamental role of epigenetic events in cancer. Nat Rev Genet. 3, 415-428.

Kaeberlein, M., McVey, M., and Guarente, L. (1999). The SIR2/3/4 complex and SIR2 alone promote longevity in *Saccharomyces cerevisiae* by two different mechanisms. Genes Dev 13, 2570-2580.

Kantarjian, H., Giles, F., Wunderle, L., Bhalla, K., O'Brien, S., Wassmann, B., Tanaka, C., Manley, P., Rae, P., Mietlowski, W., et al. (2006). Nilotinib in imatinib-resistant CML and Philadelphia chromosome-positive ALL. N Engl J Med 354, 2542-2551.

Kawano, T., Horiguchi-Yamada, J., (wase, S., Akiyama, M., Furukawa, Y., Kan, Y., and Yamada, H. (2004). Depsipeptide enhances imatinib mesylate-induced apoptosis of Bcr-Abl-positive cells and ectopic expression of cyclin D1, c-Myc or active MEK abrogates this effect. Anticancer Res 24, 2705-2712.

Keen, N., and S. Taylor. 2004. Aurora-kinase inhibitors as anticancer agents. Nat Rev Cancer 4:927-936.

Kelly, D. P., and R. C. Scarpulla. 2004. Transcriptional regulatory circuits controlling mitochondrial biogenesis and function. Genes Dev 18:357-368.

Kharbanda, S., P. Pandey, S. Jin, S. Inoue, A. Bharti, Z. M. Yuan, R. Weichselbaum, D. Weaver, and D. Kufe. 1997. Functional interaction between DNA-PK and c-Abi in response to DNA damage. Nature 386:732-735.

Klejman, A., Rushen, L., Morrione, A., Slupianek, A., and Skorski, T. (2002). Phosphatidylinositol-3 kinase inhibitors enhance the anti-leukemia effect of STI571. Oncogene 21, 5868-5876.

Kobayashi, S., T. J. Boggon, T. Dayaram, P. A. Janne, O. Kocher, M. Meyerson, B. E. Johnson, M. J. Eck, D. G. Tenen, and B. Halmos. 2005. EGFR mutation and resistance of non-small-cell lung cancer to gefitinib. N Engl J Med 352:786-792.

Koptyra, M., R. Falinski, M. O. Nowicki, T. Stoklosa, I. Majsterek, M. Nieborowska-Skorska, J. Blasiak, and T. Skorski. 2006. BCR/ABL kinase induces self-mutagenesis via reactive oxygen species to encode imatinib resistance. Blood 108:319-327.

Kosaka, T., Y. Yatabe, H. Endoh, K. Yoshida, T. Hida, M. Tsuboi, H. Tada, H. Kuwano, and T. Mitsudomi. 2006. Analysis of epidermal growth factor receptor gene mutation in patients with non-small cell lung cancer and acquired resistance to gefitinib. Clin Cancer Res 12:5764-5769.

Kowolik, C. M., Yam, P., Yu, Y., and Yee, J. K. (2003). HIV vector production mediated by Rev protein transduction. Mol Ther 8, 324-331.

Kuzmichev, A., R. Margueron, A. Vaquero, T. S. Preissner, M. Scher, A. Kirmizis, X. Ouyang, N. Brockdorff, C. Abate-Shen, P. Farnham, and D. Reinberg. 2005. Composition and histone substrates of polycomb repressive group complexes change during cellular differentiation. Proc Natl Acad Sci USA 102:1859-1864.

Kwak, E. L., R. Sordella, D. W. Bell, N. Godin-Heymann, R. A. Okimoto, B. W. Brannigan, P. L. Harris, D. R. Driscoll, P. Fidias, T. J. Lynch, S. K. Rabindran, J. P. McGinnis, A. Wissner, S. V. Sharma, K. J. Isselbacher, J. Settleman, and D. A. Haber. 2005. Irreversible inhibitors of the EGF receptor may circumvent acquired resistance to gefitinib. Proc Natl Acad Sci USA 102:7665-7670.

Lagouge, M., C. Argmann, Z. Gerhart-Hines, H. Meziane, C. Lerin, F. Daussin, N. Messadeq, J. Milne, P. Lambert, P. Elliott, B. Geny, M. Laakso, P. Puigserver, and J. Auwerx. 2006. Resveratrol improves mitochondrial function and protects against metabolic disease by activating SIRT1 and PGC-1 alpha. Cell 127:1109-1122.

La Rosee, P., Corbin, A. S., Stoffregen, E. P., Deininger, M. W., and Druker, B. J. (2002). Activity of the Bcr-Abl kinase inhibitor PD180970 against clinically relevant Bcr-Abl isoforms that cause resistance to imatinib mesylate (Gleevec, STI571). Cancer Res 62, 7149-7153.

La Rosee, P., Johnson, K., Corbin, A. S., Stoffregen, E. P., Moseson, E. M., Willis, S., Mauro, M. M., Melo, J. V., Deininger, M. W., and Druker, B. J. (2004). In vitro efficacy of combined treatment depends on the underlying mechanism of resistance in imatinib-resistant Bcr-Abl-positive cell lines. Blood 103, 208-215.

La Rosee, P., Corbin, A. S., Stoffregen, E. P., Deininger, M. W., and Druker, B. J. (2002). Activity of the Bcr-Abl kinase inhibitor PD180970 against clinically relevant Bcr-Abl isoforms that cause resistance to imatinib mesylate (Gleevec, STI571). Cancer Res 62, 7149-7153.

Landry, J., A. Sutton, S. T. Tafrov, R. C. Heller, J. Stebbins, L. Pillus, and R. Sternglanz. 2000. The silencing protein SIR2 and its homologs are NAD-dependent protein deacetylases. Proc Natl Acad Sci USA 97:5807-5811.

Le Coutre, P., L. Mologni, L. Cleros, E. Marchesi, E. Buchdunger, R. Giardini, F. Formelli, and C. Gambacorti-Passerini. 1999. In vivo eradication of human BCR/ABL-positive leukemia cells with an ABL kinase inhibitor. J Natl Cancer Inst 91:163-168.

Li, M. J., G. Bauer, A. Michienzi, J. K. Yee, N. S. Lee, J. Kim, S. Li, D. Castanotto, J. Zaia, and J. J. Rossi. 2003. Inhibition of HIV-1 infection by lentiviral vectors expressing Pol III-promoted anti-HIV RNAs. Mol Ther 8:196-206.

Lin, S. J., P. A. Defossez, and L. Guarente. 2000. Requirement of NAD and SIR2 for life-span extension by calorie restriction in Saccharomyces cerevisiae. Science 289:2126-2128.

Littlepage, L. E., and J. V. Ruderman. 2002. Identification of a new APC/C recognition domain, the A box, which is required for the Cdh1-dependent destruction of the kinase Aurora-A during mitotic exit. Genes Dev 16:2274-2285.

Littlepage, L. E., H. Wu, T. Andresson, J. K. Deanehan, L. T. Amundadottir, and J. V. Ruderman. 2002. Identification of phosphorylated residues that affect the activity of the mitotic kinase Aurora-A. Proc Natl Acad Sci USA 99:15440-15445.

Luo, J., Nikolaev, A. Y., Imai, S., Chen, D., Su, F., Shiloh, A., Guarente, L., and Gu, W. (2001). Negative control of p53 by Sir2alpha promotes cell survival under stress. Cell 107, 137-148.

Ly, C., Arechiga, A. F., Melo, J. V., Walsh, C. M., and Ong, S. T. (2003). Bcr-Abl kinase modulates the translation regulators ribosomal protein S6 and 4E-BP1 in chronic myelogenous leukemia cells via the mammalian target of rapamycin. Cancer Res 63, 5716-5722.

Lynch, T. J., D. W. Bell, R. Sordella, S. Gurubhagavatula, R. A. Okimoto, B. W. Brannigan, P. L. Harris, S. M. Haserlat, J. G. Supko, F. G. Haluska, D. N. Louis, D. C. Christiani, J. Settleman, and D. A. Haber. 2004. Activating mutations in the epidermal growth factor receptor underlying responsiveness of non-small-cell lung cancer to gefitinib. N Engl J Med 350:2129-2139.

Maguer-Satta, V., Burl, S., Liu, L., Damen, J., Chahine, H., Krystal, G., Eaves, A., and Eaves, C. (1998). BCR-ABL accelerates C2-ceramide-induced apoptosis. Oncogene 16, 237-248.

Mahon, F. X., Deininger, M. W., Schultheis, B., Chabrol, J., Reiffers, J., Goldman, J. M., and Melo, J. V. (2000). Selection and characterization of BCR-ABL positive cell lines with differential sensitivity to the tyrosine kinase inhibitor STI571: diverse mechanisms of resistance. Blood 96, 1070-1079.

Mai, A., S. Massa, S. Lavu, R. Pezzi, S. Simeoni, R. Ragno, F. R. Mariotti, F. Chiani, G. Camilloni, and D. A. Sinclair. 2005. Design, synthesis, and biological evaluation of sirtinol analogues as class III histone/protein deacetylase (Sirtuin) inhibitors. J Med Chem 48:7789-7795.

Marumoto, T., D. Zhang, and H. Saya. 2005. Aurora-A—a guardian of poles. Nat Rev Cancer 5:42-50.

Michor, F., Hughes, T. P., Iwasa, Y., Branford, S., Shah, N. P., Sawyers, C. L., and Nowak, M. A. (2005). Dynamics of chronic myeloid leukaemia. Nature 435, 1267-1270.

Motta, M. C., N. Divecha, M. Lemieux, C. Kamel, D. Chen, W. Gu, Y. Bultsma, M. McBurney, and L. Guarente. 2004. Mammalian SIRT1 represses forkhead transcription factors. Cell 116:551-563.

Moynihan, K. A., Grimm, A. A., Plueger, M. M., Bernal-Mizrachi, E., Ford, E., Cras-Meneur, C., Permutt, M. A., and Imai, S. (2005). Increased dosage of mammalian Sir2 in pancreatic beta cells enhances glucose-stimulated insulin secretion in mice. Cell Metab 2, 105-117.

Narayan, G., Arias-Pulido, H., Koul, S., Vargas, H., Zhang, F. F., Villella, J., Schneider, A., Terry, M. B., Mansukhani, M., and Murty, V. V. (2003). Frequent Promoter Methylation of CDH1, DAPK, RARB, and HIC1 Genes in Carcinoma of Cervix Uteri: Its Relationship to Clinical Outcome. Mol Cancer 2, 24.

Nemoto, S., M. M. Fergusson, and T. Finkel. 2004. Nutrient availability regulates SIRT1 through a forkhead-dependent pathway. Science 306:2105-2108.

Neubauer, A., M. He, C. A. Schmidt, D. Huhn, and E. T. Liu. 1993. Genetic alterations in the p53 gene in the blast crisis of chronic myelogenous leukemia: analysis by polymerase chain reaction based techniques. Leukemia 7:593-600.

North, B. J., and Verdin, E. (2004). Sirtuins: Sir2-related NAD-dependent protein deacetylases. Genome Biol 5, 224.

Ogino, A., H. Kitao, S. Hirano, A. Uchida, M. Ishiai, T. Kozuki, N. Takigawa, M. Takata, K. Kiura, and M. Tanimoto. 2007. Emergence of epidermal growth factor receptor T790M mutation during chronic exposure to gefitinib in a non small cell lung cancer cell line. Cancer Res 67:7807-7814.

Osterholm, A. M., Falt, S., Lambert, B., and Hou, S. M. (1995). Classification of mutations at the human hprt-locus in T-lymphocytes of bus maintenance workers by multiplex-PCR and reverse transcriptase-PCR analysis. Carcinogenesis 16, 1909-1912.

Ota, H., Tokunaga, E., Chang, K., Hikasa, M., Iijima, K., Eto, M., Kozaki, K., Akishita, M., Ouchi, Y., and Kaneki, M. (2005). Sirt1 inhibitor, Sirtinol, induces senescence-like growth arrest with attenuated Ras-MAPK signaling in human cancer cells. Oncogene.

Paez, J. G., P. A. Janne, J. C. Lee, S. Tracy, H. Greulich, S. Gabriel, P. Herman, F. J. Kaye, N. Lindeman, T. J. Boggon, K. Naoki, H. Sasaki, Y. Fujii, M. J. Eck, W. R. Sellers, B. E. Johnson, and M. Meyerson. 2004. EGFR mutations in lung cancer: correlation with clinical response to gefitinib therapy. Science 304:1497-1500.

Pan, J., Q. Wang, and W. J. Snell. 2004. An aurora kinase is essential for flagellar disassembly in Chlamydomonas. Dev Cell 6:445-451.

Pao, W., V. A. Miller, K. A. Politi, G. J. Riely, R. Somwar, M. F. Zakowski, M. G. Kris, and H. Varmus. 2005. Acquired resistance of lung adenocarcinomas to gefitinib or erlotinib is associated with a second mutation in the EGFR kinase domain. PLoS Med 2:e73.

Pao, W., V. Miller, M. Zakowski, J. Doherty, K. Politi, I. Sarkaria, B. Singh, R. Heelan, V. Rusch, L. Fulton, E. Mardis, D. Kupfer, R. Wilson, M. Kris, and H. Varmus. 2004. EGF receptor gene mutations are common in lung cancers from "never smokers" and are associated with sensitivity of tumors to gefitinib and erlotinib. Proc Natl Acad Sci USA 101:13306-13311.

Pear, W. S., J. P. Miller, L. Xu, J. C. Pui, B. Soffer, R. C. Quackenbush, A. M. Pendergast, R. Bronson, J. C. Aster, M. L. Scott, and D. Baltimore. 1998. Efficient and rapid induction of a chronic myelogenous leukemia-like myeloproliferative disease in mice receiving P210 bcr/abl-transduced bone marrow. Blood 92:3780-3792.

Peng, B., P. Lloyd, and H. Schran. 2005. Clinical pharmacokinetics of imatinib. Clin Pharmacokinet 44:879-894.

Podlutsky, A., Osterholm, A. M., Hou, S. M., Hofmaier, A., and Lambert, B. (1998). Spectrum of point mutations in the coding region of the hypoxanthine-guanine phosphoribosyltransferase (hprt) gene in human T-lymphocytes in vivo. Carcinogenesis 19, 557-566.

Rapozzi, V., and L. E. Xodo. 2004. Efficient silencing of bcr/abl oncogene by single- and double-stranded siRNAs targeted against b2a2 transcripts. Biochemistrry 43:16134-16141.

Rathi, A., Virmani, A. K., Harada, K., Timmons, C. F., Miyajima, K., Hay, R. J., Mastrangelo, D., Maitra, A., Tomlinson, G. E., and Gazdar, A. F. (2003). Aberrant methylation of the HIC1 promoter is a frequent event in specific pediatric neoplasms. Clin Cancer Res 9, 3674-3678.

Reynolds, A., Leake, D., Boese, Q., Scaringe, S., Marshall, W. S., and Khvorova, A. (2004). Rational siRNA design for RNA interference. Nat Biotechnol 22, 326-330.

Rodgers, J. T., C. Lerin, W. Haas, S. P. Gygi, B. M. Spiegelman, and P. Puigserver. 2005. Nutrient control of glucose homeostasis through a complex of PGC-1 alpha and SIRT1. Nature 434:113-118.

Santini, V., Kantarjian, H. M., and Issa, J. P. (2001). Changes in DNA methylation in neoplasia: pathophysiology and therapeutic implications. Ann Intern Med 134, 573-586.

Sattler, M., S. Verma, G. Shrikhande, C. H. Byrne, Y. B. Pride, T. Winkler, E. A. Greenfield, R. Salgia, and J. D. Griffin. 2000. The BCR/ABL tyrosine kinase induces production of reactive oxygen species in hematopoietic cells. J Biol Chem 275:24273-24278.

Saunders, L. R., and Verdin, E. (2007). Sirtuins: critical regulators at the crossroads between cancer and aging. Oncogene 26, 5489-5504.

Schindler, T., Bornmann, W., Pellicena, P., Miller, W. T., Clarkson, B., and Kuriyan, J. (2000). Structural mechanism for STI-571 inhibition of abelson tyrosine kinase. Science 289, 1938-1942.

Shafman, T., K. K. Khanna, P. Kedar, K. Spring, S. Kozlov, T. Yen, K. Hobson, M. Gatei, N. Zhang, D. Watters, M. Egerton, Y. Shiloh, S. Kharbanda, D. Kufe, and M. F. Lavin. 1997. Interaction between ATM protein and c-Abl in response to DNA damage. Nature 387:520-523.

Shah, N. P., and Sawyers, C. L. (2003). Mechanisms of resistance to STI571 in Philadelphia chromosome-associated leukemias. Oncogene 22, 7389-7395.

Shah, N. P., C. Tran, F. Y. Lee, P. Chen, D. Norris, and C. L. Sawyers. 2004. Overriding imatinib resistance with a novel ABL kinase inhibitor. Science 305:399-401.

Shah, N. P., Nicoll, J. M., Nagar, B., Gorre, M. E., Paquette, R. L., Kuriyan, J., and Sawyers, C. L. (2002). Multiple BCR-ABL kinase domain mutations confer polyclonal resistance to the tyrosine kinase inhibitor imatinib (STI571) in chronic phase and blast crisis chronic myeloid leukemia. Cancer Cell 2, 117-125.

Skorski, T., Kanakaraj, P., Nieborowska-Skorska, M., Ratajczak, M. Z., Wen, S. C., Zon, G., Gewirtz, A. M., Perussia, B., and Calabretta, B. (1995). Phosphatidylinositol-3 kinase activity is regulated by BCR/ABL and is required for the growth of Philadelphia chromosome-positive cells. Blood 86, 726-736.

Slupianek, A., Nowicki, M. O., Koptyra, M., and Skorski, T. (2006). BCR/ABL modifies the kinetics and fidelity of DNA double-strand breaks repair in hematopoietic cells. DNA Repair (Amst) 5, 243-250.

Soverini, S., Colarossi, S., Gnani, A., Rosti, G., Castagnetti, F., Poerio, A., Iacobucci, I., Amabile, M., Abruzzese, E., Orlandi, E., et al. (2006). Contribution of ABL kinase domain mutations to imatinib resistance in different subsets of Philadelphia-positive patients: by the GIMEMA Working Party on Chronic Myeloid Leukemia. Clin Cancer Res 12, 7374-7379.

Stamos, J., M. X. Sliwkowski, and C. Eigenbrot. 2002. Structure of the epidermal growth factor receptor kinase domain alone and in complex with a 4-anilinoquinazoline inhibitor. J Biol Chem 277:46265-46272.

Szabo, Tang, Reed, Silva, Tsark, Mann. 2002. The chicken beta-globin insulator element conveys chromatin boundary activity but not imprinting at the mouse Igf2/H19 domain. Development 129:897-904.

Talpaz, M., N. P. Shah, H. Kantarjian, N. Donato, J. Nicoll, R. Paquette, J. Cortes, S. O'Brien, C. Nicaise, E. Bleickardt, M. A. Blackwood-Chirchir, V. Iyer, T. T. Chen, F. Huang, A. P. Decillis, and C. L. Sawyers. 2006. Dasatinib in imatinib-resistant Philadelphia chromosome-positive leukemias. N Engl J Med 354:2531-2541.

Tang, S. H., F. J. Silva, W. M. Tsark, and J. R. Mann. 2002. A Cre/loxP-deleter transgenic line in mouse strain 129S1/SvImJ. Genesis 32:199-202.

Tanner, K. G., J. Landry, R. Sternglanz, and J. M. Denu. 2000. Silent information regulator 2 family of NAD-dependent histone/protein deacetylases generates a unique product, 1-O-acetyl-ADP-ribose. Proc Natl Acad Sci USA 97:14178-14182.

Tanny, J. C., and D. Moazed. 2001. Coupling of histone deacetylation to NAD breakdown by the yeast silencing protein Sir2: Evidence for acetyl transfer from substrate to an NAD breakdown product. Proc Natl Acad Sci USA 98:415-420.

Tissenbaum, H. A., and Guarente, L. (2001). Increased dosage of a sir-2 gene extends lifespan in *Caenorhabditis elegans*. Nature 410, 227-230.

van der Horst, A., L. G. Tertoolen, L. M. de Vries-Smits, R. A. Frye, R. H. Medema, and B. M. Burgering. 2004. FOXO4 is acetylated upon peroxide stress and deacetylated by the longevity protein hSir2 (SIRT1). J Biol Chem 279:28873-28879.

Vaziri, H., Dessain, S. K., Ng Eaton, E., Imai, S. I., Frye, R. A., Pandita, T. K., Guarente, L., and Weinberg, R. A. (2001). hSIR2 (SIRT1) functions as an NAD-dependent p53 deacetylase. Cell 107, 149-159.

Ventura, A., Meissner, A., Dillon, C. P., McManus, M., Sharp, P. A., Van Parijs, L., Jaenisch, R., and Jacks, T. (2004). Cre-lox-regulated conditional RNA interference from transgenes. Proc Natl Acad Sci USA 101, 10380-10385.

von Bubnoff, N., C. Peschel, and J. Duyster. 2003. Resistance of Philadelphia-chromosome positive leukemia towards the kinase inhibitor imatinib (STI571, Glivec): a targeted oncoprotein strikes back. Leukemia 17:829-838.

von Bubnoff, N., D. R. Veach, H. van der Kuip, W. E. Aulitzky, J. Sanger, P. Seipel, W. G. Bornmann, C. Peschel, B. Clarkson, and J. Duyster. 2005. A cell-based screen for resistance of Bcr-Abl-positive leukemia identifies the mutation pattern for PD166326, an alternative Abl kinase inhibitor. Blood 105:1652-1659.

von Bubnoff, N., Manley, P. W., Mestan, J., Sanger, J., Peschel, C., and Duyster, J. (2006). Bcr-Abl resistance screening predicts a limited spectrum of point mutations to be associated with clinical resistance to the Abl kinase inhibitor nilotinib (AMN107). Blood 108, 1328-1333.

Wales, M. M., M. A. Biel, W. el Deiry, B. D. Nelkin, J. P. Issa, W. K. Cavenee, S. J. Kuerbitz, and S. B. Baylin. 1995. p53 activates expression of HIC-1, a new candidate tumour suppressor gene on 17p13.3. Nat Med 1:570-577.

Weisberg, E., Manley, P. W., Breitenstein, W., Bruggen, J., Cowan-Jacob, S. W., Ray, A., Huntly, B., Fabbro, D., Fendrich, G., Hall-Meyers, E., et al. (2005). Characterization of AMN107, a selective inhibitor of native and mutant Bcr-Abl. Cancer Cell 7, 129-141.

Woo, R. A., and Poon, R. Y. (2004). Activated oncogenes promote and cooperate with chromosomal instability for neoplastic transformation. Genes Dev 18, 1317-1330.

Wood, J. G., B. Rogina, S. Lavu, K. Howitz, S. L. Helfand, M. Tatar, and D. Sinclair. 2004. Sirtuin activators mimic caloric restriction and delay ageing in metazoans. Nature 430:686-689.

Xiao, H., Li, T. K., Yang, J. M., and Liu, L. F. (2003). Acidic pH induces topoisomerase II-mediated DNA damage. Proc Natl Acad Sci USA 100, 5205-5210.

Yu, C., Rahmani, M., Almenara, J., Subler, M., Krystal, G., Conrad, D., Varticovski, L., Dent, P., and Grant, S. (2003). Histone deacetylase inhibitors promote STI571-mediated apoptosis in STI571-sensitive and -resistant Bcr/Abl+human myeloid leukemia cells. Cancer Res 63, 2118-2126.

Yuan, H. F., Bhatia, R., and Chen, W. Y. (2008). Induction of BCR-ABL mutations for acquired resistance of chronic myelogenous leukemia by imatinib To be submitted.

Yuan, Z., Zhang, X., Sengupta, N., Lane, W. S., and Seto, E. (2007). SIRT1 regulates the function of the Nijmegen breakage syndrome protein. Mol Cell 27, 149-162.

What is claimed is:

1. A method for treating cell resistance to chemotherapy or reducing relapse growth of a chronic myelogenous leukemia (CML) cancer cell comprising administering a therapeutically effective amount of a SIRT1 inhibitor and a therapeutically effective amount of one or more tyrosine kinase inhibitors selected from the group consisting of STI-571, imatinib, nilotinib, and VS-680 to the cell, wherein the SIRT1 inhibitor is sirtinol, splitomicin, nicotinamide, shRNA Sh1, shRNA Sh2, or a combination thereof, and wherein said administration results in reduced cell resistance to chemotherapy or reduced relapse growth of the CML cancer cell.

2. The method of claim 1, wherein the SIRT1 inhibitor is administered for the purpose of preventing the formation of one or more BCR-ABL mutations in the cell.

3. The method of claim 2, wherein if the tyrosine kinase inhibitor is imatinib or STI-571, the one or more BCR-ABL mutations are selected from the group consisting of T315I, E255K, and Y253H.

4. The method of claim 1, wherein the SIRT1 inhibitor is administered at or about the same time as the administration of the tyrosine kinase inhibitor.

5. The method of claim 1, wherein the SIRT1 inhibitor is administered prior to or subsequent to the administration of the tyrosine kinase inhibitor.

6. The method of claim 2, wherein the one or more tyrosine kinase inhibitors are imatinib and VX-680 or STI-571 and VX-680.

7. The method of claim 6, wherein the one or more BCR-ABL mutations is T315I.

* * * * *

SEQUENCE LISTING

<160> NUMBER OF SEQ ID NOS: 30

<210> SEQ ID NO 1
<211> LENGTH: 789
<212> TYPE: DNA
<213> ORGANISM: Homo sapiens

<400> SEQUENCE: 1

```
tgggagatgg aacgcacgga catcaccatg aagcacaagc tgggcggggg ccagtacggg      60
gaggtgtacg agggcgtgtg gaagaaatac agcctgacgg tggccgtgaa gaccttgaag     120
gaggacacca tggaggtgga agagttcttg aaagaagctg cagtcatgaa agagatcaaa     180
caccctaacc tggtgcagct ccttgggtc tgcacccggg agccccgtt ctatatcatc       240 actgagttca tgaccctacgg gaacctcctg gactacctga gggagtgcaa ccggcaggag   300
gtgaacgccg tggtgctgct gtacatggcc actcagatct cgtcagccat ggagtacctg     360
gagaagaaaa acttcatcca cagagatctt gctgcccgaa actgcctggt aggggagaac     420
cacttggtga aggtagctga ttttggcctg agcaggttga tgacagggga cacctacaca     480
gcccatgctg gagccaagtt ccccatcaaa tggactgcac ccgagagcct ggcctacaac     540
aagttctcca tcaagtccga cgtctgggca tttggagtat tgctttggga aattgctacc    600
```

```
tatggcatgt cccttaccc gggaattgac ctgtcccagg tgtatgagct gctagagaag    660
gactaccgca tggagcgccc agaaggctgc ccagagaagg tctatgaact catgcgagca    720
tgttggcagt ggaatccctc tgaccggccc tcctttgctg aaatccacca agcctttgaa    780
acaatgttc                                                            789
```

```
<210> SEQ ID NO 2
<211> LENGTH: 263
<212> TYPE: PRT
<213> ORGANISM: Homo sapiens

<400> SEQUENCE: 2
```

Trp Glu Met Glu Arg Thr Asp Ile Thr Met Lys His Lys Leu Gly Gly
1               5                   10                  15

Gly Gln Tyr Gly Glu Val Tyr Glu Gly Val Trp Lys Lys Tyr Ser Leu
            20                  25                  30

Thr Val Ala Val Lys Thr Leu Lys Glu Asp Thr Met Glu Val Glu Glu
        35                  40                  45

Phe Leu Lys Glu Ala Ala Val Met Lys Glu Ile Lys His Pro Asn Leu
    50                  55                  60

Val Gln Leu Leu Gly Val Cys Thr Arg Glu Pro Pro Phe Tyr Ile Ile
65                  70                  75                  80

Ile Glu Phe Met Thr Tyr Gly Asn Leu Leu Asp Tyr Leu Arg Glu Cys
                85                  90                  95

Asn Arg Gln Glu Val Asn Ala Val Val Leu Leu Tyr Met Ala Thr Gln
            100                 105                 110

Ile Ser Ser Ala Met Glu Tyr Leu Glu Lys Lys Asn Phe Ile His Arg
        115                 120                 125

Asp Leu Ala Ala Arg Asn Cys Leu Val Gly Glu Asn His Leu Val Lys
    130                 135                 140

Val Ala Asp Phe Gly Leu Ser Arg Leu Met Thr Gly Asp Thr Tyr Thr
145                 150                 155                 160

Ala His Ala Gly Ala Lys Phe Pro Ile Lys Trp Thr Ala Pro Glu Ser
                165                 170                 175

Leu Ala Tyr Asn Lys Phe Ser Ile Lys Ser Asp Val Trp Ala Phe Gly
            180                 185                 190

Val Leu Leu Trp Glu Ile Ala Thr Tyr Gly Met Ser Pro Tyr Pro Gly
        195                 200                 205

Ile Asp Arg Ser Gln Val Tyr Glu Leu Leu Lys Asp Tyr Arg Met
    210                 215                 220

Lys Arg Pro Glu Gly Cys Pro Glu Lys Val Tyr Glu Leu Met Arg Ala
225                 230                 235                 240

Cys Trp Gln Trp Asn Pro Ser Asp Arg Pro Ser Phe Ala Glu Ile His
                245                 250                 255

Gln Ala Phe Glu Thr Met Phe
            260

```
<210> SEQ ID NO 3
<211> LENGTH: 263
<212> TYPE: PRT
<213> ORGANISM: Homo sapiens

<400> SEQUENCE: 3
```

Trp Glu Met Glu Arg Thr Asp Ile Thr Met Lys His Lys Leu Gly Gly
1               5                   10                  15

```
Gly Gln Tyr Gly Glu Val Tyr Glu Gly Val Trp Lys Lys Tyr Ser Leu
            20                  25                  30

Thr Val Ala Val Lys Thr Leu Lys Glu Asp Thr Met Glu Val Glu Glu
        35                  40                  45

Phe Leu Lys Glu Ala Ala Val Met Lys Glu Ile Lys His Pro Asn Leu
 50                  55                  60

Val Gln Leu Leu Gly Val Cys Thr Arg Glu Pro Pro Phe Tyr Ile Ile
 65                  70                  75                  80

Thr Glu Phe Met Thr Tyr Gly Asn Leu Leu Asp Tyr Leu Arg Glu Cys
                85                  90                  95

Asn Arg Gln Glu Val Asn Ala Val Val Leu Leu Tyr Met Ala Thr Gln
            100                 105                 110

Ile Ser Ser Ala Met Glu Tyr Leu Glu Lys Lys Asn Phe Ile His Arg
        115                 120                 125

Asp Leu Ala Ala Arg Asn Cys Leu Val Gly Glu Asn His Leu Val Lys
130                 135                 140

Val Ala Asp Phe Gly Leu Ser Arg Leu Met Thr Gly Asp Thr Tyr Thr
145                 150                 155                 160

Ala His Ala Gly Ala Lys Phe Pro Ile Lys Trp Thr Ala Pro Glu Ser
                165                 170                 175

Leu Ala Tyr Asn Lys Phe Ser Ile Lys Ser Asp Val Trp Ala Phe Gly
            180                 185                 190

Val Leu Leu Trp Glu Ile Ala Thr Tyr Gly Met Ser Pro Tyr Pro Gly
        195                 200                 205

Ile Asp Arg Ser Gln Val Tyr Glu Leu Leu Glu Lys Asp Tyr Arg Met
210                 215                 220

Lys Arg Pro Glu Gly Cys Pro Glu Lys Val Tyr Glu Leu Met Arg Ala
225                 230                 235                 240

Cys Trp Gln Trp Asn Pro Ser Asp Arg Pro Ser Phe Ala Glu Ile His
                245                 250                 255

Gln Ala Phe Glu Thr Met Phe
            260

<210> SEQ ID NO 4
<211> LENGTH: 263
<212> TYPE: PRT
<213> ORGANISM: Homo sapiens

<400> SEQUENCE: 4

Trp Glu Met Glu Arg Thr Asp Ile Thr Met Lys His Lys Leu Gly Gly
 1               5                  10                  15

Gly Gln His Gly Glu Val Tyr Glu Gly Val Trp Lys Lys Tyr Ser Leu
            20                  25                  30

Thr Val Ala Val Lys Thr Leu Lys Glu Asp Thr Met Glu Val Glu Glu
        35                  40                  45

Phe Leu Lys Glu Ala Ala Val Met Lys Glu Ile Lys His Pro Asn Leu
 50                  55                  60

Val Gln Leu Leu Gly Val Cys Thr Arg Glu Pro Pro Phe Tyr Ile Ile
 65                  70                  75                  80

Thr Glu Phe Met Thr Tyr Gly Asn Leu Leu Asp Tyr Leu Arg Glu Cys
                85                  90                  95

Asn Arg Gln Glu Val Asn Ala Val Val Leu Leu Tyr Met Ala Thr Gln
            100                 105                 110

Ile Ser Ser Ala Met Glu Tyr Leu Glu Lys Lys Asn Phe Ile His Arg
        115                 120                 125
```

```
Asp Leu Ala Ala Arg Asn Cys Leu Val Gly Glu Asn His Leu Val Lys
            130                 135                 140

Val Ala Asp Phe Gly Leu Ser Arg Leu Met Thr Gly Asp Thr Tyr Thr
145                 150                 155                 160

Ala His Ala Gly Ala Lys Phe Pro Ile Lys Trp Thr Ala Pro Glu Ser
                165                 170                 175

Leu Ala Tyr Asn Lys Phe Ser Ile Lys Ser Asp Val Trp Ala Phe Gly
            180                 185                 190

Val Leu Leu Trp Glu Ile Ala Thr Tyr Gly Met Ser Pro Tyr Pro Gly
            195                 200                 205

Ile Asp Arg Ser Gln Val Tyr Glu Leu Leu Glu Lys Asp Tyr Arg Met
            210                 215                 220

Lys Arg Pro Glu Gly Cys Pro Glu Lys Val Tyr Glu Leu Met Arg Ala
225                 230                 235                 240

Cys Trp Gln Trp Asn Pro Ser Asp Arg Pro Ser Phe Ala Glu Ile His
                245                 250                 255

Gln Ala Phe Glu Thr Met Phe
            260
```

```
<210> SEQ ID NO 5
<211> LENGTH: 24
<212> TYPE: DNA
<213> ORGANISM: Artificial
<220> FEATURE:
<223> OTHER INFORMATION: forward primer

<400> SEQUENCE: 5
gcgcaacaag cccactgtct atgg                                          24

<210> SEQ ID NO 6
<211> LENGTH: 22
<212> TYPE: DNA
<213> ORGANISM: Artificial
<220> FEATURE:
<223> OTHER INFORMATION: reverse primer

<400> SEQUENCE: 6
gccaggctct cgggtgcagt cc                                            22

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
gcagagtcag aatccttcag                                               20

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
gagccacgtg ttgaagtcct                                               20

<210> SEQ ID NO 9
<211> LENGTH: 20
```

```
<212> TYPE: DNA
<213> ORGANISM: Artificial
<220> FEATURE:
<223> OTHER INFORMATION: primer

<400> SEQUENCE: 9
gccgggcagc cttttacaaa                                                 20

<210> SEQ ID NO 10
<211> LENGTH: 21
<212> TYPE: DNA
<213> ORGANISM: Artificial
<220> FEATURE:
<223> OTHER INFORMATION: forward primer

<400> SEQUENCE: 10
gcctgtctct gtgggctgaa g                                               21

<210> SEQ ID NO 11
<211> LENGTH: 20
<212> TYPE: DNA
<213> ORGANISM: Artificial
<220> FEATURE:
<223> OTHER INFORMATION: reverse primer

<400> SEQUENCE: 11
taatgccagc agacgccttg                                                 20

<210> SEQ ID NO 12
<211> LENGTH: 1307
<212> TYPE: DNA
<213> ORGANISM: Homo sapiens

<400> SEQUENCE: 12
tcttgctgcg cctccgcctc ctcctctgct ccgccaccgg cttcctcctc ctgagcagtc     60
agcccgcgcg ccggccggct ccgttatggc gacccgcagc cctggcgtcg tgattagtga    120
tgatgaacca ggttatgacc ttgatttatt ttgcatacct aatcattatg ctgaggattt    180
ggaaagggtg tttattcctc atggactaat tatggacagg actgaacgtc ttgctcgaga    240
tgtgatgaag gagatgggag ccatcacat tgtagccctc tgtgtgctca aggggggcta    300
taattctttg ctgacctgct ggattacatc aagcactgaa tagaatagtg atagatccat    360
tcctatgact gtagatttta tcagactgaa gagctattgt aatgaccagt caacagggga    420
cataaaagta attggtggag atgatctctc aactttaact ggaagaatgt cttgattgtg    480
gaagatataa ttgacactgg caaaacaatg cagactttgc tttccttggt caggcagtat    540
aatccaagat ggtcaaggtc gcaagcttgc tggtgaaagg accccacgaa gtgttggata    600
taagccagac tttgttggat tgaattccag acaagtttg ttgtaggata tgcccttgac     660
tataatgaat acttcaggga tttgaatcat gtttgtgtca ttagtgaact ggaaagcaaa    720
atacaagcct aagatgagag ttcaagttga gtttggaaca tctggagtcc tattgacatc    780
gccagtaaat tatcaatgtt ctagttctgt ggccatctgc ttagtagagc ttttgcatg    840 tatcttctaa gaattttatc tgttttgtac tttagaatgt cagttgctgc attcctaact    900
gtttatttgc actatgagcc tatagactat cagttcccctt tgggcggatt gttgtttaac    960
ttgtaatgaa aaaattctct taaccacagc actattgagt gaaacattga actcatatct   1020
gtaagaaata agagaagata tattagtttt ttaattggta tttttaatttt tatatatgca   1080 ggaagaatag aagtgattga atattgttaa ttataccacc gtgtgttaga agtaagaagc   1140
```

-continued agtcaattttt cacatcaaga cagcatctaa gaagttttgt tctgtcctgg aattatttta    1200
gtagtgtttc agtaatgttg actgtatttt ccaacttgtt caattattac cagtgaatct    1260
ttgtcagcag ttcccttta atgcaaatca ataaattccc aaaattt                   1307

<210> SEQ ID NO 13
<211> LENGTH: 20
<212> TYPE: DNA
<213> ORGANISM: Artificial
<220> FEATURE:
<223> OTHER INFORMATION: forward primer

<400> SEQUENCE: 13
accggcttcc tcctcctgag                                                20

<210> SEQ ID NO 14
<211> LENGTH: 20
<212> TYPE: DNA
<213> ORGANISM: Artificial
<220> FEATURE:
<223> OTHER INFORMATION: reverse primer

<400> SEQUENCE: 14
gataatttta ctggcgatgt                                                20

<210> SEQ ID NO 15
<211> LENGTH: 18
<212> TYPE: DNA
<213> ORGANISM: Artificial
<220> FEATURE:
<223> OTHER INFORMATION: forward primer

<400> SEQUENCE: 15
ggacggacca gcaggaca                                                  18

<210> SEQ ID NO 16
<211> LENGTH: 18
<212> TYPE: DNA
<213> ORGANISM: Artificial
<220> FEATURE:
<223> OTHER INFORMATION: reverse primer

<400> SEQUENCE: 16
gcgctggttg ttgagctg                                                  18

<210> SEQ ID NO 17
<211> LENGTH: 263
<212> TYPE: PRT
<213> ORGANISM: Homo sapiens

<400> SEQUENCE: 17

Trp Glu Met Glu Arg Thr Asp Ile Thr Met Lys His Lys Leu Gly Gly
1               5                   10                  15

Gly Gln Tyr Gly Glu Val Tyr Glu Gly Val Trp Lys Lys Tyr Ser Leu
            20                  25                  30

Thr Val Ala Val Lys Thr Leu Lys Glu Asp Thr Met Glu Val Glu Glu
        35                  40                  45

Phe Leu Lys Glu Ala Ala Val Met Lys Glu Ile Lys His Pro Asn Leu
    50                  55                  60

Val Gln Leu Leu Gly Val Cys Thr Arg Glu Pro Pro Phe Tyr Ile Ile
65                  70                  75                  80

Thr Glu Phe Met Thr Tyr Gly Asn Leu Leu Asp Tyr Leu Arg Glu Cys
                85                  90                  95

Asn Arg Gln Glu Val Asn Ala Val Leu Leu Tyr Met Ala Thr Gln
            100                 105                 110

Ile Ser Ser Ala Met Glu Tyr Leu Glu Lys Lys Asn Phe Ile His Arg
        115                 120                 125

Asp Leu Ala Ala Arg Asn Cys Leu Val Gly Glu Asn His Leu Val Lys
    130                 135                 140

Val Ala Asp Phe Gly Leu Ser Arg Leu Met Thr Gly Asp Thr Tyr Thr
145                 150                 155                 160

Ala His Ala Gly Ala Lys Phe Pro Ile Lys Trp Thr Ala Pro Glu Ser
                165                 170                 175

Leu Ala Tyr Asn Lys Phe Ser Ile Lys Ser Asp Val Trp Ala Phe Gly
            180                 185                 190

Val Leu Leu Trp Glu Ile Ala Thr Tyr Gly Met Ser Pro Tyr Pro Gly
        195                 200                 205

Ile Asp Arg Ser Gln Val Tyr Glu Leu Leu Glu Lys Asp Tyr Arg Met
    210                 215                 220

Lys Arg Pro Glu Gly Cys Pro Glu Lys Val Tyr Glu Leu Met Arg Ala
225                 230                 235                 240

Cys Trp Gln Trp Asn Pro Ser Asp Arg Pro Ser Phe Ala Glu Ile His
                245                 250                 255

Gln Ala Phe Glu Thr Met Phe
            260

<210> SEQ ID NO 18
<211> LENGTH: 22
<212> TYPE: DNA
<213> ORGANISM: Artificial
<220> FEATURE:
<223> OTHER INFORMATION: forward primer

<400> SEQUENCE: 18
gaagcttctc cctgacatcc gt                                        22

<210> SEQ ID NO 19
<211> LENGTH: 20
<212> TYPE: DNA
<213> ORGANISM: Artificial
<220> FEATURE:
<223> OTHER INFORMATION: forward primer

<400> SEQUENCE: 19
gcagagtcag aatccttcag                                           20

<210> SEQ ID NO 20
<211> LENGTH: 20
<212> TYPE: DNA
<213> ORGANISM: Artificial
<220> FEATURE:
<223> OTHER INFORMATION: forward primer

<400> SEQUENCE: 20
gagccacgtg ttgaagtcct                                           20

<210> SEQ ID NO 21
<211> LENGTH: 20
<212> TYPE: DNA
<213> ORGANISM: Artificial
<220> FEATURE:
<223> OTHER INFORMATION: reverse primer

<400> SEQUENCE: 21

```
tttgtaaaag gctgcccggc                                                    20

<210> SEQ ID NO 22
<211> LENGTH: 21
<212> TYPE: DNA
<213> ORGANISM: Artificial
<220> FEATURE:
<223> OTHER INFORMATION: forward primer

<400> SEQUENCE: 22
gcctgtctct gtgggctgaa g                                                  21

<210> SEQ ID NO 23
<211> LENGTH: 20
<212> TYPE: DNA
<213> ORGANISM: Artificial
<220> FEATURE:
<223> OTHER INFORMATION: reverse primer

<400> SEQUENCE: 23
caaggcgtct gctggcatta                                                    20

<210> SEQ ID NO 24
<211> LENGTH: 20
<212> TYPE: DNA
<213> ORGANISM: Artificial
<220> FEATURE:
<223> OTHER INFORMATION: reverse primer

<400> SEQUENCE: 24
taatgccagc agacgccttg                                                    20

<210> SEQ ID NO 25
<211> LENGTH: 20
<212> TYPE: DNA
<213> ORGANISM: Artificial
<220> FEATURE:
<223> OTHER INFORMATION: forward primer

<400> SEQUENCE: 25
ggaaggtgaa ggtcggagtc                                                    20

<210> SEQ ID NO 26
<211> LENGTH: 20
<212> TYPE: DNA
<213> ORGANISM: Artificial
<220> FEATURE:
<223> OTHER INFORMATION: reverse primer

<400> SEQUENCE: 26
ttcccgttct cagccttgac                                                    20

<210> SEQ ID NO 27
<211> LENGTH: 54
<212> TYPE: DNA
<213> ORGANISM: Homo sapiens

<400> SEQUENCE: 27
tgttgacctc ctcattgtta ttcaagagat aacaatgagg aggtcaactt tttt              54

<210> SEQ ID NO 28
<211> LENGTH: 59
<212> TYPE: DNA
<213> ORGANISM: Homo sapiens
```

```
<400> SEQUENCE: 28
tcgagaaaaa agttgacctc ctcattgtta tctcttgaat aacaatgagg aggtcaaca      59

<210> SEQ ID NO 29
<211> LENGTH: 54
<212> TYPE: DNA
<213> ORGANISM: Homo sapiens

<400> SEQUENCE: 29
tgttggatga tatgacactg ttcaagagac agtgtcatat catccaactt tttt           54

<210> SEQ ID NO 30
<211> LENGTH: 59
<212> TYPE: DNA
<213> ORGANISM: Homo sapiens

<400> SEQUENCE: 30
tcgagaaaaa agttggatga tatgacactg tctcttgaac agtgtcatat catccaaca     59
```